(12) United States Patent (10) Patent No.: US 9,234,210 B2
Famili et al. (45) Date of Patent: Jan. 12, 2016

(54) SELECTABLE MARKERS AND RELATED METHODS

(75) Inventors: Imandokht Famili, San Diego, CA (US); Renata Usaite Black, San Diego, CA (US); Christophe H. Schilling, San Diego, CA (US)

(73) Assignee: Intrexon CEU, Inc., Blacksburg, VA (US)

( * ) Notice: Subject to any disclaimer, the term of this patent is extended or adjusted under 35 U.S.C. 154(b) by 1043 days.

(21) Appl. No.: 13/218,342

(22) Filed: Aug. 25, 2011

(65) Prior Publication Data

US 2012/0196321 A1 Aug. 2, 2012

Related U.S. Application Data

(60) Provisional application No. 61/377,079, filed on Aug. 25, 2010.

(51) Int. Cl.
*C12N 5/10* (2006.01)
*C12N 15/85* (2006.01)
*C12P 1/00* (2006.01)
*C12N 9/02* (2006.01)

(52) U.S. Cl.
CPC .............. *C12N 15/85* (2013.01); *C12N 9/0071* (2013.01); *C12Y 114/16001* (2013.01)

(58) Field of Classification Search
None
See application file for complete search history.

(56) References Cited

U.S. PATENT DOCUMENTS

| | | | |
|---|---|---|---|
| 6,087,489 A | 7/2000 | Dean | |
| 7,736,899 B1 | 6/2010 | Marliere et al. | |
| 7,856,317 B2 | 12/2010 | Schilling | |
| 2003/0166201 A1 | 9/2003 | Jensen | |
| 2003/0233218 A1 | 12/2003 | Schilling | |
| 2004/0029149 A1 | 2/2004 | Palsson et al. | |
| 2004/0148647 A1 | 7/2004 | Enenkel et al. | |
| 2006/0147899 A1 | 7/2006 | Famili et al. | |
| 2009/0035290 A1* | 2/2009 | Chen et al. .................. | 424/94.5 |

FOREIGN PATENT DOCUMENTS

WO WO 03/106998 12/2003
WO WO 2010/098865 9/2010

OTHER PUBLICATIONS

Luka et al. Biochem Biophys Res Commun. Dec. 26, 2003;312(4)1067-72.*
Ayusawa et al., "Selection of mammalian thymidine auxotrophic cell mutants defective in thymidylate synthase by their reduced sensitivity to methotrexate," *Somatic Cell Genet*. 7(5):523-534 (1981).
Browne and Al-Rubeai, "Selection methods for high-producing mammalian cell lines," *Trends Biotechnol*. 25(9):425-432 (2007). (Epub Jul. 30, 2007).
Cockett et al., "High level expression of tissue inhibitor of metalloproteinases in Chinese hamster ovary cells using glutamine synthetase gene amplification," *Biotechnology* (N Y).8(7):662-667 (1990).
Covert and Palsson, "Transcriptional regulation in constraints-based metabolic models of *Escherichia coli*," *J. Biol. Chem.* 277(31):28058-28064 (2002). (Epub May 10, 2002).
Covert et al., "Integrating high-throughput and computational data elucidates bacterial networks," *Nature* 429(6987):92-96 (2004).
Covert et al., "Metabolic modeling of microbial strains in silico," *Trends Biochem. Sci.* 26(3):179-186 (2001).
Covert et al., "Regulation of gene expression in flux balance models of metabolism," *J. Theor. Biol.* 213(1):73-88 (2001).
Duarte et al., "Global reconstruction of the human metabolic network based on genomic and bibliomic data," *Proc. Natl. Acad. Sci. U. S. A.* 104(6):1777-1782 (2007). (Epub Jan. 31, 2007)
Edwards and Palsson, "Metabolic flux balance analysis and the in silico analysis of *Escherichia coli* K-12 gene deletions," *BMC Bioinformatics* 1:1 (2000). (Epub Jul. 27, 2000).
Edwards and Palsson, "Robustness analysis of the *Escherichia coli* metabolic network," *Biotechnol. Prog.* 16(6):927-939 (2000).
Edwards and Palsson, "Systems properties of the Haemophilus influenzae Rd metabolic genotype," *J. Biol. Chem.* 274(25):17410-17416 (1999).
Edwards and Palsson, "The *Escherichia coli* MG1655 in silico metabolic genotype: its definition, characteristics, and capabilities," *Proc. Natl. Acad. Sci. U. S. A.* 97(10):5528-5533 (2000).
Edwards et al., "Characterizing the metabolic phenotype: a phenotype phase plane analysis," *Biotechnol. Bioeng.* 77(1):27-36 (2002).
Edwards et al., "Metabolic modelling of microbes: the flux-balance approach," *Environ. Microbiol.* 4(3):133-140 (2002).
Famili et al., "*Saccharomyces cerevisiae* phenotypes can be predicted by using constraint-based analysis of a genome-scale reconstructed metabolic network," *Proc. Natl. Acad. Sci. U. S. A.*100(23):13134-13139 (2003). (Epub Oct. 24, 2003).
Förster et al., "Genome-scale reconstruction of the *Saccharomyces cerevisiae* metabolic network," *Genome Res.* 13(2):244-253 (2003).
Förster et al., "Large-scale evaluation of in silico gene deletions in *Saccharomyces cerevisiae*," *OMICS* 7(2):193-202 (2003).
García-Ríos et al., "Cloning of a polycistronic cDNA from tomato encoding gamma-glutamyl kinase and gamma-glutamyl phosphate reductase," *Proc. Natl. Acad. Sci. U. S. A*. 94(15):8249-8254 (1997).
Ideker et al., "Integrated genomic and proteomic analyses of a systematically perturbed metabolic network," *Science* 292(5518):929-934 (2001).
Irani et al., "Improvement of the primary metabolism of cell cultures by introducing a new cytoplasmic pyruvate carboxylase reaction," *Biotechnol. Bioeng.* 66(4):238-246 (1999).
Jayapal et al., "Recombinant protein therapeutics from CHO cells—20 years and counting," *Chem. Eng. Prog.* 103:40-47 (2007).
Jeong et al., "Effects of lactate dehydrogenase suppression and glycerol-3-phosphate dehydrogenase overexpression on cellular metabolism," *Mol. Cell Biochem*. 284(1-2):1-8 (2006). (Epub Feb. 14, 2006).
Kao and Puck, "Genetics of somatic mammalian cells, VII. Induction and isolation of nutritional mutants in Chinese hamster cells," *Proc. Natl. Acad. Sci. U. S. A.* 60(4):1275-1281 (1968).
Kao and Puck, "Genetics of somatic mammalian cells. IV. Properties of Chinese hamster cell mutants with respect to the requirement for proline," *Genetics* 55(3):513-524 (1967).

(Continued)

*Primary Examiner* — Christian Fronda
(74) *Attorney, Agent, or Firm* — Jones Day

(57) ABSTRACT

The invention relates to newly identified selectable marker systems, cells for use in a selectable marker system, and methods for using the selectable marker systems.

17 Claims, 15 Drawing Sheets

(56) References Cited

OTHER PUBLICATIONS

Kingston et al., Current Protocols in Molecular Biology (John Wiley & sons, Inc., (1993).
Kohli et al., "Facile methods for generating human somatic cell gene knockouts using recombinant adeno-associated viruses," *Nucleic Acids Res.* 32(1):e3 (2004).
Lakshmi Kamath, Drug Discovery & Development, 1-12 (2005).
Palsson, "The challenges of in silico biology," *Nat. Biotechnol.* 18(11):1147-1150 (2000).
Pissarra, "Changes in the business of culture," *Nat. Biotechnol.* 22(11):1355-1356 (2004).
Price and Palsson, "Genome-scale models of microbial cells: evaluating the consequences of constraints," *Nat. Rev. Microbiol.* 2(11):886-897 (2004).
Santiago et al., "Targeted gene knockout in mammalian cells by using engineered zinc-finger nucleases," *Proc. Natl. Acad. Sci. U. S. A.* 105(15):5809-5814 (2008). (Epub Mar. 21, 2008).
Schilling and Palsson, "Assessment of the metabolic capabilities of Haemophilus influenzae Rd through a genome-scale pathway analysis," *J. Theor. Biol.* 203(3):249-283 (2000).
Schilling et al., "Genome-scale metabolic model of Helicobacter pylori 26695," *J. Bacteriol.* 184(16):4582-4593 (2002).
Schilling et al., "Toward metabolic phenomics: analysis of genomic data using flux balances," *Biotechnol. Prog.* 15(3):288-295 (1999).
Schuster et al., "Exploring the pathway structure of metabolism: decomposition into subnetworks and application to Mycoplasma pneumoniae," *Bioinformatics* 18(2):351-361 (2002).
Seth et al., "In pursuit of a super producer-alternative paths to high producing recombinant mammalian cells," *Curr. Opin. Biotechnol.* 18(6):557-564 (2007). (Epub Dec. 21, 2007).
Sørlie et al., "Gene expression patterns of breast carcinomas distinguish tumor subclasses with clinical implications," *Proc. Natl. Acad. Sci. U. S. A.* 98(19):10869-10874 (2001).
Stephanopoulos et al., Metabolic Engineering: Principles and Methodologies, Academic Press, San Diego, CA (1998).
Urlaub and Chasin, "Isolation of Chinese hamster cell mutants deficient in dihydrofolate reductase activity," *Proc. Natl. Acad. Sci. U. S. A.* 77(7):4216-4220 (1980).
Urnov et al., "Highly efficient endogenous human gene correction using designed zinc-finger nucleases," *Nature* 435(7042):646-651 (2005). (Epub Apr. 3, 2005).
Varma and Palsson, "Stoichiometric flux balance models quantitatively predict growth and metabolic by-product secretion in wild-type *Escherichia coli* W3110," *Appl. Environ. Microbiol.* 60(10):3724-3731 (1994).
Varma and Palsson, "Metabolic Flux Balancing: Basic Concepts, Scientific and Practical Use," *Bio/Technology* 12:944-998 (1994).
Vasquez et al., "Manipulating the mammalian genome by homologous recombination," *Proc. Natl. Acad. Sci. U. S. A.* 98(15):8403-8410 (2001).
Walsh, "Biopharmaceutical benchmarks—2003," *Nat. Biotechnol.* 21(8):865-870 (2003).
Wurm, "Production of recombinant protein therapeutics in cultivated mammalian cells," *Nat. Biotechnol.* 22(11):1393-1398 (2004).
Zhang et al., "Metabolic characteristics of recombinant Chinese hamster ovary cells expressing glutamine synthetase in presence and absence of glutamine," *Cytotechnology* 51(1):21-28 (2006). (Epub Aug. 5, 2006).
Zhu et al., "Regulation of tetrahydrobiopterin biosynthesis in cultured dopamine neurons by depolarization and cAMP," *J. Biol. Chem.* 269(16):11825-11829 (1994).

* cited by examiner

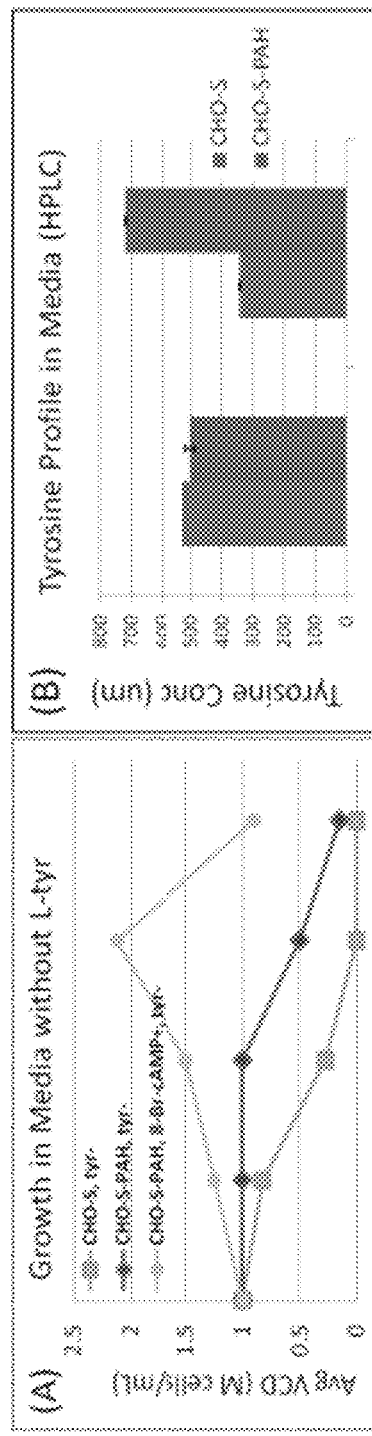
FIGURE 10A
FIGURE 10B
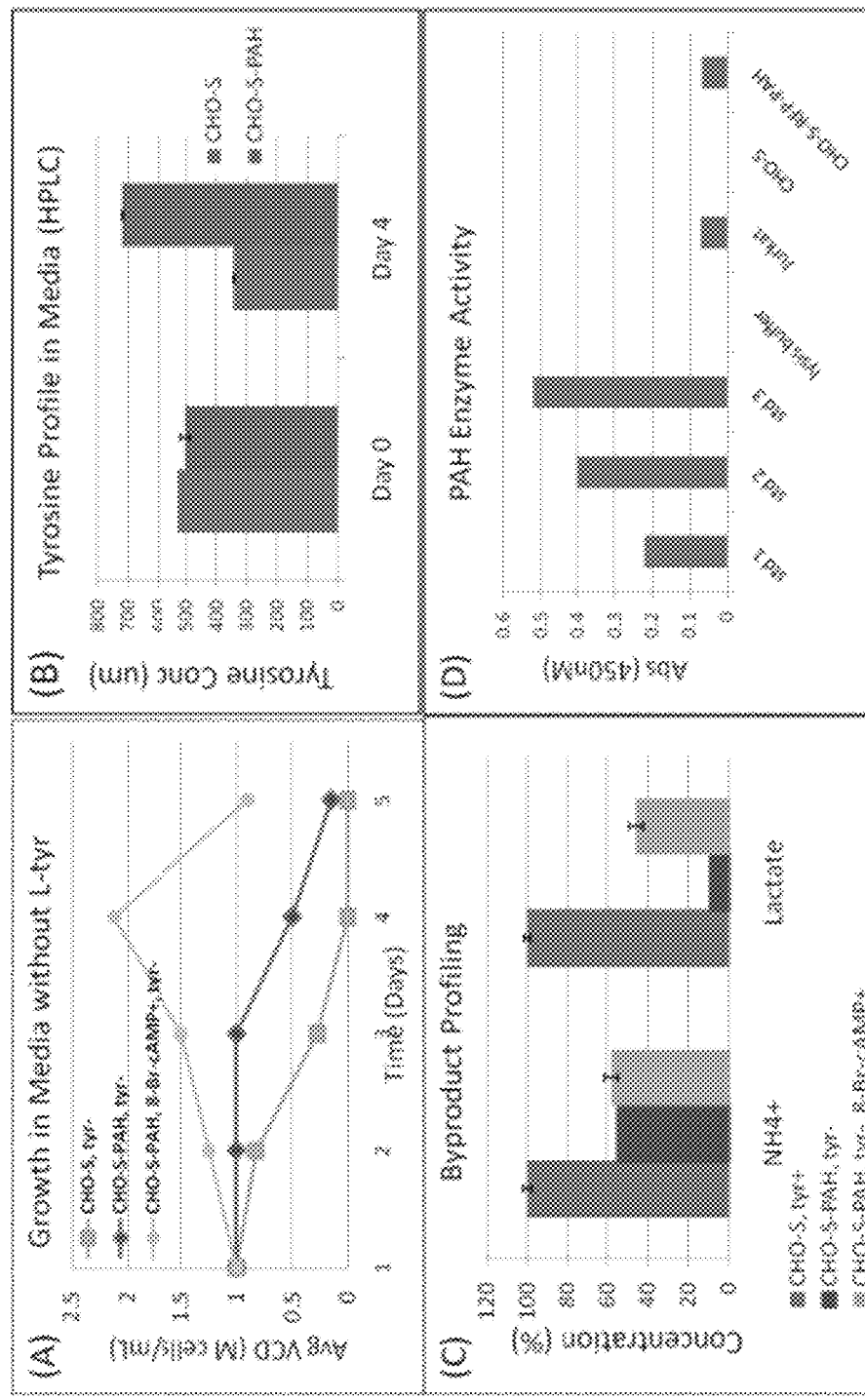
FIGURE 10C
FIGURE 10D

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agctgaagca cgccaagaga attg                                              24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
attccaactt cagctcccag tcca                                              24

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgctgagac acatgcaccg c                                                 21

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcagctgaaa tttctctggg gaac                                              24

SELECTABLE MARKERS AND RELATED METHODS

This application claims the benefit of priority of U.S. Provisional application Ser. No. 61/377,079, filed Aug. 25, 2010, the entire contents of which are incorporated herein by reference.

This invention was made with government support under grant number 1R43GM088898-01 awarded by National Institute of General Medical Sciences. The government has certain rights in the invention.

The instant application contains a Sequence Listing which has been submitted in ASCII format via EFS-Web and is hereby incorporated by reference in its entirety. Said ASCII copy, created on Apr. 10, 2012, is named 12966-006-999_ 12966699.txt and is 1,299 bytes in size.

BACKGROUND OF THE INVENTION

The present invention relates generally to cell lines and cell cultures, and models thereof, and more specifically to selection systems.

Protein-based therapeutic products have contributed immensely to healthcare and constitute a large and growing percentage of the total pharmaceutical market. Therapeutic proteins first entered the market less than 20 years ago and have already grown to encompass 10-30% of the total US market for pharmaceuticals. The trend towards therapeutic proteins is accelerating. In recent years, more than half of the new molecular entities to receive FDA approval were biologics produced mostly in mammalian cell systems, and an estimated 700 or more protein-based therapeutics are at various stages of clinical development, with 150 to 200 in late-stage trials.

Over the past two decades, substantial progress has been made to overcome some of the key barriers to large-scale mammalian cell culture, including improvements in vector design, host cell engineering, medium development, screening methods and process engineering, resulting in yield improvements of up to 100-fold over titers seen in the mid 1980's. Despite these improvements, developing new biopharmaceutical products remains an expensive and lengthy process, typically taking six years from pre-clinical process development to product launch, where 20-30% of the total cost is associated with process development and clinical manufacturing. Production costs by mammalian cell culture remain high, and new methods to provide a more effective approach to optimize overall process development are of highest interest to the industry, particularly as regulatory constraints on development timelines remain stringent and production demands for new therapeutics are rapidly rising, especially for the quantities required for treatment of chronic diseases. Production costs are a major concern for management planning, especially with intense product competition, patent expirations, introduction of second-generation therapeutics and accompanying price pressure, and pricing constraints imposed by regulators and reimbursement agencies. Reducing the cost of therapeutic protein development and manufacturing would do much to ensure that the next generation of medicines can be created in amounts large enough to meet patients' needs, and at a price low enough that patients can afford.

Traditionally, mammalian cells are engineered to express a desired product. Among the methods used to engineer such cells, selectable markers are generally used to ensure the selection of cells that express a desired product and, in some cases, amplify the copy number of the nucleic acid encoding the product to increase production. However, to date only a limited number of selectable markers, such as dihydroflate reductase or glutamine synthetase, have been found general use in mammalian cells. It is therefore desirable to identify additional selectable markers for genetic engineering of mammalian cells for production of biologics or other desired products.

Thus, there exists a need to provide selectable markers for engineering expression in mammalian cells of desired products such as biologics. The present invention satisfies this need and provides related advantages as well.

SUMMARY OF INVENTION

The invention relates to newly identified selectable marker systems, cells for use in a selectable marker system, and methods for using the selectable marker systems.

BRIEF DESCRIPTION OF THE DRAWINGS

FIGS. 10A-10D show validation results for phenylalanine 4-monooxygenase (PAH) selectable marker. FIG. 10A: Viable cell density was monitored over time in untransfected and transfected Free-style CHO-S cells in media without tyrosine. Supplementation of 8-Br-cAMP induced cells to grow. Maximum VCD in transfected CHO-S cell lines in Tyr− media did not reach the levels observed in untransfected CHO-S in Tyr+ media. FIG. 10B: HPLC analysis shows an increase in media concentration of tyrosine by day 4 in transfected CHO-S cells, only. FIG. 10C: Enzymatic assays showed significantly lower lactate and $NH_4^+$ peak concentrations in transfected CHO-S cells in Tyr− media compared with untransfected cell in Tyr+ media. FIG. 10D: Enzymatic assay showing activity of PAH (measured as increase in absorption over time) in crude lysates from transfected CHO-S cells over untransfected cells (crude lysate from jurkat cells was used as a positive control).

FIG. 11A: Growth study showed significantly higher (by 8%) maximum specific growth rate, and significantly lower (by 27%) C-mol consumption to produce one C-mol of biomass in CHO-S-P5CS compared to CHO-S cell line. FIG. 11B: Flux Variability Analysis performed using SimPheny™ showed that, in non-transfected cell line CHO-S, there was a requirement to produce four byproducts.

DETAILED DESCRIPTION OF THE INVENTION

Figure 1:
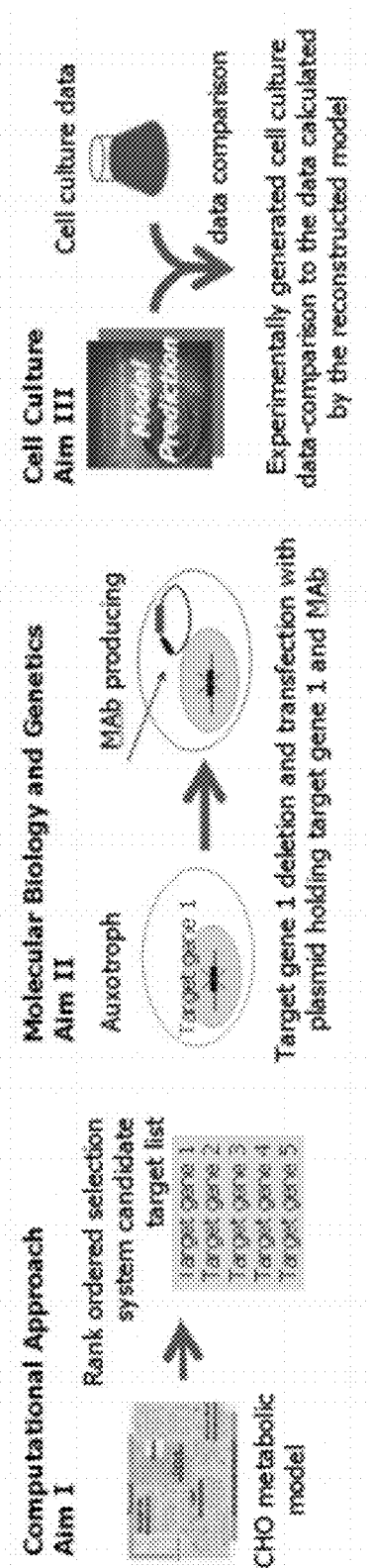
FIG. 1 shows strategy to create an improved selection system in Chinese Hamster Ovary cell line. A target selection marker gene can be identified using a computational approach with the reconstructed CHO cell metabolic model. Computationally designed selection system can be implemented by first disrupting target gene 1, if needed, and then inserting it back on a plasmid as a selection marker. Model predicted and experimentally generated cell culture data can be compared and strategies for the selection system design improvements can be created.

The invention provides selectable marker systems identified by metabolic models of cells. Metabolic models are used to identify reactions required for cell growth or cell viability, thereby identifying a target selectable marker reaction or reactant. The invention provides cells selected for or engineered to lack expression of a protein that is identified by the model as being required for cell growth or viability. For example, the protein can be an enzyme involved in production of a nutrient required for cell growth. In the absence of expression of the protein and the absence of the nutrient from the cell culture medium, the cell will be unable to grow, that is, it is an auxotroph for the nutrient. Such a relationship can be exploited to provide a selectable marker system by introducing the protein into such a cell recombinantly and then screening for cells in which the protein is expressed. Cells expressing the protein will be able to grow in the medium in the absence of the nutrient, that is, in the selection medium. The invention is based on determining reactions that produce a product that can be removed from a defined culture medium to identify a protein that produces a product that can be excluded from the medium and complemented by either addition of the product to the medium (non-selective medium) or by expression of the protein to produce the product, thereby allowing growth of the cells in the absence of the product in the medium (selective medium). The methods of the invention are advantageous in providing a model-based approach to identifying target selectable marker reactions that can be engineered into cells to provide a desired phenotype that can be exploited as a selection system. Such a selection system can be utilized for genetically engineering cells to express a desired product.

A model-based method for selection system design has been previously described (see WO 2010/098865, filed Feb. 26, 2010). Such methods and models, also described herein, utilize the knowledge of a whole cell metabolism and is capable of providing rational designs for identifying new selection systems. An integrated computational and experimental approach has been used to identify new selection systems in a CHO cell line and experimentally implement the most promising and advantageous candidate to validate the approach (see Examples). This approach can be implemented in three stages: (1) identify essential metabolic reactions that are candidate targets for designing selection systems using a reconstructed metabolic model of a cell line such as hybridoma, NS0, or CHO, or other cell model, rank-order and prioritize the candidate targets based on a number of criteria including the predicted stringent specificity of the new selection system and improved cell physiology, (2) experimentally implement the top candidate selection system in a cell line using experimental techniques such as by first creating an auxotrophic clone, transiently transfecting cells with a selection vector, for example, a selection vector that includes an antibody-expressing gene, and selecting protein producing cell lines based on their auxotrophy, and (3) evaluate the development and implementation of a model-based selection system in the cells by comparing experimentally generated cell culture data with those calculated by the reconstructed model. This integrated computational and experimental platform allows for design of new and superior metabolic selection systems in mammalian based protein production by computationally identifying and experimentally developing new selection systems.

As disclosed herein, new selectable marker systems have been identified (see Examples I-IV). The invention provides a cell, wherein the cell has been genetically engineered to disrupt expression of a protein of Table 1. Such a protein can be, for example, a protein selected from argininosuccinate lyase, cystathionine G-lyase, cystathionine b-synthase, glycine N-methyltransferase, pyrroline-5-carboxylate synthetase, phenylalanine 4-monooxygenase, carbamoyl-phosphate synthase (ammonia), ornithine carbamoyltransferase (mitochondrial), ornithine transaminase (mitochondrial), methionine adenosyltransferase, adenosylhomocysteinase, propionyl-CoA carboxylase (mitochondrial), methylmalonyl-CoA epimerase (mitochondrial), methylmalonyl-CoA mutase, myo-Inositol-1-phosphate synthase, thymidylate synthase, nucleoside-diphosphatase (dUDP), carbonate anhydrase, adenosine kinase, sarcosine oxidase, alphaketobutyrate dehydrogenase (mitochondrial), phosphatidylserine decarboxylase, glucose-6-phosphate isomerase, myo-inositol 1-phosphatase, ribonucleoside-diphosphate reductase, and dihydropteridine reductase.

As used herein, the phrase "genetically engineered to disrupt expression of a protein" refers to a cell in which expression of a protein has been disrupted, generally by disruption of the encoding gene, using genetic engineering techniques. Methods of genetically engineering a cell for gene disruption are well known in the art and include well known molecular biology techniques (Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999)). Such methods include, for example, targeted gene disruption. A cell genetically engineered to disrupt expression of a protein specifically excludes cells that occur naturally that do not express a target protein, such as those described herein (see Example II). A cell genetically engineered to disrupt expression of a protein can be a cell in which targeted gene disruption has been used that is specific to targeting disruption of the desired proteins. Such methods are well known to those skilled in the art, including but not limited to, homologous recombination and engineered zinc finger nucleases (Santiago et al., *Proc. Natl. Acad. Sci. USA* 105:5809-5814 (2008); Mansour et al., *Nature* 336:348-352 (1988); Vasquez et al., *Proc. Natl. Acad. Sci. USA* 98:8403-8410 (2001); Yamane-Ohnuki et al., *Biotechnol. Bioengineer.* 87:614-622 (2004); Kohli et al., *Nucleic Acids Res.* 32:e3 (2004); Hirata et al., *Nat. Biotechnol.* 20:735-738 (2002); Ausubel et al., supra).

As used herein, the term "gene disruption," or grammatical equivalents thereof, is intended to mean a genetic alteration that renders the encoded gene product inactive. The genetic alteration can be, for example, deletion of the entire gene, deletion of a regulatory sequence required for transcription or translation, deletion of a portion of the gene which results in a truncated gene product, or by any of various mutation strategies that inactivate the encoded gene product. One particularly useful method of gene disruption is complete gene deletion because it reduces or eliminates the occurrence of genetic reversions in the cell. In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For a gene disruption, evolutionarily related genes can also be disrupted or deleted in the parent cell to reduce or eliminate functional redundancy of enzymatic activities targeted for disruption.

Given the teachings and guidance provided herein and methods well known in the art, those skilled in the art will understand that to introduce a metabolic alteration such as disruption of an enzymatic reaction, it is necessary to disrupt the catalytic activity of the one or more enzymes involved in the reaction. Disruption can occur by a variety of methods including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity, disruption can occur by a genetic alteration that reduces or eliminates the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits required to form an active complex, by destruction of the catalytic subunit of the multimeric complex or by both. Other functions of multimeric protein association and activity also can be targeted in order to disrupt a metabolic reaction. Such other functions are well known to those skilled in the art. Similarly, a target enzyme activity can be reduced or eliminated by disrupting expression of a protein or enzyme that modifies and/or activates the target enzyme, for example, a molecule required to convert an apoenzyme to a holoenzyme. Further, some or all of the functions of a single polypeptide or multimeric complex can be disrupted according to the invention in order to reduce or abolish the catalytic activity of one or more enzymes involved in a reaction.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of catalytic activity of a targeted reaction. An ortholog is a gene or genes that are related by vertical descent and are responsible for substantially the same or identical functions in different organisms. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. In contrast, paralogs are homologs related by, for example, duplication followed by evolutionary divergence and have similar or common, but not identical functions. Paralogs can originate or derive from, for example, the same species or from a different species. Paralogs are proteins from the same species with significant sequence similarity to each other suggesting that they are homologous, or related through co-evolution from a common ancestor.

The cells of the invention are useful as a parental cell for use in a selectable marker system. Such cells are generally used for expression of recombinant proteins. Thus, such a cell can further comprise an exogenous nucleic acid, wherein the exogenous nucleic acid comprises an expressible nucleic acid comprising a nucleic acid encoding the protein lacking expression in the cell. Thus, the expressible nucleic acid can be used as part of a selectable marker system to provide a provide a protein activity lacking in a parental cell used in a selectable marker system, such as those disclosed herein.

The exogenous nucleic acid can further comprise an expressible nucleic acid encoding a product. Thus, the selectable marker systems described herein can be used to express a desired product by selecting for cell clones that have taken up the expressible nucleic acid and express the encoded product. Such a product may be a nucleic acid or protein product. The selectable marker systems of the invention are particularly useful for expressing a desired protein product. It is understood that, when an expressible nucleic acid containing a selectable marker is used for expression of a desired product, the encoded product and the selectable marker are generally provided on the same expressible nucleic acid. However, it is not required that the nucleic acid encoding the selectable marker and the nucleic acid encoding the desired product reside on the same expressible nucleic acid and can be provided to a cell as separate expressible nucleic acids. As used herein, an "expressible nucleic acid" means that the nucleic acid is capable of operably expressing a nucleic acid sequence. In the case of a selectable marker or desired product, it is understood that the expressible nucleic acid includes any promoters and/or enhancers required for expression of the encoded product in the host cell, in particular the selectable marker protein, such as those found in Table 1, or a desired protein product. In general, the selectable marker and desired product are expressible from independent promoters and/or enhances if present on the same exogenous nucleic acid molecule, but it is understood that the selectable marker and desired product can be expressed from polycistronic vectors. Expressible nucleic acids can be in the form of any of the well known expression vectors, including plasmid vectors, viral vectors, and the like, (see Sambrook et al., supra, and Ausubel et al., supra), or any suitable expression vector, including numerous commercially available vectors or custom vectors, so long as the vector contains the expression elements such as promoters and/or enhancers sufficient to allow expression of a selectable marker and/or desired product.

The invention additionally provides a composition comprising a cell and an expressible nucleic acid. The cell is a cell that lacks expression of a protein of Table 1, which can function in a selectable marker system. The expressible nucleic acid can encode the protein lacking expression in the cell. In a particular embodiment, such proteins lacking expression in a cell can be argininosuccinate lyase, cystathionine G-lyase, cystathionine b-synthase, glycine N-methyltransferase, pyrroline-5-carboxylate synthetase, phenylalanine 4-monooxygenase, carbamoyl-phosphate synthase (ammonia), ornithine carbamoyltransferase (mitochondrial), ornithine transaminase (mitochondrial), methionine adenosyltransferase, adenosylhomocysteinase, propionyl-CoA carboxylase (mitochondrial), methylmalonyl-CoA epimerase (mitochondrial), methylmalonyl-CoA mutase, myo-Inositol-1-phosphate synthase, thymidylate synthase, nucleoside-diphosphatase (dUDP), carbonate anhydrase, adenosine kinase, sarcosine oxidase, alphaketobutyrate dehydrogenase (mitochondrial), phosphatidylserine decarboxylase, glucose-6-phosphate isomerase, myo-inositol 1-phosphatase, ribonucleoside-diphosphate reductase, or dihydropteridine reductase.

The invention additionally provides a kit containing the composition. Such a kit can therefore include a cell and expressible nucleic acid that together provide a selection system. The kit can further comprise appropriate written instructions for using the selectable marker kit. The kit can additionally comprise the components of a selection medium for culturing the cell under selection conditions. As used herein, a "selection medium" is a medium, generally a defined medium, that contains components that allow growth of a cell if a selectable marker is present in the cell. Thus, the selection medium excludes a component that results in selective pressure on the cells such that cells lacking a selectable marker will not grow or will die. For example, the selection medium can be prepared so that a component of Table 1 that complements the lack of expression of a corresponding protein is absent in the selection medium. In such a case, parental cells that lack expression of the selectable marker protein, such as those in Table 1, will not grow whereas cells that have been transfected such as with a plasmid vector or transduced such as with a viral vector will be able to grow due to the expression of the protein provided by the exogenous nucleic acid containing an expressible nucleic acid encoding the selectable marker protein. With respect to the proteins of Table 1, the selection medium can be prepared so that a selection component that complements a protein in Table 1 is absent. Such components can be, for example, arginine, cysteine, proline, tyrosine, myo-inositol, thymidine, ethanolamine, glucose, asparagine or glutamine. In contrast to selection medium, "complete medium" is used herein to refer to a medium in which the selection medium has been supplemented with the omitted component that makes the medium selective, such as the complementary components found in Table 1.

The invention also provides a method of selecting for an exogenous nucleic acid in a cell. The method can include the steps of contacting cells with an exogenous nucleic acid, wherein the cells lack expression of a protein of Table 1 and wherein the exogenous nucleic acid comprises a nucleic acid encoding the protein lacking expression in the cell, wherein the contacting results in uptake of the exogenous nucleic acid into at least one of the cells; placing the cells in a selection medium, wherein the components of the selection medium exclude the component of Table 1 that complements the lack of expression of the protein; and culturing the cells in the selection medium, whereby culturing the cells selects for at least one cell that expresses from the exogenous nucleic acid the protein lacking expression in the cell. Thus, the methods of the invention are directed to using a selectable marker system based on the identification, as disclosed herein, of protein activities and corresponding products that, together, provide complementary functions that can be exploited in a cell selection system. Such proteins are disclosed herein in Table 1 and include argininosuccinate lyase, cystathionine G-lyase, cystathionine b-synthase, glycine N-methyltransferase, pyrroline-5-carboxylate synthetase, phenylalanine 4-monooxygenase, carbamoyl-phosphate synthase (ammonia), ornithine carbamoyltransferase (mitochondrial), ornithine transaminase (mitochondrial), methionine adenosyltransferase, adenosylhomocysteinase, propionyl-CoA carboxylase (mitochondrial), methylmalonyl-CoA epimerase (mitochondrial), methylmalonyl-CoA mutase, myo-Inositol-1-phosphate synthase, thymidylate synthase, nucleoside-diphosphatase (dUDP), carbonate anhydrase, adenosine kinase, sarcosine oxidase, alphaketobutyrate dehydrogenase (mitochondrial), phosphatidylserine decarboxylase, glucose-6-phosphate isomerase, myo-inositol 1-phosphatase, ribonucleoside-diphosphate reductase, and dihydropteridine reductase. The corresponding component of Table 1 complementary to these proteins includes arginine, cysteine, proline, tyrosine, myo-inositol, thymidine, ethanolamine, glucose, asparagine and glutamine.

As disclosed herein, it is understood that a medium component that can "complement" a protein is a component that, when present in the medium, allows a parental cell to grow when the protein is not expressed, that is, is an auxotroph for the component. Conversely, expression of the corresponding protein allows a cell to grow in the absence of the complementary component in the medium. This relationship allows a selection system to be provided based on the correspondence of a protein activity complementing the absence of a auxotrophic component in a selection medium, as described herein (see Example II).

Such a selection system and method of the invention can be utilized to express a desired product encoded on an exogenous nucleic acid. Thus, the selectable marker systems disclosed herein can be similar to other well known selection systems such as dihydrofolate reductase (DHFR) or glutamine synthetase (GS) to genetically engineer a cell for uptake and expression of a heterologous nucleic acid, and in particular to express a desired protein product. A desired product can therefore be expressed in the selected cell. As is well known in the art, the product can be isolated from the cell, either by collection of medium in which the product is secreted or lysing the cells, and separated from the cells or crude cell lysate using routine purification methods well known in the art and appropriate for purification of the desired product.

It is well known to those skilled in the art that cells can be genetically engineered and manipulated with routine molecular biology techniques to uptake and express nucleic acids contacted with the cells using well known transfection or viral transduction techniques, as described, for example, in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999). It is understood that any suitable technique that results in uptake of an exogenous nucleic acid can be used in the methods disclosed herein. It is also well known that such expression can be transient or stable. Although it is understood that the selectable marker systems disclosed herein can be used for transient or stable expression, it is further understood that the use of selectable marker systems is particularly useful for providing stable expression of an exogenous nucleic acid. The continued culturing of cells under selective conditions applies selective pressure that requires selected cells to retain expression of the selectable marker. It is well known that such a selection system can be used to introduce an exogenous nucleic acid into the cell. Although not required, such a selection system is generally more efficient for providing expression of a desired product if the selectable marker and desired product are linked and provided on the same exogenous nucleic acid molecule. Furthermore, while not required, it is generally desirable and the selection systems described herein are advantageous for providing stable cell lines. As used herein, a "stable cell line" is one in which successive generations of cells are capable of displaying a desired phenotype such as expression of a desired product. It is understood that a stable cell line can include cells that, in successive generations, increase or decrease expression of a desired product or otherwise differ, so long as desirable phenotype is maintained. Although not required, it is well known that the use of selection systems to establish stable cell lines often leads to integration of at least a portion of an introduced exogenous nucleic acid such that the selectable marker and/or the desired product, if present, are integrated into the host genome. However, it is understood that integration into the host genome is not required and that the selection systems of the present invention can function if the nucleic acids encoding the selectable marker and/or desired product remain episomal. In addition, it is known that selection systems can display the function of amplifying copy number of the selectable marker and/or desired product (see below). Therefore, it is understood that the selectable markers of the present invention can similar be used to amplify the copy number if such a phenotype is exhibited by the selection systems of the invention.

Furthermore, methods of selecting a cell are well known to those skilled in the art (see Freshney, *Culture of Animal Cells: A Manual of Basic Technique*, 4th ed., Wiley-Liss, New York (2000). It is understood that cells are cultured under selective conditions and for a sufficient period of time to select for cells expressing the selectable marker. It is further understood that such a time generally includes several doubling times for the cells so that those cells expressing the selectable marker grow relative the lack of growth or cell death of cells that lack the selectable marker. The amount of time depends on the growth rate of the particular cell under the particular selection system and is generally at least a few days to several weeks or months, if needed.

Thus, the invention provides a method of expressing a product in a cell. The method can include the steps of contacting cells with an exogenous nucleic acid, wherein the cells lack expression of a protein of Table 1 and wherein the exogenous nucleic acid comprises a nucleic acid encoding the protein lacking expression in the cell and an expressible nucleic acid encoding the product, wherein the contacting results in uptake of the exogenous nucleic acid into at least one of the cells; placing the cells in a selection medium, wherein the components of the selection medium exclude the component of Table 1 that complements the lack of expression of the protein; culturing the cells in the selection medium, whereby culturing the cells selects for at least one cell that expresses from the exogenous nucleic acid the protein lacking expression in the cell; and culturing the selected cell under conditions for expression of said product.

The selection systems of the invention provide additional selectable markers than those already known and in use, such as dhfr and glutamine synthetase. Such additional selectable markers can have improved phenotypes and growth characteristics over previously known selection systems. In addition, the selectable markers of the present invention provide additional markers that can be used for dual selection with previously known selection markers or with those disclosed herein. Thus, any of the selectable markers disclosed herein can be used alone or in combination with other selectable markers, as desired.

The in silico models are based on a data structure relating a plurality of reactants to a plurality of reactions, wherein each of the reactions includes a reactant identified as a substrate of the reaction, a reactant identified as a product of the reaction and a stoichiometric coefficient relating the substrate and the product. The reactions included in the data structure can be those that are common to all or most cells or to a particular type or species of cell, for example a particular cell line, such as core metabolic reactions, or reactions specific for one or more given cell type.

As used herein, the term "reaction" is intended to mean a conversion that consumes a substrate or forms a product that occurs in or by a cell. The term can include a conversion that occurs due to the activity of one or more enzymes that are genetically encoded by a genome of the cell. The term can also include a conversion that occurs spontaneously in a cell. Conversions included in the term include, for example, changes in chemical composition such as those due to nucleophilic or electrophilic addition, nucleophilic or electrophilic substitution, elimination, isomerization, deamination, phosphorylation, methylation, reduction, oxidation or changes in location such as those that occur due to a transport reaction that moves a reactant from one cellular compartment to another. In the case of a transport reaction, the substrate and product of the reaction can be chemically the same and the substrate and product can be differentiated according to location in a particular cellular compartment. Thus, a reaction that transports a chemically unchanged reactant from a first compartment to a second compartment has as its substrate the reactant in the first compartment and as its product the reactant in the second compartment. It will be understood that when used in reference to an in silico model or data structure, a reaction is intended to be a representation of a chemical conversion that consumes a substrate or produces a product.

As used herein, the term "reactant" is intended to mean a chemical that is a substrate or a product of a reaction that occurs in or by a cell. The term can include substrates or products of reactions performed by one or more enzymes encoded by a genome, reactions occurring in cells or organisms that are performed by one or more non-genetically encoded macromolecule, protein or enzyme, or reactions that occur spontaneously in a cell. Metabolites are understood to be reactants within the meaning of the term. It will be understood that when used in reference to an in silico model or data structure, a reactant is intended to be a representation of a chemical that is a substrate or a product of a reaction that occurs in or by a cell.

As used herein the term "substrate" is intended to mean a reactant that can be converted to one or more products by a reaction. The term can include, for example, a reactant that is to be chemically changed due to nucleophilic or electrophilic addition, nucleophilic or electrophilic substitution, elimination, isomerization, deamination, phosphorylation, methylation, reduction, oxidation or that is to change location such as by being transported across a membrane or to a different compartment.

As used herein, the term "product" is intended to mean a reactant that results from a reaction with one or more substrates. The term can include, for example, a reactant that has been chemically changed due to nucleophilic or electrophilic addition, nucleophilic or electrophilic substitution, elimination, isomerization, deamination, phosphorylation, methylation, reduction or oxidation or that has changed location such as by being transported across a membrane or to a different compartment.

As used herein, the term "stoichiometric coefficient" is intended to mean a numerical constant correlating the number of one or more reactants and the number of one or more products in a chemical reaction. Typically, the numbers are integers as they denote the number of molecules of each reactant in an elementally balanced chemical equation that describes the corresponding conversion. However, in some cases the numbers can take on non-integer values, for example, when used in a lumped reaction or to reflect empirical data.

As used herein, the term "plurality," when used in reference to reactions or reactants is intended to mean at least 2 reactions or reactants. The term can include any number of reactions or reactants in the range from 2 to the number of naturally occurring reactants or reactions for a particular cell or cells. Thus, the term can include, for example, at least 10, 20, 30, 50, 100, 150, 200, 300, 400, 500, 600 or more reactions or reactants. The number of reactions or reactants can be expressed as a portion of the total number of naturally occurring reactions for a particular cell or cells, such as at least 20%, 30%, 50%, 60%, 75%, 90%, 95% or 98% of the total number of naturally occurring reactions that occur in a particular cell.

As used herein, the term "data structure" is intended to mean a physical or logical relationship among data elements, designed to support specific data manipulation functions. The term can include, for example, a list of data elements that can be added combined or otherwise manipulated such as a list of representations for reactions from which reactants can be related in a matrix or network. The term can also include a matrix that correlates data elements from two or more lists of information such as a matrix that correlates reactants to reactions. Information included in the term can represent, for example, a substrate or product of a chemical reaction, a chemical reaction relating one or more substrates to one or more products, a constraint placed on a reaction, or a stoichiometric coefficient.

As used herein, the term "constraint" is intended to mean an upper or lower boundary for a reaction. A boundary can specify a minimum or maximum flow of mass, electrons or energy through a reaction. A boundary can further specify directionality of a reaction. A boundary can be a constant value such as zero, infinity, or a numerical value such as an integer. Alternatively, a boundary can be a variable boundary value as set forth below.

As used herein, the term "variable," when used in reference to a constraint is intended to mean capable of assuming any of a set of values in response to being acted upon by a constraint function. The term "function," when used in the context of a constraint, is intended to be consistent with the meaning of the term as it is understood in the computer and mathematical arts. A function can be binary such that changes correspond to a reaction being off or on. Alternatively, continuous functions can be used such that changes in boundary values correspond to increases or decreases in activity. Such increases or decreases can also be binned or effectively digitized by a function capable of converting sets of values to discreet integer values. A function included in the term can correlate a boundary value with the presence, absence or amount of a biochemical reaction network participant such as a reactant, reaction, enzyme or gene. A function included in the term can correlate a boundary value with an outcome of at least one reaction in a reaction network that includes the reaction that is constrained by the boundary limit. A function included in the term can also correlate a boundary value with an environmental condition such as time, pH, temperature or redox potential.

As used herein, the term "activity," when used in reference to a reaction, is intended to mean the amount of product produced by the reaction, the amount of substrate consumed by the reaction or the rate at which a product is produced or a substrate is consumed. The amount of product produced by the reaction, the amount of substrate consumed by the reaction or the rate at which a product is produced or a substrate is consumed can also be referred to as the flux for the reaction.

As used herein, the term "activity," when used in reference to a cell, is intended to mean the magnitude or rate of a change from an initial state to a final state. The term can include, for example, the amount of a chemical consumed or produced by a cell, the rate at which a chemical is consumed or produced by a cell, the amount or rate of growth of a cell or the amount of or rate at which energy, mass or electrons flow through a particular subset of reactions.

Depending on the application, the plurality of reactions for a cell model or method of the invention, can include reactions selected from core metabolic reactions or peripheral metabolic reactions. As used herein, the term "core," when used in reference to a metabolic pathway, is intended to mean a metabolic pathway selected from glycolysis/gluconeogenesis, the pentose phosphate pathway (PPP), the tricarboxylic acid (TCA) cycle, glycogen storage, electron transfer system (ETS), the malate/aspartate shuttle, the glycerol phosphate shuttle, and plasma and mitochondrial membrane transporters. As used herein, the term "peripheral," when used in reference to a metabolic pathway, is intended to mean a metabolic pathway that includes one or more reactions that are not a part of a core metabolic pathway.

A plurality of reactants can be related to a plurality of reactions in any data structure that represents, for each reactant, the reactions by which it is consumed or produced. Thus, the data structure, which is referred to herein as a "reaction network data structure," serves as a representation of a biological reaction network or system. An example of a reaction network that can be represented in a reaction network data structure is the collection of reactions that constitute the metabolic reactions of cell lines, as described in the Examples. The choice of reactions to include in a particular reaction network data structure, from among all the possible reactions that can occur in a cell being modeled depends on the cell type and the physiological condition being modeled, and can be determined experimentally or from the literature, as described further below. Thus, the choice of reactions to include in a particular reaction network data structure can be selected depending on whether media optimization, cell line optimization, process development, or other methods and desired results disclosed herein are selected.

The reactions to be included in a particular network data structure can be determined experimentally using, for example, gene or protein expression profiles, where the molecular characteristics of the cell can be correlated to the expression levels. The expression or lack of expression of genes or proteins in a cell type can be used in determining whether a reaction is included in the model by association to the expressed gene(s) and or protein(s). Thus, it is possible to use experimental technologies to determine which genes and/or proteins are expressed in a specific cell type, and to further use this information to determine which reactions are present in the cell type of interest. In this way a subset of reactions from all of those reactions that can occur in cells in generally, for example, mammalian cells, are selected to comprise the set of reactions that represent a specific cell type. cDNA expression profiles have been demonstrated to be useful, for example, for classification of breast cancer cells (Sorlie et al., *Proc. Natl. Acad. Sci. U.S.A.* 98(19):10869-10874 (2001)).

The methods and selectable marker systems disclosed herein can be used in a cell derived from an animal, plant or insect. As used herein, a "derived from an animal, plant or insect" refers to a cell that is of animal, plant or insect origin that has been obtained from an animal, plant or insect. Such a cell can be an established cell line or a primary culture. Cell lines are commercially available and can be obtained, for example, from sources such as the American Type American Type Culture Collection (ATCC) (Manassas Va.) or other commercial sources. In a particular embodiment, the cell can be a mammalian cell, such as a mammalian cell line including, but not limited to, Chinese Hamster Ovary (CHO), BHK, NS0, SP2/0, 3T3, Hybridoma, C127, HEK293, PER.C6, HepG2, HeLa, MRC5, WI38, MDCK, Vero, and COS. It is understood that cell variants, such as CHO DHFR-cells or GS-NS0 cells, and the like, can be used in combination with the selection systems described herein. Generally the cells of the invention are obtained from a multicellular organism, in particular a eukaryotic cell from a multicellular organism, in contrast to a cell that exists as a single celled organism such as yeast. Thus, a eukaryotic cell from a multicellular organism as used herein specifically excludes yeast cells.

It is understood that the methods relating to in silico modeling are generally performed on a computer. Thus, the methods can be performed, for example, with appropriate computer executable commands stored on a computer readable medium or media that carry out the steps of any of the methods disclosed herein. For example, if desired, a data structure can be stored on a computer readable medium or media and accessed to provide the data structure for use with a method of the invention. Additionally, if desired, any and up to all commands for performing the steps of a method can be stored on a computer readable medium or media and utilized to perform the steps of a method. Thus, the invention provides a computer readable medium or media having stored thereon computer executable commands for performing the steps of any method.

As used herein, a "culture condition" when used in reference to a cell refers to the state of a cell under a given set of conditions in a cell culture. Such a culture condition can be a condition of a cell culture or an in silico model of a cell in culture. A cell culture or tissue culture is understood by those skilled in the art to include an in vitro culture of a cell, in particular a cell culture of a eukarotic cell from a multicellular organism. Such an in vitro culture refers to the well known meaning of occurring outside an organism, although it is understood that such cells in culture are living cells. A culture condition can refer to the base state or steady state of a cell under a set of conditions or the state of a cell when such conditions are altered, either in an actual cell culture or in an in silico model of a cell culture. For example, a culture condition can refer to the state of a cell, in culture, as calculated based on the cell modeling methods, as disclosed herein. In addition, a culture condition can refer to the state of a cell under an altered set of conditions, for example, the state of a cell as calculated under the conditions of an optimized cell culture medium, optimized cell culture process, optimized cell productivity or after metabolic engineering, including any or all of these conditions as calculated using the in silico models as disclosed herein. Additional exemplary culture conditions include, but are not limited to, reduced scale up variability, reduced batch to batch variability, reduced clonal variability, improved cell growth, viable cell density or cell productivity in exponential growth phase or stationary phase. Such altered conditions can be included in a model or methods of producing such a model by applying an appropriate constraint set and objective function to achieve the desired result, as disclosed herein and as understood by those skilled in the art.

In a cell culture, it is understood that a nutrient is provided from the extracellular environment, generally in the culture media, although a nutrient can also be provided from a second cell in a co-culture if such a cell secretes a product that functions as a nutrient for the other cell in the co-culture. The components of a culture medium for providing nutrients to a cell in culture, either to maintain cell viability or cell growth, are well known to those skilled in the art. Such nutrients include, but are not limited to, carbon source, inorganic salts, metals, vitamins, amino acids, fatty acids, and the like (see, for example, Harrison and Rae, *General Techniques of Cell Culture*, chapter 3, pp. 31-59, Cambridge University Press, Cambridge United Kingdom (1997); Freshney, *Culture of Animal Cells: A Manual of Basic Technique* 4th ed., Wiley-Liss, (2000)). Such nutrients can be provided as a defined medium or supplemented with nutrient sources such as serum, as is well known to those skilled in the art. The culture medium generally includes carbohydrate as a source of carbon. Exemplary carbohydrates that can be used as a carbon source include, but are not limited to, sugars such as glucose, galactose, fructose, sucrose, and the like. It is understood that any nutrient that contains carbon and can be utilized by the cell in culture as a carbon source can be considered a nutrient that is a carbon source. Nutrients in the extracellular environment available to a cell include those substrates or products of an extracellular exchange reaction, including transport or transformation reactions. Thus, any reaction that allows transport or transformation of a nutrient in the extracellular environment for utilization inside the cell where the nutrient contains carbon is considered to be a nutrient that is a carbon source. Numerous commercial sources are available for various culture media.

"Exogenous" as it is used herein is intended to mean that the referenced molecule or the referenced activity is introduced into the host organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the host organism. When used in reference to a biosynthetic activity, the term refers to an activity that is introduced into the host reference organism. The source can be, for example, a homologous or heterologous encoding nucleic acid that expresses the referenced activity following introduction into the host organism. Therefore, the term "endogenous" refers to a referenced molecule or activity that is present in the host. Similarly, the term when used in reference to expression of an encoding nucleic acid refers to expression of an encoding nucleic acid contained within the organism. The term "heterologous" refers to a molecule or activity derived from a source other than the referenced species whereas "homologous" refers to a molecule or activity derived from the host organism. Accordingly, exogenous expression of an encoding nucleic acid can utilize either or both a heterologous or homologous encoding nucleic acid. Thus, it is understood that a desired product produced by a cell of the invention is an exogenous product, that is, a product introduced that is not normally expressed by the cell or having an increased level of expression relative to a native parental cell. Therefore, such a cell line has been engineered, either recombinantly or by selection, to have increased expression of a desired product, including but not limited to growth factors, monoclonal antibodies, hormones, cytokines, fusion proteins, enzymes, vaccines, viruses, anticoagulants, and nucleic acids. Such an increased expression can occur by recombinantly expressing a nucleic acid that is a desired product or a nucleic acid encoding a desired product. Alternatively, increased expression can occur by genetically modifying the cell to increase expression of a promoter and/or enhancer, either constitutively or by introducing an inducible promoter and/or enhancer.

As disclosed herein, the data structure can comprise a set of linear algebraic equations. In addition, the commands can comprise an optimization problem. In another embodiment, at least one reactant in the plurality of reactants or at least one reaction in the plurality of reactions can be annotated with an assignment to a subsystem or compartment. For example, a first substrate or product in the plurality of reactions can be assigned to a first compartment and a second substrate or product in the plurality of reactions can be assigned to a second compartment. Furthermore, at least a first substrate or product, or more substrates or products, in the plurality of reactions can be assigned to a first compartment and at least a second substrate or product, or more substrates or products, in the plurality of reactions can be assigned to a second compartment. In addition, a plurality of reactions can be annotated to indicate a plurality of associated genes and the gene database can comprise information characterizing the plurality of associated genes.

Methods for identifying a target selectable marker for a cell have been describe previously (WO 2010/098865, filed Feb. 26, 2010). As described previously and herein, the method can include the steps of providing a first data structure relating a plurality of reactants to a plurality of reactions from a cell, each of the reactions comprising a reactant identified as a substrate of the reaction, a reactant identified as a product of the reaction and a stoichiometric coefficient relating the substrate and the product, wherein the plurality of reactions comprises one or more extracellular exchange reactions; providing a constraint set for the plurality of reactions for the first data structure; providing an objective function, wherein the objective function is uptake rate of two or more nutrients, wherein the two or more nutrients are carbon sources; determining at least one flux distribution that minimizes or maximizes the objective function when the constraint set is applied to the data structure; deleting a reaction from the data structure to generate a second data structure and repeating steps of providing a constraint set, providing an objective function and determining at least one flux distribution as discussed above; optionally repeating the deleting step by deleting a different reaction, wherein the at least one flux distribution determined with the second data structure is predictive of a reaction required for cell growth or cell viability, thereby identifying a target selectable marker reaction or reactant. Such a method can further comprise providing the second data structure; providing one or more extracellular substrates or products corresponding to one or more reactions of the one or more extracellular exchange reactions to the second data structure to generate a third data structure; providing a constraint set for the plurality of reactions for the third data structure; providing an objective function, wherein the objective function is cell viability or growth; and determining at least one flux distribution that minimizes or maximizes the objective function when the constraint set is applied to the third data structure, wherein the at least one flux distribution determined with the third data structure is predictive of an extracellular substrate or product that complements the target selectable marker reaction or reactant, thereby identifying a selectable marker reaction or reactant. In such a method, the objective function can further comprise uptake rate of the one or more extracellular substrates or products. Such a model can be provided, for example, on a computer readable medium or media having stored thereon computer executable commands for performing the steps of the method.

As used herein, a "selectable marker" is well known to those skilled in molecular biology and refers to a gene whose expression allows the identification of cells that have been transformed or transfected with a vector containing the marker gene, that is, the presence or absence of the gene (selectable marker) can be selected for, generally based on an altered growth or cell viability characteristic of the cell. Well known exemplary selectable markers used routinely in cell culture include, for example, the dihydrofolate reductase (DHFR) and glutamine synthetase (GS) selection systems (see Ausubel et al., *Current Protocols in Molecular Biology*, John Wiley and Sons, Baltimore, Md. (1999)). The modeling methods allow the identification of target selectable markers by using in silico models of a cell to identify a reaction that is required for cell viability or cell growth, that is, an essential reaction. Generally, selectable markers are utilized such that a cell will either die in the absence of a product produced by the selectable marker or will not grow, either case of which will prevent a cell lacking a complementary product from growing. The modeling methods are based on deleting a reaction from a data structure containing a plurality of reactions and determining whether the deletion has an effect on cell viability or growth. If the deletion results in no cell growth or in cell death, then the deleted reaction is a target selectable marker. The method can be used to determine any of a number of target selectable markers by optionally repeating deleting different reactions. Generally, a single reaction is deleted to test for the effect on cell growth or viability, although multiple reactions can be deleted, if desired. In general, if a reaction is deleted from a data structure and the deletion has no effect on cell growth or viability, then a different reaction is deleted from the data structure and tested for its effect on cell growth or viability. Accordingly, in such a method, the data structure generally has only one reaction deleted at a time to test for the effect on cell growth or viability. As used herein, inhibiting cell growth generally includes preventing cell division or slowing the rate of cell division so that the doubling time of the cell is substantially reduced, for example, at least 2-fold, 3-fold, 4-fold, 5-fold, 10-fold, or even further reduction in doubling time, so long as the difference in growth rate from a cell containing the selectable marker is sufficient to differentiate the presence or absence of the selectable marker.

After identifying a target selectable marker reaction or reactant, the deleted data structure that identifies a reaction or reactant required for cell growth or viability can be tested for the ability to support cell growth or viability by the addition of an extracellular reaction to the data structure that complements the deleted reaction. For example, if a reaction is deleted and the deletion results in cell death or no cell growth, the product of that reaction can be used to complement the missing reaction and cause the cell to resume cell growth or viability. To be particularly useful as a selectable marker and selection system, it is desirable to be able to complement the missing reaction by addition of a component to the cell culture medium. Therefore, for a deleted reaction to be useful as a selectable marker, the deleted product must either be provided in the culture medium and transported into the cell or a precursor of the product transported into the cell and either transformed or converted to the missing product. To test for this possibility, one or more extracellular exchange reactions, which could potentially result in transport of the deleted product or a precursor of the product, is added to the data structure with the deleted reaction, and the cell is tested for whether cell growth or viability is recovered or resumed. If cell growth and viability is recovered with the addition of the extracellular substrate or product that can be transported, transformed or converted into the product intracellularly, then the deleted reaction and the complementary extracellular product or substrate can function as a selectable marker system. As used herein, a substrate or product that "complements" a target selectable marker refers to a substrate or product that, when added to a cell culture (in vitro or in silico), allows a cell having a deleted reaction (target selectable marker) required for cell growth or cell viability to restore cell growth or viability to the cell. Thus, the methods of the invention can be used to identify target selectable marker reactions or reactants and a selectable marker reaction or reactant with a complementary substrate or product that restores cell growth or viability.

Thus, the methods can be utilized for predicting a physiological function of a cell by providing a data structure relating a plurality of reactants to a plurality of reactions from a cell, each of the reactions comprising a reactant identified as a substrate of the reaction, a reactant identified as a product of the reaction and a stoichiometric coefficient relating the substrate and the product; providing a constraint set for the plurality of reactions for the data structures; providing an objective function, and determining at least one flux distribution that minimizes or maximizes an objective function when the constraint set is applied to the data structure, wherein the objective function identifies a target selectable marker reaction or reactant and wherein the at least one flux distribution is predictive of a physiological function of the cell.

As used herein, a "selection of reactants and reactions" when used with reference to a model of the invention means that a suitable number of the reactions and reactants, including up to all the reactions and reactants, can be selected from a list of reactions for use of the model. For example, any and up to all the reactions as shown in Tables 21-23 can be a selection of reactants and reactions, so long as the selected reactions are sufficient to provide an in silico model suitable for a desired purpose, such as those disclosed herein. It is understood that, if desired, a selection of reactions can include a net reaction between more than one of the individual reactions shown in Table 4. For example, if reaction 1 converts substrate A to product B, and reaction 2 converts substrate B to product C, a net reaction of the conversion of substrate A to product C can be used in the selection of reactions and reactants for use of a model of the invention. One skilled in the art will recognize that such a net reaction conserves stoichiometry between the conversion of A to B to C or A to C and will therefore satisfy the requirements for utilizing the model.

The reactants to be used in a reaction network data structure can be obtained from or stored in a compound database. As used herein, the term "compound database" is intended to mean a computer readable medium or media containing a plurality of molecules that includes substrates and products of biological reactions. The plurality of molecules can include molecules found in multiple organisms or cell types, thereby constituting a universal compound database. Alternatively, the plurality of molecules can be limited to those that occur in a particular organism or cell type, thereby constituting an organism-specific or cell type-specific compound database. Each reactant in a compound database can be identified according to the chemical species and the cellular compartment in which it is present. Thus, for example, a distinction can be made between glucose in the extracellular compartment versus glucose in the cytosol. Additionally each of the reactants can be specified as a metabolite of a primary or secondary metabolic pathway. Although identification of a reactant as a metabolite of a primary or secondary metabolic pathway does not indicate any chemical distinction between the reactants in a reaction, such a designation can assist in visual representations of large networks of reactions.

As used herein, the term "compartment" is intended to mean a subdivided region containing at least one reactant, such that the reactant is separated from at least one other reactant in a second region. A subdivided region included in the term can be correlated with a subdivided region of a cell. Thus, a subdivided region included in the term can be, for example, the intracellular space of a cell; the extracellular space around a cell; the interior space of an organelle such as a mitochondrium, endoplasmic reticulum, Golgi apparatus, vacuole or nucleus; or any subcellular space that is separated from another by a membrane or other physical barrier. For example, a mitochondrial compartment is a subdivided region of the intracellular space of a cell, which in turn, is a subdivided region of a cell or tissue. A subdivided region also can include, for example, different regions or systems of a tissue, organ or physiological system of an organism. Subdivided regions can also be made in order to create virtual boundaries in a reaction network that are not correlated with physical barriers. Virtual boundaries can be made for the purpose of segmenting the reactions in a network into different compartments or substructures.

As used herein, the term "substructure" is intended to mean a portion of the information in a data structure that is separated from other information in the data structure such that the portion of information can be separately manipulated or analyzed. The term can include portions subdivided according to a biological function including, for example, information relevant to a particular metabolic pathway such as an internal flux pathway, exchange flux pathway, central metabolic pathway, peripheral metabolic pathway, or secondary metabolic pathway. The term can include portions subdivided according to computational or mathematical principles that allow for a particular type of analysis or manipulation of the data structure.

The reactions included in a reaction network data structure can be obtained from a metabolic reaction database that includes the substrates, products, and stoichiometry of a plurality of metabolic reactions of a cell line that exhibit biochemical or physiological interactions. The reactants in a reaction network data structure can be designated as either substrates or products of a particular reaction, each with a stoichiometric coefficient assigned to it to describe the chemical conversion taking place in the reaction. Each reaction is also described as occurring in either a reversible or irreversible direction. Reversible reactions can either be represented as one reaction that operates in both the forward and reverse direction or be decomposed into two irreversible reactions, one corresponding to the forward reaction and the other corresponding to the backward reaction.

Reactions included in a reaction network data structure can include intra-system or exchange reactions. Intra-system reactions are the chemically and electrically balanced inter-conversions of chemical species and transport processes, which serve to replenish or drain the relative amounts of certain metabolites. These intra-system reactions can be classified as either being transformations or translocations. A transformation is a reaction that contains distinct sets of compounds as substrates and products, while a translocation contains reactants located in different compartments. Thus a reaction that simply transports a metabolite from the extracellular environment to the cytosol, without changing its chemical composition is solely classified as a translocation, while a reaction that takes an extracellular substrate and converts it into a cytosolic product is both a translocation and a transformation. Further, intra-system reactions can include reactions representing one or more biochemical or physiological functions of an independent cell, tissue, organ or physiological system. An "extracellular exchange reaction" as used herein refers in particular to those reactions that traverse the cell membrane and exchange substrates and products between the extracellular environment and intracellular environment of a cell. Such extracellular exchange reactions include, for example, translocation and transformation reactions between the extracellular environment and intracellular environment of a cell.

Exchange reactions are those which constitute sources and sinks, allowing the passage of metabolites into and out of a compartment or across a hypothetical system boundary. These reactions are included in a model for simulation purposes and represent the metabolic demands placed a cell. While they may be chemically balanced in certain cases, they are typically not balanced and can often have only a single substrate or product. As a matter of convention the exchange reactions are further classified into demand exchange and input/output exchange reactions.

The metabolic demands placed on a cell metabolic reaction network can be readily determined from the dry weight composition of the cell, which is available in the published literature or which can be determined experimentally. The uptake rates and maintenance requirements for a cell line can also be obtained from the published literature or determined experimentally.

Input/output exchange reactions are used to allow extracellular reactants to enter or exit the reaction network represented by a model. For each of the extracellular metabolites a corresponding input/output exchange reaction can be created. These reactions are always reversible with the metabolite indicated as a substrate with a stoichiometric coefficient of one and no products produced by the reaction. This particular convention is adopted to allow the reaction to take on a positive flux value (activity level) when the metabolite is being produced or removed from the reaction network and a negative flux value when the metabolite is being consumed or introduced into the reaction network. These reactions will be further constrained during the course of a simulation to specify exactly which metabolites are available to the cell and which can be excreted by the cell.

A demand exchange reaction is always specified as an irreversible reaction containing at least one substrate. These reactions are typically formulated to represent the production of an intracellular metabolite by the metabolic network or the aggregate production of many reactants in balanced ratios such as in the representation of a reaction that leads to biomass formation, also referred to as growth.

A demand exchange reactions can be introduced for any metabolite in a model. Most commonly these reactions are introduced for metabolites that are required to be produced by the cell for the purposes of creating a new cell such as amino acids, nucleotides, phospholipids, and other biomass constituents, or metabolites that are to be produced for alternative purposes. Once these metabolites are identified, a demand exchange reaction that is irreversible and specifies the metabolite as a substrate with a stoichiometric coefficient of unity can be created. With these specifications, if the reaction is active it leads to the net production of the metabolite by the system meeting potential production demands. Examples of processes that can be represented as a demand exchange reaction in a reaction network data structure and analyzed by the methods include, for example, production or secretion of an individual protein; production or secretion of an individual metabolite such as an amino acid, vitamin, nucleoside, antibiotic or surfactant; production of ATP for extraneous energy requiring processes such as locomotion or muscle contraction; or formation of biomass constituents.

In addition to these demand exchange reactions that are placed on individual metabolites, demand exchange reactions that utilize multiple metabolites in defined stoichiometric ratios can be introduced. These reactions are referred to as aggregate demand exchange reactions. An example of an aggregate demand reaction is a reaction used to simulate the concurrent growth demands or production requirements associated with cell growth that are placed on a cell, for example, by simulating the formation of multiple biomass constituents simultaneously at a particular cellular growth rate.

Constraint-based modeling can be used to model and predict cellular behavior in reconstructed networks. In order to analyze, interpret, and predict cellular behavior using approaches other than the constraint-based modeling approach, each individual step in a biochemical network is described, normally with a rate equation that requires a number of kinetic constants. However, it is currently not possible to formulate this level of description of cellular processes on a genome scale. The kinetic parameters cannot be estimated from the genome sequence, and these parameters are not available in the literature in the abundance required for accurate modeling. In the absence of kinetic information, it is still possible to assess the capabilities and performance of integrated cellular processes and incorporate data that can be used to constrain these capabilities.

To accomplish suitable modeling, a constraint-based approach for modeling can be implemented. Rather than attempting to calculate and predict exactly what a metabolic network does, the range of possible phenotypes that a metabolic system can display is narrowed based on the successive imposition of governing physico-chemical constraints (Palsson, *Nat. Biotechnol.* 18:1147-1150 (2000)). Thus, instead of calculating an exact phenotypic solution, that is, exactly how the cell behaves under given genetic and environmental conditions, the feasible set of phenotypic solutions in which the cell can operate is determined.

Such a constraint-based approach provides a basis for understanding the structure and function of biochemical networks through an incremental process. This incremental refinement presently occurs in the following four steps, each of which involves consideration of fundamentally different constraints: (1) the imposition of stoichiometric constraints that represent flux balances; (2) the utilization of limited thermodynamic constraints to restrict the directional flow through enzymatic reactions; (3) the addition of capacity constraints to account for the maximum flux through individual reactions; and (4) the imposition of regulatory constraints, where available.

Each step provides increasing amounts of information that can be used to further reduce the range of feasible flux distributions and phenotypes that a metabolic network can display. Each of these constraints can be described mathematically, offering a concise geometric interpretation of the effects that each successive constraint places on metabolic function. In combination with linear programming, constraint-based modeling has been used to represent probable physiological functions such as biomass and ATP production. Constraint-based modeling approaches have been reviewed in detail (Schilling et al., *Biotechnol. Prog.* 15:288-295 (1999); Varma and Palsson, *Bio/Technology* 12:994-998 (1994); Edwards et al., *Environ. Microbiol.* 4:133-140 (2002); Price et al., *Nat. Rev. Microbiol.* 2:886-897 (2004)).

Transient flux balance analysis can also be used. A number of computational modeling methods have been developed based on the basic premise of the constraint-based approach, including the transient flux balance analysis (Varma and Palsson, *Appl. Environ. Microbiol.* 60:3724-3731 (1994); Price et al., *Nat. Rev. Microbiol.* 2:886-897 (2004)). Transient flux balance analysis is a well-established approach for computing the time profile of consumed and secreted metabolites in a bioreactor, predicted based on the computed values from a steady state constraint-based metabolic model (Covert et al., *J. Theor. Biol.* 213:73-88 (2001)); Varma and Palsson, *Appl. Environ. Microbiol.* 60:3724-3731 (1994); Covert and Palsson, *J. Biol. Chem.* 277:28058-28064 (2002)). This approach has been successfully used to predict growth and metabolic byproduct secretion in wild-type *E. coli* in aerobic and anaerobic batch and fed-batch bioreactors, and to improve the predictability of the metabolic models using transcriptional regulatory constraints (Varma and Palsson, supra, 2004; Covert and Palsson, supra, 2002).

Briefly, a time profile of metabolite concentrations is calculated by the transient flux balance analysis in an iterative two-step process, where: (1) uptake and secretion rate of metabolites are determined using a metabolic network and linear optimization, and (2) the metabolite concentrations in the bioreactor are calculated using the dynamic mass balance equation. A set of uptake rates of nutrients can be used to constrain the flux balance calculation in the metabolic network. Using linear optimization, an intracellular flux distribution is calculated and metabolite secretion rates are determined in the metabolic network. The calculated secretion rates are then used to determine the concentration of metabolites in the bioreactor media using the standard dynamic mass balance equations, $$S - S_o = q_s \int X_v dt \qquad \text{Equation (1)},$$

where S is a consumed nutrient or produced metabolite concentration, $S_o$ is the initial or previous time point metabolite concentration, and $X_v$ is the viable cell concentration. Cell specific growth rate is computed using standard growth equation, $$X_v = X_{v,o} e^{\mu t} \qquad \text{Equation (2)},$$

where $X_{v,o}$ is the initial cell concentration and $\mu$ is cell specific growth rate. This procedure is repeated in small arbitrary time intervals for the duration of bioreactor or cell culture experiment from which a time profile of metabolite and cell concentration can be graphically displayed. Transient analysis can thus estimate the time profile of the metabolite concentrations and determine the duration of the cell culture, that is, when the cells run out of nutrients and growth of the cell culture ceases.

The SimPheny™ method or similar modeling method can also be used (see U.S. publication 2003/0233218). Exemplary modeling methods are also described in U.S. publications 2004/0029149 and 2006/0147899. Improving the efficiency of biological discovery and delivering on the potential of model-driven systems biology requires the development of a computational infrastructure to support collaborative model development, simulation, and data integration/management. In addition, such a high performance-computing platform should embrace the iterative nature of modeling and simulation to allow the value of a model to increase in time as more information is incorporated. One such modeling method is called SimPheny™, short for Simulating Phenotypes, which allows the integration of simulation based systems biology for solving complex biological problems. SimPheny™ was developed to support multi-user research in concentrated or distributed environments to allow effective collaboration. It serves as the basis for a model-centric approach to biological discovery. The SimPheny™ method has been described previously (see U.S. publication 2003/0233218; WO03106998).

The SimPheny™ method allows the modeling of biochemical reaction networks and metabolism in organism-specific models. The platform supports the development of metabolic models, all of the necessary simulation activities, and the capability to integrate various experimental data. The system is divided into a number of discrete modules to support various activities associated with modeling and simulation. The modules include: (1) universal data, (2) model development, (3) atlas design, (4) simulation, (5) content mining, (6) experimental data analysis, and (7) pathway predictor.

Each of these modules encapsulates activities that are crucial to supporting the iterative model development process. They are all fully integrated with each other so that information created in one module can be utilized where appropriate in other modules. Within the universal data module, all of the data concerning chemical compounds, reactions, and organisms is maintained, providing the underlying information required for constructing cellular models. The model-development module is used to create a model and assign all the appropriate reactions to a model along with specifying any related information such as the genetic associations and reference information related to the reaction in the model and the model in general. The atlas design module is used to design metabolic maps and organize them into collections or maps (an atlas). Models are used to simulate the phenotypic behavior of an organism under changing genetic circumstances and environmental conditions. These simulations are performed within the simulation module that enables the use of optimization strategies to calculate cellular behavior. In addition to calculated simulation results, this module allows for the viewing of results in a wide variety of contexts. In order to browse and mine the biological content of all the models and associated genomics for the model organisms, a separate module for data mining can be used. Thus, SimPheny™ represents an exemplary tool that provides the power of modeling and simulation within a systems biology research strategy.

The representation of a reaction network with a set of linear algebraic equations presented as a stoichiometric matrix has been described (U.S. publication 2006/0147899). A reaction network can be represented as a set of linear algebraic equations which can be presented as a stoichiometric matrix S, with S being an m×n matrix where m corresponds to the number of reactants or metabolites and n corresponds to the number of reactions taking place in the network. Each column in the matrix corresponds to a particular reaction n, each row corresponds to a particular reactant m, and each $S_{mn}$ element corresponds to the stoichiometric coefficient of the reactant m in the reaction denoted n. The stoichiometric matrix can include intra-system reactions which are related to reactants that participate in the respective reactions according to a stoichiometric coefficient having a sign indicative of whether the reactant is a substrate or product of the reaction and a value correlated with the number of equivalents of the reactant consumed or produced by the reaction. Exchange reactions are similarly correlated with a stoichiometric coefficient. The same compound can be treated separately as an internal reactant and an external reactant such that an exchange reaction exporting the compound is correlated by stoichiometric coefficients of −1 and 1, respectively. However, because the compound is treated as a separate reactant by virtue of its compartmental location, a reaction which produces the internal reactant but does not act on the external reactant is correlated by stoichiometric coefficients of 1 and 0, respectively. Demand reactions such as growth can also be included in the stoichiometric matrix being correlated with substrates by an appropriate stoichiometric coefficient.

As disclosed herein, a stoichiometric matrix provides a convenient format for representing and analyzing a reaction network because it can be readily manipulated and used to compute network properties, for example, by using linear programming or general convex analysis. A reaction network data structure can take on a variety of formats so long as it is capable of relating reactants and reactions in the manner exemplified herein for a stoichiometric matrix and in a manner that can be manipulated to determine an activity of one or more reactions using methods such as those exemplified herein. Other examples of reaction network data structures that are useful in the invention include a connected graph, list of chemical reactions or a table of reaction equations.

A reaction network data structure can be constructed to include all reactions that are involved in metabolism occurring in a cell line or any portion thereof. A portion of an cell's metabolic reactions that can be included in a reaction network data structure includes, for example, a central metabolic pathway such as glycolysis, the TCA cycle, the PPP or ETS; or a peripheral metabolic pathway such as amino acid biosynthesis, amino acid degradation, purine biosynthesis, pyrimidine biosynthesis, lipid biosynthesis, fatty acid metabolism, vitamin or cofactor biosynthesis, transport processes and alternative carbon source catabolism. Other examples of portions of metabolic reactions that can be included in a reaction network data structure include, for example, TAG biosynthesis, muscle contraction requirements, bicarbonate buffer system and/or ammonia buffer system. Specific examples of these and other reactions are described further below and in the Examples. Depending upon a particular application, a reaction network data structure can include a plurality of reactions including any or all of the reactions known in a cell or organism.

For some applications, it can be advantageous to use a reaction network data structure that includes a minimal number of reactions to achieve a particular activity under a particular set of environmental conditions. A reaction network data structure having a minimal number of reactions can be identified by performing the simulation methods described below in an iterative fashion where different reactions or sets of reactions are systematically removed and the effects observed. Accordingly, the invention provides a computer readable medium, containing a data structure relating a plurality of reactants to a plurality of reactions.

Depending upon the particular cell type, the physiological conditions being tested, and the desired activity of a model or method, a reaction network data structure can contain smaller numbers of reactions such as at least 200, 150, 100 or 50 reactions. A reaction network data structure having relatively few reactions can provide the advantage of reducing computation time and resources required to perform a simulation. When desired, a reaction network data structure having a particular subset of reactions can be made or used in which reactions that are not relevant to the particular simulation are omitted. Alternatively, larger numbers of reactions can be included in order to increase the accuracy or molecular detail of the methods or to suit a particular application. Thus, a reaction network data structure can contain at least 300, 350, 400, 450, 500, 550, 600 or more reactions up to the number of reactions that occur in a cell or organism or that are desired to simulate the activity of the full set of reactions occurring in a cell or organism. A reaction network data structure that is substantially complete with respect to the metabolic reactions of a cell or organism provides an advantage of being relevant to a wide range of conditions to be simulated, whereas those with smaller numbers of metabolic reactions are specific to a particular subset of conditions to be simulated.

A reaction network data structure can include one or more reactions that occur in or by a cell or organism and that do not occur, either naturally or following manipulation, in or by another organism. It is understood that a reaction network data structure of a particular cell type can also include one or more reactions that occur in another cell type. Addition of such heterologous reactions to a reaction network data structure can be used in methods to predict the consequences of heterologous gene transfer and protein expression.

The reactions included in a reaction network data structure can be metabolic reactions. A reaction network data structure can also be constructed to include other types of reactions such as regulatory reactions, signal transduction reactions, cell cycle reactions, reactions involved in apoptosis, reactions involved in responses to hypoxia, reactions involved in responses to cell-cell or cell-substrate interactions, reactions involved in protein synthesis and regulation thereof, reactions involved in gene transcription and translation, and regulation thereof, and reactions involved in assembly of a cell and its subcellular components.

A reaction network data structure or index of reactions used in the data structure such as that available in a metabolic reaction database, as described above, can be annotated to include information about a particular reaction. A reaction can be annotated to indicate, for example, assignment of the reaction to a protein, macromolecule or enzyme that performs the reaction, assignment of a gene(s) that codes for the protein, macromolecule or enzyme, the Enzyme Commission (EC) number of the particular metabolic reaction, a subset of reactions to which the reaction belongs, citations to references from which information was obtained, or a level of confidence with which a reaction is believed to occur in a cell or organism. A computer readable medium or media can include a gene database containing annotated reactions. Such information can be obtained during the course of building a metabolic reaction database or model as described below.

As used herein, the term "gene database" is intended to mean a computer readable medium or media that contains at least one reaction that is annotated to assign a reaction to one or more macromolecules that perform the reaction or to assign one or more nucleic acid that encodes the one or more macromolecules that perform the reaction. A gene database can contain a plurality of reactions, some or all of which are annotated. An annotation can include, for example, a name for a macromolecule; assignment of a function to a macromolecule; assignment of an organism that contains the macromolecule or produces the macromolecule; assignment of a subcellular location for the macromolecule; assignment of conditions under which a macromolecule is regulated with respect to performing a reaction, being expressed or being degraded; assignment of a cellular component that regulates a macromolecule; an amino acid or nucleotide sequence for the macromolecule; an mRNA isoform, enzyme isoform, or any other desirable annotation or annotation found for a macromolecule in a genome database such as those that can be found in Genbank, a site maintained by the NCBI (ncbi.nlm.gov), the Kyoto Encyclopedia of Genes and Genomes (KEGG) (www.genome.ad.jp/kegg/), the protein database SWISS-PROT (ca.expasy.org/sprot/), the LocusLink database maintained by the NCBI (www.ncbi.nlm.nih.gov/LocusLink/), the Enzyme Nomenclature database maintained by G. P. Moss of Queen Mary and Westfield College in the United Kingdom (www.chem.qmw.ac.uk/iubmb/enzyme/).

A gene database can include a substantially complete collection of genes or open reading frames in a cell or organism, substantially complete collection of the macromolecules encoded by the cell's or organism's genome. Alternatively, a gene database can include a portion of genes or open reading frames in an organism or a portion of the macromolecules encoded by the organism's genome, such as the portion that includes substantially all metabolic genes or macromolecules. The portion can be at least 10%, 15%, 20%, 25%, 50%, 75%, 90% or 95% of the genes or open reading frames encoded by the organism's genome, or the macromolecules encoded therein. A gene database can also include macromolecules encoded by at least a portion of the nucleotide sequence for the organism's genome such as at least 10%, 15%, 20%, 25%, 50%, 75%, 90% or 95% of the organism's genome. Accordingly, a computer readable medium or media can include at least one reaction for each macromolecule encoded by a portion of a cell or organism's genome.

An in silico model of cell of the invention can be built by an iterative process which includes gathering information regarding particular reactions to be added to a model, representing the reactions in a reaction network data structure, and performing preliminary simulations wherein a set of constraints is placed on the reaction network and the output evaluated to identify errors in the network. Errors in the network such as gaps that lead to non-natural accumulation or consumption of a particular metabolite can be identified as described below and simulations repeated until a desired performance of the model is attained. Combination of the central metabolism and the cell specific reaction networks into a single model produces, for example, a cell specific reaction network.

Information to be included in a data structure can be gathered from a variety of sources including, for example, annotated genome sequence information and biochemical literature. Sources of annotated human genome sequence information include, for example, KEGG, SWISS-PROT, LocusLink, the Enzyme Nomenclature database, the International Human Genome Sequencing Consortium and commercial databases. KEGG contains a broad range of information, including a substantial amount of metabolic reconstruction. The genomes of 304 organisms can be accessed here, with gene products grouped by coordinated functions, often represented by a map (e.g., the enzymes involved in glycolysis would be grouped together). The maps are biochemical pathway templates which show enzymes connecting metabolites for various parts of metabolism. These general pathway templates are customized for a given organism by highlighting enzymes on a given template which have been identified in the genome of the organism. Enzymes and metabolites are active and yield useful information about stoichiometry, structure, alternative names and the like, when accessed.

SWISS-PROT contains detailed information about protein function. Accessible information includes alternate gene and gene product names, function, structure and sequence information, relevant literature references, and the like. LocusLink contains general information about the locus where the gene is located and, of relevance, tissue specificity, cellular location, and implication of the gene product in various disease states.

The Enzyme Nomenclature database can be used to compare the gene products of two organisms. Often the gene names for genes with similar functions in two or more organisms are unrelated. When this is the case, the E.C. (Enzyme Commission) numbers can be used as unambiguous indicators of gene product function. The information in the Enzyme Nomenclature database is also published in Enzyme Nomenclature (Academic Press, San Diego, Calif., 1992) with 5 supplements to date, all found in the European Journal of Biochemistry (Blackwell Science, Malden, Mass.).

Sources of biochemical information include, for example, general resources relating to metabolism, resources relating specifically to a particular cell's or organism's metabolism, and resources relating to the biochemistry, physiology and pathology of specific cell types.

Sources of general information relating to metabolism, which can be used to generate human reaction databases and models, include J. G. Salway, *Metabolism at a Glance*, $2^{nd}$ ed., Blackwell Science, Malden, Mass. (1999) and T. M. Devlin, ed., *Textbook of Biochemistry with Clinical Correlations*, $4^{th}$ ed., John Wiley and Sons, New York, N.Y. (1997). Human metabolism-specific resources include J. R. Bronk, *Human Metabolism: Functional Diversity and Integration*, Addison Wesley Longman, Essex, England (1999).

In the course of developing an in silico model of metabolism, the types of data that can be considered include, for example, biochemical information which is information related to the experimental characterization of a chemical reaction, often directly indicating a protein(s) associated with a reaction and the stoichiometry of the reaction or indirectly demonstrating the existence of a reaction occurring within a cellular extract; genetic information, which is information related to the experimental identification and genetic characterization of a gene(s) shown to code for a particular protein(s) implicated in carrying out a biochemical event; genomic information, which is information related to the identification of an open reading frame and functional assignment, through computational sequence analysis, that is then linked to a protein performing a biochemical event; physiological information, which is information related to overall cellular physiology, fitness characteristics, substrate utilization, and phenotyping results, which provide evidence of the assimilation or dissimulation of a compound used to infer the presence of specific biochemical event (in particular translocations); and modeling information, which is information generated through the course of simulating activity of cells, tissues or physiological systems using methods such as those described herein which lead to predictions regarding the status of a reaction such as whether or not the reaction is required to fulfill certain demands placed on a metabolic network. Additional information that can be considered includes, for example, cell type-specific or condition-specific gene expression information, which can be determined experimentally, such as by gene array analysis or from expressed sequence tag (EST) analysis, or obtained from the biochemical and physiological literature.

The majority of the reactions occurring in a cell's or organism's reaction networks are catalyzed by enzymes/proteins, which are created through the transcription and translation of the genes found within the chromosome in the cell. The remaining reactions occur either spontaneously or through non-enzymatic processes. Furthermore, a reaction network data structure can contain reactions that add or delete steps to or from a particular reaction pathway. For example, reactions can be added to optimize or improve performance of a model for multicellular interactions in view of empirically observed activity. Alternatively, reactions can be deleted to remove intermediate steps in a pathway when the intermediate steps are not necessary to model flux through the pathway. For example, if a pathway contains 3 nonbranched steps, the reactions can be combined or added together to give a net reaction, thereby reducing memory required to store the reaction network data structure and the computational resources required for manipulation of the data structure.

The reactions that occur due to the activity of gene-encoded enzymes can be obtained from a genome database which lists genes identified from genome sequencing and subsequent genome annotation. Genome annotation consists of the locations of open reading frames and assignment of function from homology to other known genes or empirically determined activity. Such a genome database can be acquired through public or private databases containing annotated nucleic acid or protein sequences. If desired, a model developer can perform a network reconstruction and establish the model content associations between the genes, proteins, and reactions as described, for example, in Covert et al. *Trends in Biochemical Sciences* 26:179-186 (2001) and Palsson, WO 00/46405.

As reactions are added to a reaction network data structure or metabolic reaction database, those having known or putative associations to the proteins/enzymes which allow/catalyze the reaction and the associated genes that code for these proteins can be identified by annotation. Accordingly, the appropriate associations for all of the reactions to their related proteins or genes or both can be assigned. These associations can be used to capture the non-linear relationship between the genes and proteins as well as between proteins and reactions. In some cases one gene codes for one protein which then perform one reaction. However, often there are multiple genes which are required to create an active enzyme complex and often there are multiple reactions that can be carried out by one protein or multiple proteins that can carry out the same reaction. These associations capture the logic (i.e. AND or OR relationships) within the associations Annotating a metabolic reaction database with these associations can allow the methods to be used to determine the effects of adding or eliminating a particular reaction not only at the reaction level, but at the genetic or protein level in the context of running a simulation or predicting an activity.

A reaction network data structure can be used to determine the activity of one or more reactions in a plurality of reactions occurring in a cell independent of any knowledge or annotation of the identity of the protein that performs the reaction or the gene encoding the protein. A model that is annotated with gene or protein identities can include reactions for which a protein or encoding gene is not assigned. While a large portion of the reactions in a cellular metabolic network are associated with genes in the organism's genome, there are also a substantial number of reactions included in a model for which there are no known genetic associations. Such reactions can be added to a reaction database based upon other information that is not necessarily related to genetics such as biochemical or cell based measurements or theoretical considerations based on observed biochemical or cellular activity. For example, there are many reactions that can either occur spontaneously or are not protein-enabled reactions. Furthermore, the occurrence of a particular reaction in a cell for which no associated proteins or genetics have been currently identified can be indicated during the course of model building by the iterative model building methods.

The reactions in a reaction network data structure or reaction database can be assigned to subsystems by annotation, if desired. The reactions can be subdivided according to biological criteria, such as according to traditionally identified metabolic pathways (glycolysis, amino acid metabolism and the like) or according to mathematical or computational criteria that facilitate manipulation of a model that incorporates or manipulates the reactions. Methods and criteria for subdividing a reaction database are described in further detail in Schilling et al., *J. Theor. Biol.* 203:249-283 (2000), and in Schuster et al., *Bioinformatics* 18:351-361 (2002). The use of subsystems can be advantageous for a number of analysis methods, such as extreme pathway analysis, and can make the management of model content easier. Although assigning reactions to subsystems can be achieved without affecting the use of the entire model for simulation, assigning reactions to subsystems can allow a user to search for reactions in a particular subsystem which may be useful in performing various types of analyses. Therefore, a reaction network data structure can include any number of desired subsystems including, for example, 2 or more subsystems, 5 or more subsystems, 10 or more subsystems, 25 or more subsystems or 50 or more subsystems.

The reactions in a reaction network data structure or metabolic reaction database can be annotated with a value indicating the confidence with which the reaction is believed to occur in a cell or organism. The level of confidence can be, for example, a function of the amount and form of supporting data that is available. This data can come in various forms including published literature, documented experimental results, or results of computational analyses. Furthermore, the data can provide direct or indirect evidence for the existence of a chemical reaction in a cell based on genetic, biochemical, and/or physiological data.

Constraints can be placed on the value of any of the fluxes in the metabolic network using a constraint set. These constraints can be representative of a minimum or maximum allowable flux through a given reaction, possibly resulting from a limited amount of an enzyme present. Additionally, the constraints can determine the direction or reversibility of any of the reactions or transport fluxes in the reaction network data structure. Based on the in vivo environment where multiple cells interact, such as in a human organism, the metabolic resources available to the cell for biosynthesis of essential molecules can be determined.

As described previously (see U.S. publication 2006/014789), for a reaction network, constraints can be placed on each reaction, with the constraints provided in a format that can be used to constrain the reactions of a stoichiometric matrix. The format for the constraints used for a matrix or in linear programming can be conveniently represented as a linear inequality such as $$b_j \leq v_j \leq a_j; j=1 \ldots n \qquad \text{(Eq. 3)}$$

where $v_j$ is the metabolic flux vector, $b_j$ is the minimum flux value and $a_j$ is the maximum flux value. Thus, $a_j$ can take on a finite value representing a maximum allowable flux through a given reaction or $b_j$ can take on a finite value representing minimum allowable flux through a given reaction. Additionally, if one chooses to leave certain reversible reactions or transport fluxes to operate in a forward and reverse manner the flux may remain unconstrained by setting $b_j$ to negative infinity and $a_j$ to positive infinity. If reactions proceed only in the forward reaction, $b_j$ is set to zero while $a_j$ is set to positive infinity. As an example, to simulate the event of a genetic deletion or non-expression of a particular protein, the flux through all of the corresponding metabolic reactions related to the gene or protein in question are reduced to zero by setting $a_j$ and $b_j$ to be zero. Furthermore, if one wishes to simulate the absence of a particular growth substrate one can simply constrain the corresponding transport fluxes that allow the metabolite to enter the cell to be zero by setting $a_j$ and $b_j$ to be zero. On the other hand, if a substrate is only allowed to enter or exit the cell via transport mechanisms, the corresponding fluxes can be properly constrained to reflect this scenario.

The ability of a reaction to be actively occurring is dependent on a large number of additional factors beyond just the availability of substrates. These factors, which can be represented as variable constraints in the models and methods include, for example, the presence of cofactors necessary to stabilize the protein/enzyme, the presence or absence of enzymatic inhibition and activation factors, the active formation of the protein/enzyme through translation of the corresponding mRNA transcript, the transcription of the associated gene(s) or the presence of chemical signals and/or proteins that assist in controlling these processes that ultimately determine whether a chemical reaction is capable of being carried out within an organism. Regulation can be represented in an in silico model by providing a variable constraint as set forth below.

As used herein, the term "regulated," when used in reference to a reaction in a data structure, is intended to mean a reaction that experiences an altered flux due to a change in the value of a constraint or a reaction that has a variable constraint.

As used herein, the term "regulatory reaction" is intended to mean a chemical conversion or interaction that alters the activity of a protein, macromolecule or enzyme. A chemical conversion or interaction can directly alter the activity of a protein, macromolecule or enzyme such as occurs when the protein, macromolecule or enzyme is post-translationally modified or can indirectly alter the activity of a protein, macromolecule or enzyme such as occurs when a chemical conversion or binding event leads to altered expression of the protein, macromolecule or enzyme. Thus, transcriptional or translational regulatory pathways can indirectly alter a protein, macromolecule or enzyme or an associated reaction. Similarly, indirect regulatory reactions can include reactions that occur due to downstream components or participants in a regulatory reaction network. When used in reference to a data structure or in silico model, for example, the term is intended to mean a first reaction that is related to a second reaction by a function that alters the flux through the second reaction by changing the value of a constraint on the second reaction.

As used herein, the term "regulatory data structure" is intended to mean a representation of an event, reaction or network of reactions that activate or inhibit a reaction, the representation being in a format that can be manipulated or analyzed. An event that activates a reaction can be an event that initiates the reaction or an event that increases the rate or level of activity for the reaction. An event that inhibits a reaction can be an event that stops the reaction or an event that decreases the rate or level of activity for the reaction. Reactions that can be represented in a regulatory data structure include, for example, reactions that control expression of a macromolecule that in turn, performs a reaction such as transcription and translation reactions, reactions that lead to post translational modification of a protein or enzyme such as phosphorylation, dephosphorylation, prenylation, methylation, oxidation or covalent modification, reactions that process a protein or enzyme such as removal of a pre- or pro-sequence, reactions that degrade a protein or enzyme or reactions that lead to assembly of a protein or enzyme.

As used herein, the term "regulatory event" is intended to mean a modifier of the flux through a reaction that is independent of the amount of reactants available to the reaction. A modification included in the term can be a change in the presence, absence, or amount of an enzyme that performs a reaction. A modifier included in the term can be a regulatory reaction such as a signal transduction reaction or an environmental condition such as a change in pH, temperature, redox potential or time. It will be understood that when used in reference to a model or data structure, a regulatory event is intended to be a representation of a modifier of the flux through reaction that is independent of the amount of reactants available to the reaction.

The effects of regulation on one or more reactions that occur in a cell can be predicted using an in silico cell model. Regulation can be taken into consideration in the context of a particular condition being examined by providing a variable constraint for the reaction in an in silico model. Such constraints constitute condition-dependent constraints. A data structure can represent regulatory reactions as Boolean logic statements (Reg-reaction). The variable takes on a value of 1 when the reaction is available for use in the reaction network and will take on a value of 0 if the reaction is restrained due to some regulatory feature. A series of Boolean statements can then be introduced to mathematically represent the regulatory network as described for example in Covert et al. *J. Theor. Biol.* 213:73-88 (2001). For example, in the case of a transport reaction (A_in) that imports metabolite A, where metabolite A inhibits reaction R2, a Boolean rule can state that:

$$\text{Reg-}R2 = \text{IF NOT}(A\_\text{in}) \qquad \text{(Eq. 4)}$$

This statement indicates that reaction R2 can occur if reaction A_in is not occurring (i.e. if metabolite A is not present). Similarly, it is possible to assign the regulation to a variable A which would indicate an amount of A above or below a threshold that leads to the inhibition of reaction R2. Any function that provides values for variables corresponding to each of the reactions in the biochemical reaction network can be used to represent a regulatory reaction or set of regulatory reactions in a regulatory data structure. Such functions can include, for example, fuzzy logic, heuristic rule-based descriptions, differential equations or kinetic equations detailing system dynamics.

A reaction constraint placed on a reaction can be incorporated into an in silico model using the following general equation:

$$(Reg-Reaction)*b_j \leq v_j \leq a_j*(Reg-Reaction), \forall\, j=1\ldots n \qquad (Eq.\ 5)$$

For the example of reaction R2 this equation is written as follows:

$$(0)*Reg-R2 \leq R2 \leq (\infty)*Reg-R2 \qquad (Eq.\ 6)$$

Thus, during the course of a simulation, depending upon the presence or absence of metabolite A in the interior of the cell where reaction R2 occurs, the value for the upper boundary of flux for reaction R2 will change from 0 to infinity, respectively. With the effects of a regulatory event or network taken into consideration by a constraint function and the condition-dependent constraints set to an initial relevant value, the behavior of the reaction network can be simulated for the conditions considered as set forth below.

Although regulation has been exemplified above for the case where a variable constraint is dependent upon the outcome of a reaction in the data structure, a plurality of variable constraints can be included in an in silico model to represent regulation of a plurality of reactions. Furthermore, in the exemplary case set forth above, the regulatory structure includes a general control stating that a reaction is inhibited by a particular environmental condition. Using a general control of this type, it is possible to incorporate molecular mechanisms and additional detail into the regulatory structure that is responsible for determining the active nature of a particular chemical reaction within an organism.

Regulation can also be simulated by a model and used to predict a physiological function of a cell without knowledge of the precise molecular mechanisms involved in the reaction network being modeled. Thus, the model can be used to predict, in silico, overall regulatory events or causal relationships that are not apparent from in vivo observation of any one reaction in a network or whose in vivo effects on a particular reaction are not known. Such overall regulatory effects can include those that result from overall environmental conditions such as changes in pH, temperature, redox potential, or the passage of time.

Those of skill in the art will recognize that instructions for the software implementing a method and model of the present disclosure can be written in any known computer language, such as Java, C, C++, Visual Basic, FORTRAN or COBOL, and compiled using any compatible compiler; and that the software can run from instructions stored in a memory or computer-readable medium on a computing system.

A computing system can be a single computer executing the instructions or a plurality of computers in a distributed computing network executing parts of the instructions sequentially or in parallel. The single computer or one of the plurality of computers can comprise a single processor (for example, a microprocessor or digital signal processor) executing assigned instructions or a plurality of processors executing different parts of the assigned instructions sequentially or in parallel. The single computer or one of the plurality of the computers can further comprise one or more of a system unit housing, a video display device, a memory, computational entities such as operating systems, drivers, graphical user interfaces, applications programs, and one or more interaction devices, such as a touch pad or screen. Such interaction devices or graphical user interfaces, and the like, can be used to output a result to a user, including a visual output or data output, as desired.

A memory or computer-readable medium for storing the software implementing a method and model of the present disclosure can be any medium that participates in providing instructions to a processor for execution. Such a medium may take many forms, including, but not limited to, non-volatile media, volatile media, and transmission media. Non-volatile media include, for example, optical or magnetic disks. Volatile media include dynamic memory. Transmission media include coaxial cables, copper wire, and fiber optics. Transmission media can also take the form of acoustic or light waves, such as those generated during radio frequency and infrared data communications. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. A carrier wave can also be used but is distinct from a computer readable medium or media. Thus, a computer readable medium or media as used herein specifically excludes a carrier wave.

The memory or computer-readable medium can be contained within a single computer or distributed in a network. A network can be any of a number of network systems known in the art such as a Local Area Network (LAN), or a Wide Area Network (WAN). The LAN or WAN can be a wired network (e.g., Ethernet) or a wireless network (e.g., WLAN). Client-server environments, database servers and networks that can be used to implement certain aspects of the present disclosure are well known in the art. For example, database servers can run on an operating system such as UNIX, running a relational database management system, a World Wide Web application and a World Wide Web server. Other types of memories and computer readable media area also contemplated to function within the scope of the present disclosure.

A database or data structure embodying certain aspects or components of the present disclosure can be represented in a markup language format including, for example, Standard Generalized Markup Language (SGML), Hypertext Markup Language (HTML) or Extensible Markup Language (XML). Markup languages can be used to tag the information stored in a database or data structure, thereby providing convenient annotation and transfer of data between databases and data structures. In particular, an XML format can be useful for structuring the data representation of reactions, reactants, and their annotations; for exchanging database contents, for example, over a network or the Internet; for updating individual elements using the document object model; or for providing different access to multiple users for different information content of a database or data structure embodying certain aspects of the present disclosure. XML programming methods and editors for writing XML codes are known in the art as described, for example, in Ray, "Learning XML" O'Reilly and Associates, Sebastopol, Calif. (2001).

Those of skill in the art would appreciate that the various illustrative blocks, modules, elements, components, methods, and algorithms described herein may be implemented as electronic hardware, computer software, or combinations of both. Furthermore, these may be partitioned differently than what is described. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans can implement the described functionality in varying ways for each particular application.

A set of constraints can be applied to a reaction network data structure to simulate the flux of mass through the reaction network under a particular set of environmental conditions specified by a constraints set. Because the time constants characterizing metabolic transients and/or metabolic reactions are typically very rapid, on the order of milli-seconds to seconds, compared to the time constants of cell growth on the order of hours to days, the transient mass balances can be simplified to only consider the steady state behavior. Referring now to an example where the reaction network data structure is a stoichiometric matrix, the steady state mass balances can be applied using the following system of linear equations $$S \cdot v = 0 \quad \text{(Eq. 7)}$$

where S is the stoichiometric matrix as defined above and v is the flux vector. This equation defines the mass, energy, and redox potential constraints placed on the metabolic network as a result of stoichiometry. Together Equations 1 and 5 representing the reaction constraints and mass balances, respectively, effectively define the capabilities and constraints of the metabolic genotype and the organism's metabolic potential. All vectors, v, that satisfy Equation 5 are said to occur in the mathematical nullspace of S. Thus, the null space defines steady-state metabolic flux distributions that do not violate the mass, energy, or redox balance constraints. Typically, the number of fluxes is greater than the number of mass balance constraints, thus a plurality of flux distributions satisfy the mass balance constraints and occupy the null space. The null space, which defines the feasible set of metabolic flux distributions, is further reduced in size by applying the reaction constraints set forth in Equation 1 leading to a defined solution space. A point in this space represents a flux distribution and hence a metabolic phenotype for the network. An optimal solution within the set of all solutions can be determined using mathematical optimization methods when provided with a stated objective and a constraint set. The calculation of any solution constitutes a simulation of the model.

Objectives for activity of a cell can be chosen. While the overall objective of a multi-cellular organism may be growth or reproduction, individual human cell types generally have much more complex objectives, even to the seemingly extreme objective of apoptosis (programmed cell death), which may benefit the organism but certainly not the individual cell. For example, certain cell types may have the objective of maximizing energy production, while others have the objective of maximizing the production of a particular hormone, extracellular matrix component, or a mechanical property such as contractile force. In cases where cell reproduction is slow, such as human skeletal muscle, growth and its effects need not be taken into account. In other cases, biomass composition and growth rate could be incorporated into a "maintenance" type of flux, where rather than optimizing for growth, production of precursors is set at a level consistent with experimental knowledge and a different objective is optimized.

Certain cell types, including cancer cells, can be viewed as having an objective of maximizing cell growth. Growth can be defined in terms of biosynthetic requirements based on literature values of biomass composition or experimentally determined values such as those obtained as described above. Thus, biomass generation can be defined as an exchange reaction that removes intermediate metabolites in the appropriate ratios and represented as an objective function. In addition to draining intermediate metabolites this reaction flux can be formed to utilize energy molecules such as ATP, NADH and NADPH so as to incorporate any maintenance requirement that must be met. This new reaction flux then becomes another constraint/balance equation that the system must satisfy as the objective function. Using a stoichiometric matrix as an example, adding such a constraint is analogous to adding an additional column $V_{growth}$ to the stoichiometric matrix to represent fluxes to describe the production demands placed on the metabolic system. Setting this new flux as the objective function and asking the system to maximize the value of this flux for a given set of constraints on all the other fluxes is then a method to simulate the growth of the organism.

Continuing with the example of the stoichiometric matrix applying a constraint set to a reaction network data structure can be illustrated as follows. The solution to equation 5 can be formulated as an optimization problem, in which the flux distribution that minimizes a particular objective is found. Mathematically, this optimization problem can be stated as:

$$\text{Minimize } Z \quad \text{(Eq. 8)}$$

$$\text{where } z = \Sigma c_i \cdot v_i \quad \text{(Eq. 9)}$$

where Z is the objective which is represented as a linear combination of metabolic fluxes $v_i$ using the weights $c_i$ in this linear combination. The optimization problem can also be stated as the equivalent maximization problem; i.e. by changing the sign on Z. Any commands for solving the optimization problem can be used including, for example, linear programming commands.

A computer system can further include a user interface capable of receiving a representation of one or more reactions. A user interface can also be capable of sending at least one command for modifying the data structure, the constraint set or the commands for applying the constraint set to the data representation, or a combination thereof. The interface can be a graphic user interface having graphical means for making selections such as menus or dialog boxes. The interface can be arranged with layered screens accessible by making selections from a main screen. The user interface can provide access to other databases useful in the invention such as a metabolic reaction database or links to other databases having information relevant to the reactions or reactants in the reaction network data structure or to a cell's physiology. Also, the user interface can display a graphical representation of a reaction network or the results of a simulation using a model.

Once an initial reaction network data structure and set of constraints has been created, this model can be tested by preliminary simulation. During preliminary simulation, gaps in the network or "dead-ends" in which a metabolite can be produced but not consumed or where a metabolite can be consumed but not produced can be identified. Based on the results of preliminary simulations, areas of the metabolic reconstruction that require an additional reaction can be identified. The determination of these gaps can be readily calculated through appropriate queries of the reaction network data structure and need not require the use of simulation strategies, however, simulation would be an alternative approach to locating such gaps.

In the preliminary simulation testing and model content refinement stage the existing model is subjected to a series of functional tests to determine if it can perform basic requirements such as the ability to produce the required biomass constituents and generate predictions concerning the basic physiological characteristics of the particular cell type being modeled. The more preliminary testing that is conducted, the higher the quality of the model that will be generated. Typically, the majority of the simulations used in this stage of development will be single optimizations. A single optimization can be used to calculate a single flux distribution demonstrating how metabolic resources are routed determined from the solution to one optimization problem. An optimization problem can be solved using linear programming as disclosed herein. The result can be viewed as a display of a flux distribution on a reaction map. Temporary reactions can be added to the network to determine if they should be included into the model based on modeling/simulation requirements.

Once a model is sufficiently complete with respect to the content of the reaction network data structure according to the criteria set forth above, the model can be used to simulate activity of one or more reactions in a reaction network. The results of a simulation can be displayed in a variety of formats including, for example, a table, graph, reaction network, flux distribution map or a phenotypic phase plane graph.

As used herein, the term "physiological function," when used in reference to a cell, is intended to mean an activity of the cell as a whole. An activity included in the term can be the magnitude or rate of a change from an initial state of a cell to a final state of the cell. An activity included in the term can be, for example, growth, energy production, redox equivalent production, biomass production, development, or consumption of carbon nitrogen, sulfur, phosphate, hydrogen or oxygen. An activity can also be an output of a particular reaction that is determined or predicted in the context of substantially all of the reactions that affect the particular reaction in a cell or that occur in a cell. Examples of a particular reaction included in the term are production of biomass precursors, production of a protein, production of an amino acid, production of a purine, production of a pyrimidine, production of a lipid, production of a fatty acid, production of a cofactor or transport of a metabolite, and the like. A physiological function can include an emergent property which emerges from the whole but not from the sum of parts where the parts are observed in isolation (see for example, Palsson, *Nat. Biotech* 18:1147-1150 (2000)).

A physiological function of reactions can be determined using phase plane analysis of flux distributions. Phase planes are representations of the feasible set which can be presented in two or three dimensions. As an example, two parameters that describe the growth conditions such as substrate and oxygen uptake rates can be defined as two axes of a two-dimensional space. The optimal flux distribution can be calculated from a reaction network data structure and a set of constraints as set forth above for all points in this plane by repeatedly solving the linear programming problem while adjusting the exchange fluxes defining the two-dimensional space. A finite number of qualitatively different metabolic pathway utilization patterns can be identified in such a plane, and lines can be drawn to demarcate these regions. The demarcations defining the regions can be determined using shadow prices of linear optimization as described, for example in Chvatal, *Linear Programming* New York, W.H. Freeman and Co. (1983). The regions are referred to as regions of constant shadow price structure. The shadow prices define the intrinsic value of each reactant toward the objective function as a number that is either negative, zero, or positive and are graphed according to the uptake rates represented by the x and y axes. When the shadow prices become zero as the value of the uptake rates are changed there is a qualitative shift in the optimal reaction network.

One demarcation line in the phenotype phase plane is defined as the line of optimality (LO). This line represents the optimal relation between respective metabolic fluxes. The LO can be identified by varying the x-axis flux and calculating the optimal y-axis flux with the objective function defined as the growth flux. From the phenotype phase plane analysis the conditions under which a desired activity is optimal can be determined. The maximal uptake rates lead to the definition of a finite area of the plot that is the predicted outcome of a reaction network within the environmental conditions represented by the constraint set. Similar analyses can be performed in multiple dimensions where each dimension on the plot corresponds to a different uptake rate. These and other methods for using phase plane analysis, such as those described in Edwards et al., *Biotech Bioeng.* 77:27-36 (2002), can be used to analyze the results of a simulation using an in silico model.

A physiological function of a cell can also be determined using a reaction map to display a flux distribution. A reaction map of a cell can be used to view reaction networks at a variety of levels. In the case of a cellular metabolic reaction network, a reaction map can contain the entire reaction complement representing a global perspective. Alternatively, a reaction map can focus on a particular region of metabolism such as a region corresponding to a reaction subsystem described above or even on an individual pathway or reaction.

The methods can be used to determine the activity of a plurality of cell reactions including, for example, biosynthesis of an amino acid, degradation of an amino acid, biosynthesis of a purine, biosynthesis of a pyrimidine, biosynthesis of a lipid, metabolism of a fatty acid, biosynthesis of a cofactor, transport of a metabolite, metabolism of an alternative carbon source, or other reactions as disclosed herein.

The methods can be used to determine a phenotype of a cell mutant. The activity of one or more reactions can be determined using the methods described herein, wherein the reaction network data structure lacks one or more gene-associated reactions that occur in a cell or organism. Alternatively, the methods can be used to determine the activity of one or more reactions when a reaction that does not naturally occur in the model of a cell or organism, for example, is added to the reaction network data structure. Deletion of a gene can also be represented in a model by constraining the flux through the reaction to zero, thereby allowing the reaction to remain within the data structure. Thus, simulations can be made to predict the effects of adding or removing genes to or from a cell. The methods can be particularly useful for determining the effects of adding or deleting a gene that encodes for a gene product that performs a reaction in a peripheral metabolic pathway.

A target for an agent that affects a function of a cell can be predicted using the methods of the invention, for example a target pathway for determining a selectable marker for a cell line, as disclosed herein. Such predictions can be made by removing a reaction to simulate total inhibition or prevention by a drug or agent. Alternatively, partial inhibition or reduction in the activity a particular reaction can be predicted by performing the methods with altered constraints. For example, reduced activity can be introduced into a model of the invention by altering the $a_j$ or $b_j$ values for the metabolic flux vector of a target reaction to reflect a finite maximum or minimum flux value corresponding to the level of inhibition. Similarly, the effects of activating a reaction, by initiating or increasing the activity of the reaction, can be predicted by performing the methods with a reaction network data structure lacking a particular reaction or by altering the $a_j$ or $b_j$ values for the metabolic flux vector of a target reaction to reflect a maximum or minimum flux value corresponding to the level of activation. The methods can be particularly useful for identifying a target in a peripheral metabolic pathway.

The methods of the invention can be used to determine the effects of one or more environmental components or conditions on an activity of, for example, a physiological function of a cell such as a media component or nutrient, as disclosed herein. As set forth above, an exchange reaction can be added to a reaction network data structure corresponding to uptake of an environmental component, release of a component to the environment, or other environmental demand. The effect of the environmental component or condition can be further investigated by running simulations with adjusted $a_j$ or $b_j$ values for the metabolic flux vector of the exchange reaction target reaction to reflect a finite maximum or minimum flux value corresponding to the effect of the environmental component or condition. The environmental component can be, for example an alternative carbon source or a metabolite that when added to the environment of a cell such as the medium in which the cell is grown can be taken up and metabolized. The environmental component can also be a combination of components present for example in a minimal medium composition. Thus, the methods can be used to determine an optimal or minimal medium composition that is capable of supporting a particular activity of a cell.

It is understood that modifications which do not substantially affect the activity of the various embodiments of this invention are also provided within the definition of the invention provided herein. Accordingly, the following examples are intended to illustrate but not limit the present invention.

EXAMPLE I

Design of New Selection Systems

This example describes selecting cell lines for optimized production. This method was previously described in WO 2010/098865, filed Feb. 26, 2010.

The need to develop new and optimized methods for host cell engineering and for selection of high-producing clones within heterogeneous populations in a timely and cost-efficient manner has become more and more crucial, particularly as regulatory constraints on development timelines remain stringent and production demands for new therapeutics continue to rise (Altamirano et al., *Biotechnol. Prog.* 17:1032-1041 (2001)).

One of the major challenges in mammalian based protein production is population heterogeneity that results following cell line transfection. Heterogeneous populations contain cells with different integration sites, copy numbers and varying specific productivities. Some of these are obviated by using clones; however, spontaneous loss of expression also happens. Low- or non-producing subpopulations can outgrow the producing population, thereby substantially lowering product yields. To enhance protein production, transfected cells must be extensively screened, often spanning over several months in the early stages of product development, to identify and select high producing clones.

Currently, the industrial production of many commercially valuable proteins predominantly involves the use of two selection markers, both of which capitalize on the use of a metabolic enzyme: dihydrofolate reductase (DHFR) (Seth et al., *Curr. Opin. Biotechnol.* 18:557-564 (2007)) and glutamine synthetase (GS) (Page and Sydenham, *Biotechnology* 9:64-68 (1991)). In both cases, simultaneous expression of these essential enzymes along with production of the recombinant protein allows for the selection of high producing clones in the cell culture. Despite their widespread and established use in cell line protein production, the use of DHFR and GS selection systems are limited by a number of disadvantages. The DHFR selection system can take more than 6 months to be implemented, it is laborious and can be leaky (i.e. it looses its selectivity over time (Cockett et al., *Biotechnology* 8:662-667 (1990)). It requires repeated rounds of selection and amplification with the expensive and toxic enzyme inhibitor methotrexate, and additional screening steps (e.g. series of limiting dilutions) to isolate clones with a high specific productivity (Wurm, *Nat. Biotechnol.* 22:1393-1398 (2004); Page and Sydenham, *Biotechnology* 9:64-68 (1991)). The GS selection system on the other hand uses only one round of selection for gene amplification, and in addition generates metabolic advantages to the cell culture, including reduction of toxic ammonia formation and increased cell viability (Page and Sydenham, *Biotechnology* 9:64-68 (1991); Urlaub and Chasin, *Proc. Natl. Acad. Sci. U.S.A.* 77:4216-4220 (1980)). It takes only 2 months for the GS selection system to generate high producing clones, however, the use of the GS system is expensive and requires substantial licensing and royalty payments (Zhang et al., *Cytotechnology* 51:21-28 (2006)).

In addition to the DHFR and GS systems, other selection markers have been tested in the past ten years. However, no significant advancements in the selection system design have been made thus far. As a result, there is a growing industrial demand for new and superior selection systems (Kingston et al., *Current Protocols in Molecular Biology* (John Wiley & sons, Inc., (1993)) that: (i) are inexpensive, scaleable, quick, and simple to use, (ii) do not require multiple rounds of selection and amplification, (iii) perform in a stringent selection manner, and (iv) preferably induce additive metabolic advantages to mammalian cell culture. As with GS and DHFR, metabolic enzymes can thus offer unique advantages for developing new selection systems in mammalian cell lines for high producing clone selection. To identify and develop such new selection systems, modeling and simulation technologies that capture the underlying metabolism and physiology of the host cell line can significantly accelerate the development of a superior selection system in mammalian protein production.

A computational modeling platform, called SimPheny™ (short for Simulating Phenotypes), that enables the efficient development of genome-scale models of metabolism and their simulation using a constraint-based modeling approach (Browne and Ul-Rubeai, *Trends Biotechnol.* 25:425-432 (2007); U.S. publication 20030233218). Within this platform, over a dozen bacterial and eukaryotic models have been developed that are used in strain engineering and bioprocessing for a wide range of product development applications. More recently this platform has been used for modeling mammalian systems, including for murine hybridoma, NS0, and Chinese Hamster Ovary (CHO) cell lines. The reconstructed metabolic models of the aforementioned mammalian cell lines have been extensively validated both retrospectively and prospectively for the study of growth as well as metabolite uptake and secretion profiles of batch and fed-batch cell cultures.

A systems biology approach utilizes the knowledge of a whole cell metabolism and is capable to provide rational designs for identifying new selection systems. The overall goal of this proof-of-concept study is to utilize the integrated modeling and experimental approach to computationally identify and experimentally evaluate new selection systems in CHO cell line. New selection system design can be done by:

I: Identification and prioritizing new selection systems in CHO cell line using a reconstructed metabolic model: Essential metabolic reactions can be identified using the model that are candidate targets for designing new selection systems in CHO cell line. A network-wide in silico deletion analysis can be performed using the reconstructed model of CHO metabolism, to search for essential metabolic functions that can be used as the basis for new auxotrophic selections. Candidate targets can be prioritized based on a number of criteria, including a predicted stringent specificity of the new selection system based on an in silico deletion analysis and improved cell physiology, such as reduced byproduct formation and increased growth rate.

II: Experimentally implementing the top candidate selection system in CHO cell line: The top candidate selection system identified can be experimentally implemented by first creating a clone of the CHO cell line that is auxotrophic for a predicted media component. Disruption of the target gene(s) can done using a zinc-finger nuclease system made available for use by Sigma-Aldrich (Price et al., *Nat. Rev. Microbiol.* 2:886-897 (2004); Santiago et al., *Proc. Natl. Acad. Sci. U.S.A.* 105:5809-5814 (2008)). The generated deletion clone can then be tested for its auxotrophic characteristics. Verified auxotrophic clones can be transfected with a selection vector that includes the sequences of the genes that encode a traceable antibody to model a therapeutic protein, and an active allele of the previously disrupted gene encoding the essential enzyme(s), i.e. the selection marker. Stable antibody-producing clones will also be verified for the implemented selection system and antibody production.

III. Evaluating the development and implementation of a model-based selection system in CHO cell line: To determine the success of developing a new selection system in a CHO cell line, we will compare experimentally generated cell culture data can be compared with those calculated by the reconstructed CHO metabolic model. The deletion and antibody producing clones created are characterized using spinner flask cultivations. Growth, metabolite uptake, and byproduct secretion patterns of the deletion and antibody producing clones can be qualitatively compared with the computationally predicted results.

New selection systems can thus be computationally identified and experimentally validated a new selection system in CHO cells, focused on targets with added metabolic advantages such as reduced byproduct formation and increased growth rate. The resulting new selection system and antibody production can be developed and improved further using existing experimental and computational techniques, and other new targets can be identified and validated.

Current Approaches in Protein Producing Clone Selection and Screening. Selection markers play an important role in the overall development process of therapeutic proteins in mammalian cell cultures. Selection markers are used to ensure that mammalian cells have been successfully transfected with a heterologous gene of interest. Such transfected cells can then be screened for maximal expression of the cognate heterologous protein of interest (Browne and Al-Rubeai, *Trends Biotechnol.* 25:425-432 (2007); Wurm, *Nat. Biotechnol.* 22:1393-1398 (2004)). In general, selection and screening systems for mammalian cell cultures are designed using one or a combination of the following strategies: (i) utilization of strain auxotrophic characteristics, (ii) exploitation of strain resistance to a drug, and (iii) the expression of heterologous proteins (e.g GFP) that can be physically detected using flow cytometry or other robotics tools.

In the past, production of therapeutic proteins in mammalian cell lines has been dominated by the use of selection markers that have metabolic origin, including dihydrofolate reductase (DHFR) (Page and Sydenham, *Biotechnol.* 9:64-68 (1991)), glutamine synthetase (GS) (Cockett et al., *Biotechnology* 8:662-667 (1990)), thymidylate synthase (Ayusawa et al., *Somatic. Cell Genet.* 7:523-534 (1981)) and bacterial xanthine guanine phosphorybosyl transferase (Mulligan and Berg, *Science* 209:1422-1427 (1980)). The industrial production of many commercially valuable proteins has focused largely on two markers, DHFR (Page and Sydenham, supra) and GS (Cockett et al., *Biotechnology* 8:662-667 (1990)). The DHFR system is routinely and widely used with CHO cells that are deficient in the DHFR activity and thus require hypoxanthine and thymidine in the medium for growth and nucleotide production (Page and Sydenham, supra). The DHFR selection system is sensitive to ectopic differences in expression, requiring repeated rounds of selection and amplification with the expensive and toxic enzyme inhibitor methotrexate, as well as additional screening steps (e.g. series of limiting dilutions) to isolate clones with a high specific productivity of the target protein (Jayapal et al., *Chem. Eng. Progress* 103:40-47 (2007); Cockett et al., supra). Also, spontaneous mutations within the DHFR gene can cause leakiness of the selection strategy (Urlaub and Chasin, *Proc. Natl. Acad. Sci. U.S.A.* 77:4216-4220 (1980)). Overall, this system can result in very high levels of heterologous protein amplification (1000 copies per cell) (Kingston et al., *Current Protocols in Molecular Biology*, John Wiley & Sons, Inc., (1993)), however, the extra work needed to screen for stable and highly expressing clonal strains can take 6 to 12 months (Jayapal et al., *Chem. Eng. Progress* 103:40-47 (2007)). In contrast the GS system typically requires only a single round of selection and amplification to generate maximally expressing heterologous protein producers (Cockett et al., supra). CHO cells have a low level of endogenous glutamine synthetase activity, which usually can maintain cell growth in the absence of glutamine; however, the growth is not as good as in the presence of glutamine. Upon transfection with a GS selection system, CHO cell lines gain a significant metabolic advantage—these cell lines have increased viability in glutamine-free media and they produce less ammonia, which is a toxic metabolic byproduct that can adversely affect protein glycosylation and cell growth rates (Zhang et al., *Cytotechnology* 51:21-28 (2006)). The additional selective pressure of toxic methionine sulfoximine (MSX) is used to amplify GS and heterologous protein production (Cockett et al., supra). It takes only 2 months for the GS selection system to generate stable high producing clones; however, the use of the GS system is expensive as it requires substantial licensing and royalty payments (Kingston et al., *Current Protocols in Molecular Biology* (John Wiley & Sons, Inc., (1993)).

Importance of New Selection System Development. Selection of high-producing mammalian cell lines represents a bottleneck in process development for the production of biopharmaceuticals, both in terms of the required development time and bioreactor capacity (Browne and Al-Rubeai, *Trends Biotechnol.* 25:425-432 (2007)). The market of therapeutic proteins is expected to double between 2007 and 2010. If the biopharmaceutical industry is to meet with increasing market demand, more efficient methods of cell line selection are required (Browne and Al-Rubeai, supra). Despite a significant effort in development of new selection systems for the past 20 years, no major improvements resulting in new and superior selection system designs have been achieved. Current selection methods are hampered by a number of disadvantages and are time-consuming, expensive and not suitable for large scale production (Browne and Al-Rubeai, supra). Most selection systems require continuous addition of selective agents such as antibiotics or toxic compounds to maintain high protein production. With increasing stringency in biotherapeutic production and manufacturing regulations it is essential to ensure that the end product contains no antibiotics and no genes for antibiotic resistance (TechNote: Antibiotic-Free Systems for Production. *Genetic Engineering & Biotechnology News* 26, (2006)). Removing these selection agents from industrial protein production cultivations can cause loss of stable protein producing strains and can greatly hamper therapeutic protein production. Therefore, the industry has long been in need of new selection systems that are relatively simple, reliable and inexpensive (Browne and Al-Rubeai, supra).

In addition to the need for more reliable and less expensive selection systems, there is an increasing need to develop superior mammalian cell lines with improved metabolic characteristics. Previous cell line engineering efforts have focused on controlling metabolic flow in mammalian expression systems, including CHO cell lines, to reduce production of toxic metabolic intermediates and byproducts (e.g. lactate and ammonium). In addition to reducing metabolic efficiency of the cell for protein production, secretion of metabolic byproducts can negatively affect cell growth, cell viability, and product formation in industrial cultivations (Altamirano et al., *Biotechnol. Prog.* 17:1032-1041 (2001); Irani et al., *Biotechnol. Bioeng.* 66:238-246 (1999); Jeong et al., *Mol. Cell. Biochem.* 284:1-8 (2006)). The GS selection system, developed through a minimal and rational manipulation of cell metabolism, is an example of a selection system with beneficial metabolic characteristics. In the GS selection system, glutamine is synthesized intracellularly, allowing the transfected cells to grow in a glutamine-free media. The added advantage of the GS system is that the cell culture produces less ammonium in continuous mammalian cell line cultivation, improving the overall cell viability and productivity (Cockett et al., *Biotechnology* 8:662-667 (1990); Zhang et al., *Cytotechnology* 51:21-28 (2006)). As shown in the GS system, developing an effective and inexpensive selection system that simultaneously improves the metabolic characteristics of the cell line is of great value in the production of therapeutic proteins in mammalian cell lines.

Other metabolic enzymes could be promising alternatives with additional metabolic advantages for developing new selection systems in mammalian cell lines for high-producing clone selection similar to the GS selection system. Identifying such selection systems, however, requires a fundamental understanding of metabolic pathways in the cell. A comprehensive knowledge of cell metabolism and the interlinking metabolic pathways allows for identifying candidate selection systems that: (i) only use media supplements, needed for biomass production, as a selective pressure, (ii) eliminate the need to use expensive additives i.e. antibiotics or enzyme inhibiting compounds in cell engineering processes, (iii) eliminate the need of multiple cloning and use of multiple selection systems in the engineering of high protein producing cell line, and (iv) cause metabolic improvement (e.g. regulation of alanine overflow, induction of cell growth or reduction of byproduct formation) in mammalian cell lines. The integrated computational and experimental platform provides a unique framework for identifying and developing such superior selection systems to select better performing mammalian cell lines.

Importance of Metabolic Modeling in Design of Selection Systems and Improved Mammalian Cell Line Culture. Understanding cell physiology and interlinking metabolic pathways is key when designing superior selection systems. Modeling and simulation technologies that capture the underlying metabolism and physiology of the host cell line can significantly accelerate the development of a superior selection system in mammalian protein production. Computational metabolic modeling can serve as a research and design tool to: Identify what pathways are being used under specified genetic and environmental conditions; Determine the fate of nutrients in the cell; Identify the source of potentially toxic waste products; Examine the effect of eliminating existing reactions or adding new pathways to the host cell line; Analyze the effect of adding nutrients to the media; Interpret process changes (e.g. scale-up) at a fundamental physiological level; Generate rational design strategies for cell engineering, media optimization and process development.

Thus, a whole-cell network reconstruction for mammalian cell line metabolism will be extremely valuable as a platform for engineering mammalian cell line culture. There are strong scientific and financial incentives to develop technology that can speed-up desired mammalian cell clone engineering and selection, while simultaneously reducing the cost of the process. Many metabolic factors influence the performance of a selection system. Understanding metabolic changes that follow genetic and environmental perturbations in the cell culture engineering processes will allow for the development of more effective selection systems to ultimately improve cell culture and avoid unexpected variation in cell culture protein production.

Any attempt to improve protein production by overcoming fundamental metabolic limitations requires a platform for the comprehensive analysis of cellular metabolic systems. Genome-scale models of metabolism offer the most effective way to achieve a high-level characterization and representation of metabolism. These models reconcile all of the existing genetic, biochemical, and physiological data into a metabolic reconstruction encompassing all of the metabolic capabilities and fitness of an organism. These in silico models serve as the most concise representation of collective biological knowledge on the metabolism of a cell. As such they become the focal point for the integrative analysis of vast amounts of experimental data and a central resource to design experiments, interpret experimental data, and drive research programs. It is now becoming recognized that the construction of genome-scale in silico models is important to integrate large amounts of diverse high-throughput datasets and to prospectively design experiments to systematically "fill in the gaps" in knowledge base of particular organisms (Ideker et al., *Science* 292:929-934 (2001)).

The exercise of constructing and demonstrating the use of genome-scale models of metabolism began in earnest out of academic efforts in which this team was involved. Previously published in silico representations of metabolism include those for *Escherichia coli* MG1655 (Edwards and Palsson, *Proc. Natl. Acad. Sci. U.S.A.* 97:5528-5533 (2000)), *H. influenzae* Rd (Edwards and Palsson, *J. Biol. Chem.* 274:17410-17416 (1999); Schilling and Palsson, *J. Theor. Biol.* 203:249-283 (2000)), *H. pylori* (Schilling et al., *J. Bacteriol.* 184:4582-4593 (2002)), *S. cerevisiae* (Forster et al., *Genome Res.*

13:244-253 (2003)), and *Homo sapiens* (Duarte et al., *Proc. Natl. Acad. Sci. U.S.A.* 104:1777-1782 (2007)). More recently this platform has been used for modeling mammalian cell lines, including murine hybridoma, NS0, and Chinese Hamster Ovary (CHO) cell lines. The general process has been previously published along with various applications of the in silico models (Schilling et al., *Biotechnol. Prog.* 15:288-295 (1999); Covert et al., *Trends Biochem. Sci.* 26:179-186 (2001)). In combination with appropriate simulation methods, these models can also be used to generate hypotheses to guide experimental design efforts and to improve the design and optimization of selection systems for mammalian cell lines. When properly integrated with experimental technologies, an extremely powerful combined platform for design of selection systems and mammalian cell line engineering can be implemented for a wide range of applications within the pharmaceutical and biotechnology industries for production and development of healthcare products, therapeutic proteins, and biologics.

In silico deletion analysis has been successfully used to predict the viability of various gene knockouts in genome-scale metabolic models of *Escherichia coli* and *Sacchromyces cerevisiae* using a constraint-based modeling approach (Forster et al., *OMICS* 7:193-202 (2003); Edwards and Palsson, *BMC Bioinformatics* 1:1 (2000)). In *E. coli*, an in silico deletion analysis was carried out on the central metabolic genes. The in silico growth results under different substrate conditions were then compared with experimental data and shown to predict 86% (68 of 79 cases) correctly (Edwards and Palsson, supra). When the model made an incorrect prediction, that prediction was always conservative (i.e. the model said the cell could grow while the experiments showed no growth). A later study analyzed 13,750 growth phenotypes and the model agreed in 10,828 (78.7%) of those cases (Covert et al., *Nature* 429:92-96 (2004)). An in silico deletion analysis was also carried out in the yeast *S. cerevisiae*. In the first study, in silico growth was correctly predicted for 81.5% (93 of 114) of the cases (Famili et al., *Proc. Natl. Acad. Sci. U.S.A.* 100:13134-13139 (2003)). A later study expanded the in silico analysis to the genome-scale, correctly predicting 89.4% knockout cases (496 of 555) (Forster et al., supra). Thus, the viability of gene knockouts in genome-scale metabolic models has shown to be predicted with high accuracy.

The results described herein and previously in WO 2010/098865, filed Feb. 26, 2010, clearly demonstrated that the reconstructed CHO cell line model correctly simulates metabolism in cell culture, and thus can be used effectively for the design of new selection systems. The feasibility of identifying new selection systems using an integrated computational and experimental approach, whereby predictions based on analyses of the CHO cell line metabolic model is described below. To accomplish this goal, the reconstructed model of CHO metabolism is used in combination with experimental capabilities to computationally identify new selection systems in CHO cell lines and experimentally implement and evaluate the top candidate in CHO cells.

The experimental study is performed in three stages (FIG. 1). Essential metabolic reactions are identified that are candidate targets for designing new and potentially superior selection systems using network-wide deletion analysis and using our proprietary reconstructed model of CHO metabolism. The candidate targets are rank-ordered and prioritized based on a number of criteria, including the predicted stringent specificity of the new selection system and improved cell physiology using computational tools. The top candidate selection system is experimentally implemented in the CHO-S cell line by: (a) creating an auxotrophic clone, (b) transiently transfecting cells with a selection vector that includes an antibody-expressing gene, and (c) selecting protein producing cell lines based on their auxotrophy. The development and implementation of a model-based selection system is evaluated in CHO cells by comparing experimentally generated cell culture data with those calculated by the reconstructed model. Successful completion of this validation study provides a demonstration of the scientific and technical feasibility of the integrated platform for design of new and superior metabolic selection systems in mammalian based protein production.

Identify and Prioritize New Selection Systems in Chinese Hamster Ovary Cell Line Using a Reconstructed Metabolic Model. Using a reconstructed and validated model of CHO metabolism, essential metabolic reactions that are candidate targets for designing new selection systems in CHO cell lines are identified using an in silico deletion study (see above) (Altamirano et al., *Biotechnol. Prog.* 17:1032-1041 (2001); Browne and Al-Rubeai, *Trends Biotechnol.* 25:425-432 (2007)). A network-wide single- and double-reaction deletion analysis is performed by removing the corresponding reactions from the network while simulating growth, as described in the Preliminary Studies section. The results from this in silico deletion study provide a list of: (i) single target reactions, which are essential (required for growth), and (ii) two-reaction deletions that are fatal to the cell (synthetic lethals) (Step 1, FIG. 2). Only deletion of target reactions that generate true lethal deletion strains (strains with deleted essential genes and synthetic lethalities) are further analyzed within the CHO metabolic network in SimPheny™.

Once a list of single and double lethal deletions are identified, a subset of the in silico deletion strains is identified for which growth can be restored under an auxotrophic condition, i.e. by adding a precursor metabolite (i.e. nucleotide, vitamin or amino acid) to the chemically defined CHO cell growth medium. Such precursor metabolites are evaluated and ranked based on the knowledge of their transport systems, the cost, availability and safety of these metabolites to be used in industrial protein production (Step 2, FIG. 2).

In order to identify a superior selection system compared to existing ones, the methods are used to find a metabolic marker, which is a selection marker of true auxotrophy (described above) and a marker of improved metabolism. An existing example of the selection system of interest is the GS selection system, the presence of which induces cell growth in the absence of glutamine and reduced production of toxic ammonia (Walsh, *Nat. Biotechnol.* 21:865-870 (2003)). To identify additional selection systems, additional computational analyses are performed to determine the metabolic network response to the changes (i.e. increase or decrease) imposed on a flux through a particular reaction of interest. In this study Robustness Analysis is used (Lakshmi Kamath, *Drug Discovery & Development,* 1-12-2005) to identify target reactions through which constrained higher flux can improve CHO cell line metabolic properties, e.g. to reduce toxic byproduct production, reduce wasteful energy metabolism, reduce alanine overflow or improve monoclonal antibody productivity (Step 3, FIG. 2) (Altamirano et al., *Biotechnol. Prog.* 17:1032-1041 (2001); Wurm, F. M., *Nat. Biotechnol.* 22:1393-1398 (2004)). These target reactions are rank-ordered based on their potential benefits to metabolic characteristic of cell culture. Results identified by Robustness Analysis for increasing flux through a reaction are implemented by transfecting the auxotrophic CHO cell line with the selection marker gene that is placed under a strong promoter, such as the hCMV promoter, that has successfully been used in mammalian cell line applications, including GS selection system design (Jayapal et al., *Chem. Eng. Progress* 103:40-47 (2007)). Other strong promoters can additionally be used. Alternatively, less active promoters can be used if over-expression of the gene product of interest proves to be toxic to the cells.

Figure 2:
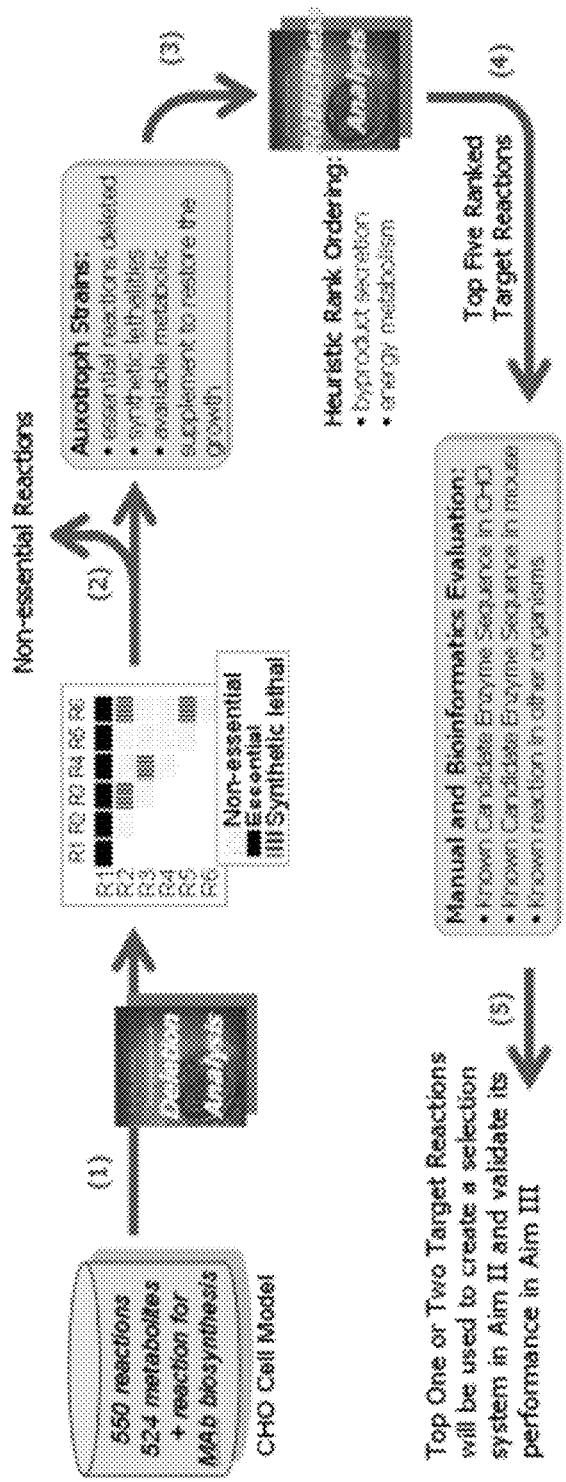
FIG. 2 shows that deletion analysis can be performed on CHO metabolism when the gene is present in the genome (Step 1). Metabolic target reactions, deletion of which would create true auxotrophs can be identified (Step 2). Target reactions can be analyzed using Robustness Analysis for superior selection system design, for example, in SimPheny™ (Step 3) and top five candidates can be subjected to manual and bioinformatics evaluation (Step 4). Top one or two target reactions (one essential reaction or one synthetic lethality of two target reactions) can be selected for one experimental selection system design (Step 5).

Finally, top target metabolic reactions are further subjected to manual and bioinformatics evaluation (Step 4, FIG. 2). First, the number of (iso-)enzymes catalyzing the target reaction of interest are identified using previous publications on CHO cell line physiology and metabolism, and CHO EST genome sequence library (Seth et al., *Curr. Opin. Biotechnol.* 18:557-564 (2007)). Chinese Hamster genome sequence annotation has not yet been published. Sequence comparison of CHO EST library to the GenBank database has shown that mouse is the best model organism with complete genetic and sequence information that can be used for comparative analysis for the CHO cell line (Seth et al., *Curr. Opin. Biotechnol.* 18:557-564 (2007)). Thus, if none of top target gene sequences is known specifically for Chinese Hamster, or cannot be determined using bioinformatics tools, mouse and hamster sequences having similarity to experimentally determine sequences of Chinese Hamster target genes are used (see below). Using bioinformatics tools and published literature, the presence of multiple copies of the target genes that may be present in Chinese Hamster genome is also investigated. Since CHO cells are known to be functionally hemizygous for many genes primarily due to gene inactivation (Page and Sydenham, *Biotechnology* 9:64-68 (1991); Cockett et al., *Biotechnology* 8:662-667 (1990)), it is expected that experimental implementation of the candidate selection system will require deletion of only one or two genes, thus simplifying the effort required in developing true auxotrophic clones. Candidate targets are rank ordered based on the known or predicted number of target (iso-)genes and their known or predicted sequences in Chinese Hamster genome. The top candidate target identified are experimentally implemented to create a metabolic selection system in CHO cell line.

Experimental Implementation of Top Candidate Selection System in CHO Cell Line. To experimentally validate the computational approach, the candidate selection system is created in a CHO-S cell line. CHO-S cells are a subclone of the parental CHO cell line, which have been adopted to grow in suspension and can produce monoclonal antibodies in serum-, hydrolysate-, and protein-free chemically defined media. In addition, CHO-S are available commercially (Invitrogen, Carlsbad Calif.). Deletion of the target gene and insertion of a tag such as the GFP tag is performed using a zinc-finger nuclease (ZFN) system available through Sigma-Aldrich (Urlaub and Chasin, *Proc. Natl. Acad. Sci. U.S.A.* 77:4216-4220 (1980)). Custom service is available (Sigma-Aldrich) using an algorithm to in silico design several ZFN candidates, including all necessary ZNF assembly and DNA binding testing to select the best ZFN pair. ZFN technology uses a general solution using a combination of two fundamental biological processes: DNA recognition by C2H2 zinc-finger proteins and repair of DNA double-strand breaks using non-homologous end joining (NHEJ) or using homology dependent repair (HDR). The zinc finger nuclease (ZFN) driven targeted gene disruption and sight-specific gene insertion technology are used to disrupt and inactivate the gene that codes for the target reaction and simultaneously introduce the GFP tag to the deletion strains (first scheme, FIG. 3) (Urlaub and Chasin, *Proc. Natl. Acad. Sci. U.S.A.* 77:4216-4220 (1980); Zhang et al., *Cytotechnology* 51:21-28 (2006)). Previous studies have shown that ZFN-mediated gene disruption or targeted gene insertion is a robust and general method for targeted and precise genome editing in mammalian cells and ZFN-targeted GFP integration in CHO cell line has a frequency of insertion of up to 13% (Kingston et al., *Current Protocols in Molecular Biology*, John Wiley & sons, Inc., (1993); Browne and Al-Rubeai, *Trends Biotechnol.* 25:425-432 (2007); Price and Palsson, *Nat. Rev. Microbiol.* 2:886-897 (2004); Santiago et al., *Proc. Natl. Acad. Sci. U.S.A.* 105:5809-5814)). ZFN-based gene deletion has proven to be more effective than temporary 'knock down' approaches based on small molecule inhibitors, zinc finger transcription factors, antibodies, antisense, or RNAi. Also, only transient ZFN expression is required to generate permanent gene deletions (Urlaub and Chasin, *Proc. Natl. Acad. Sci. U.S.A.* 77:4216-4220 (1980); Urnov et al., *Nature* 435:646-651 (2005); Polastro and Tulcinsky, *Scrip Magazine* (August 2002)). Compared with gene addition via random integration, ZFN-based technology provides robust, targeted, and precise gene insertions (Zhang et al., *Cytotechnology* 51:21-28 (2006)). Overall, ZFN-based technology generally generates quicker, permanent, and higher probability gene manipulation results compared with other available mammalian cell engineering technologies. However, other such technologies can be used, if desired.

To create a gene deletion clone for the target gene sequence selected, a pair of ZFNs is designed that specifically bind to the sequence of target gene exon, disruption of which would disrupt the target gene expression. If the results of the manual and bioinformatics evaluation were inconclusive regarding Chinese Hamster target gene sequence, genomic DNA fragment are cloned from the Chinese Hamster Ovary cell line (based on mouse genome sequence) and the nucleotide sequence of a stretch of DNA that encompasses the complete sequence of the target gene is determined. The intron/exon boundaries are identified by RT-PCR following GT/AG rule and the exon sequence are used for the design of ZFNs. The homologous donor plasmid that contains GFP cDNA, or other desired marker, is engineered flanked by 750-bp stretches of sequence that are homologous to the target locus and that surround double strand break introduced by ZFN. Next, CHO cells are transfected with the donor plasmid carrying GFP tag and ZFNs. During ZFN-induced homologous DNA repair, the GFP is inserted at the cleavage site of the target gene and the expression of the target gene is disrupted.

Following cell transfection, CHO cells are cultivated in completely supplemented medium with all the ingredients that are required for the created auxotrophs to grow. CHO cells that express GFP will be selected using fluorescence-activated cell sorting (FACS) (Step 1, FIG. 3). Repeated rounds of selected GFP-tagged cell cultivation and FACS sorting are performed to select for the highest levels of GFP-driven fluorescence, and clonal GFP-expressing cell lines are produced. The GFP tag was chosen to use as a screening/selection marker rather than antibiotic resistance or limiting dilution cloning (LDC) approaches, since the GFP-based method performs faster and more cells can be screened at a time (Pissarra, *Nat. Biotechnol.* 22:1355-1356 (2004)). Also, GFP has no known negative impact on cell growth and metabolism. In contrast, antibiotic based selection slows down cell growth and requires additional time for cell recovery. A single FACS sorting using GFP-tag selection system can generate clonal transfected cell culture approximately 10 times faster compared with LDC selection approach (Pissarra, *Nat. Biotechnol.* 22:1355-1356 (2004)) and can generate a cell pool that has 38 times increased specific productivity (Rose and Ramakrishnan, *Handbook of Industrial Cell Culture*, Vinci, V. and Pareh, S. (eds.), Humana Press, Totowa, pp. 69-103 (2003)). The GFP-tagged FACS sorting studies have shown that the generation of clonal cell lines is not a requirement for achieving high-level expression, even though the current generation of cell sorters does allow for single-cell cloning (Ayusawa et al., *Cell Genet.* 7:523-534 (1981)). If found necessary clonal cell lines can be produced using other well known methods.

Clonal GFP expressing cells selected by FACS analysis are tested to determine whether the target gene has been successfully disrupted. To confirm that the target gene is disrupted and does not express functional enzyme, the cDNA is sequenced, or polymorphisms in the target gene or RNA are examined. Additionally, cells can be examined for loss of the target protein using antisera. Non-transfected CHO cells are used as a negative control. Available assays such as enzymatic assays can be used to verify that the target reaction is inactivated. Finally, selective plating assays can be used with or without supplemental nutrient to verify that the created deletion strain is a true auxotroph and grows only when supplemental nutrient is added. The results from these experiments ensure that the target gene has been deleted, the target reaction has been inactivated and true metabolic nutrient auxotroph has been created.

Figure 3:
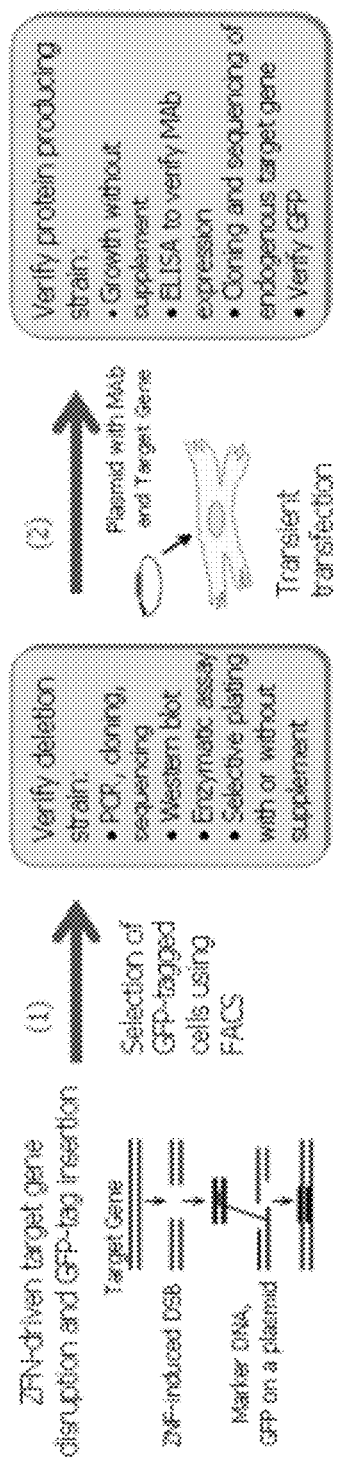
FIG. 3 shows that a metabolic auxoroph and GFP-tagged CHO cell can be created using, for example, ZFN-based technology (Zhang et al., Cytotechnology 51:21-28 (2006)). GFP expressing CHO cells can be selected using, for example, FACS (Step 1). The target gene disruption will be verified using various molecular biology tools, the true auxotroph can be transiently transfected with selection vector expressing target gene i.e. selection marker gene and monoclonal antibody coding genes (Step 2) and the transfected cells can be selected in media deficient for a metabolite complementation and tested for monoclonal antibody production.

Experimentally validated true auxotrophs are transiently transfected with 2 µg of two monoclonal antibody expressing plasmids in which one contains an expression cassette for the antibody light chain and the other contains a cassette for the antibody heavy chain and a cassette for the deleted target gene expression (Step 2, FIG. 3). If Robustness Analysis predicts that amplification of the target gene benefits cell characteristics, a strong promoter is used to over-express the target gene, i.e. the selection marker aiming to improve metabolic properties of the cell. CHO cells transfected with plasmids expressing both a monoclonal antibody and the target selection marker are expected to retain co-selection in the absence of supplemental nutrient. After two weeks, stable monoclonal antibody production is generated in this cell line and antibody expression is verified using ELISA according to manufactures protocol (Bethyl Laboratories). Additional tests, such as screening for GFP expression and sequencing of endogenous target gene, can be performed to verify that the endogenous target gene remains disrupted in the final CHO cell culture (Step 2, FIG. 3). Alternatively to a full monoclonal, FAb fragments, which corresponds to the binding end of an antibody, is expressed in CHO cells. FAb fragments can be expressed as a single gene and this will simplify experimental work and still be sufficient to validate the method.

Evaluate the Development and Implementation of a Model-based Selection System in CHO Cell Line. Once the model-based selection system is implemented in CHO cell line, experimentally generated cell culture data will be compared with those calculated by the reconstructed model (FIG. 1). For this purpose, the selected (deletion and protein producing) cell lines generated are characterized in batch spinner flask cultivations in a chemically defined CHO cell line medium. The only difference between these two cultivations will be a supplemental nutrient that is added to the deletion CHO cell line cultivation media. The two CHO cell lines are grown in batch-type cultivations until steady state is reached. Throughout the exponential growth phase, culture samples are taken for cell count and cell viability testing. Extracellular metabolite concentrations are measured using analytical detection capabilities, i.e. liquid chromatography-mass spectrometry (LCMS), gas chromatography MS (GCMS) and high performance liquid chromatography (HPLC). Using collected experimental data, carbon balance, cell specific growth rate, substrate uptake and byproduct production rates are calculated for the deletion and protein producing strain. In addition, recombinant protein production can be measured throughout the range of growth by an ELISA test. Through the computational analysis, simulations that represent CHO deletion and protein producer strains are generated. Experimentally generated values are qualitatively compared with SimPheny™-generated predictions for the deletion and protein producing CHO cell lines. These results are used to qualitatively corroborate the capability of the computational modeling approach to design selection systems and predict their effects on cell metabolism and protein production.

In summary, designing effective selection systems using a combination of the computational platform in SimPheny™, and advanced ZNF-based gene deletion and cell transfection technology are described above (Urlaub and Chasin, *Proc. Natl. Acad. Sci. U. S. A* 77:4216-4220 (1980); Browne and Al-Rubeai, *Trends Biotechnol.* 25:425-432 (2007)). The results of the method are confirmed by the ability to computationally identify and experimentally validate a selection system in CHO cell line, focused on targets with added metabolic advantages such as reduced byproduct formation and increased growth rate. The attainment of these goals allows further development and improvement of the best resulting new selection system and experimentally evaluate other targets.

EXAMPLE II

Model-Based Selection System Design

Figure 4:
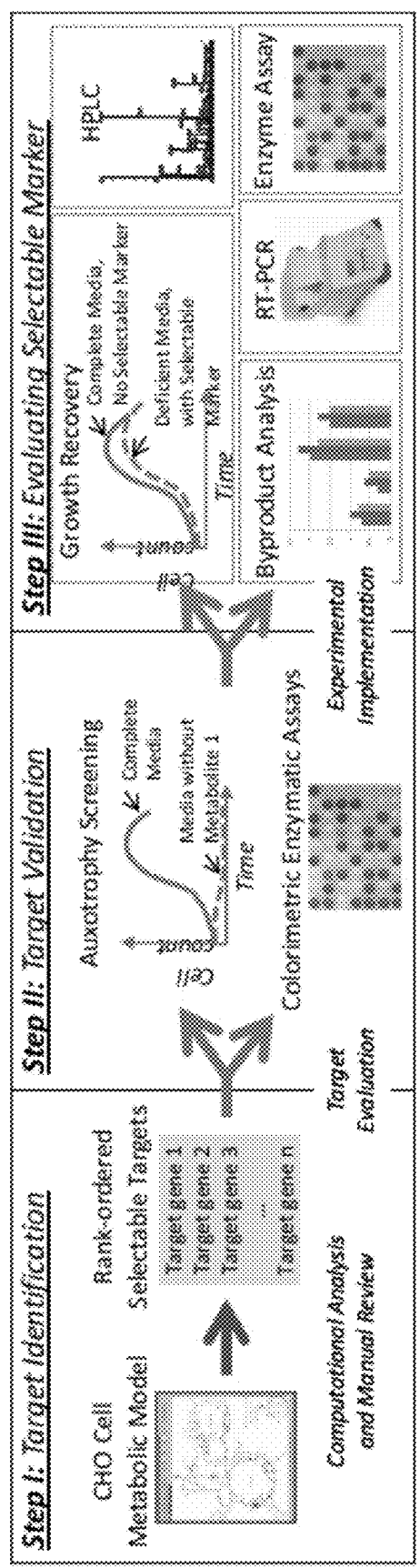
FIG. 4 shows a schematic diagram of the steps for identifying model-based selectable markers. Step I involves target identification, Step II involves target validation, and Step III involves evaluating the target as a selectable marker system.

This example describes the identification and development of model-based selectable markers in CHO cell lines. This example demonstrates the feasibility of identifying new selection systems in CHO cell lines using an integrated computational and experimental approach. The study is performed in three stages (FIG. 4). In Step I (FIG. 4), essential metabolic reactions were computationally identified that are candidate targets for designing selection systems, using a network-wide deletion analysis and reconstructed model of CHO metabolism. The candidate targets were rank-ordered and prioritized based on a number of criteria (detailed below). In Step II (FIG. 4), an initial set of top candidate selection markers were validated experimentally using auxotrophic screening and enzymatic assays in CHO cell culture. In Step III (FIG. 4), cells were transfected with vectors containing two of the exemplary designs, and a comprehensive study was performed to demonstrate and characterize cell line selection. Experimental results showed that the most extensively characterized selection marker exhibited higher integrated viable cell density (IVCD) and lower peak byproduct concentration than the parental cell line. Successful completion of this validation study provides a clear demonstration of new and superior metabolic selection systems in mammalian cell lines.

Figure 5:
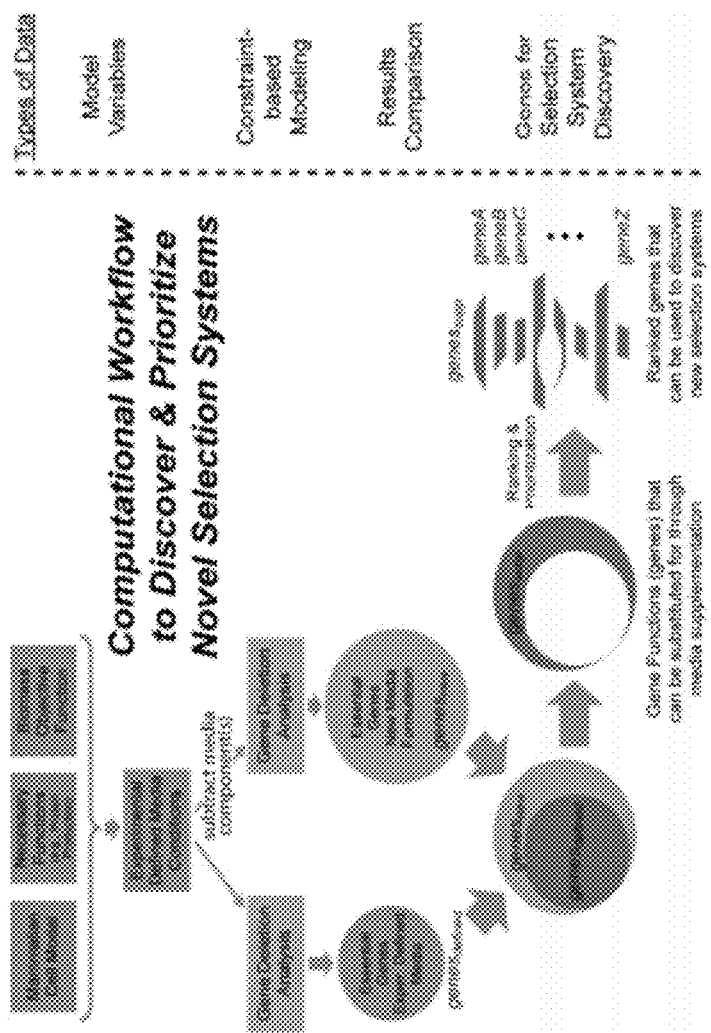
FIG. 5 shows a schematic diagram of the computational approach used to determine new selectable markers using a constraint-based modeling approach. Modeling variables, including a genome-scale model and industry-relevant culture conditions, were used to perform two gene deletion analyses. One gene deletion is performed in a media condition missing one or more metabolites. Through comparison of results, genes that can be substituted through media supplementation (genes$_{supp}$) are identified, ranked, and prioritized to discover new selectable markers. The computational algorithm can be run for multiple media component conditions removed at one time, or one or more in combination.

Computational Approach to Identify Selectable Markers in CHO Cell Lines. Using a reconstructed model of CHO metabolism and computational modeling tools (see Example I), a model-based approach was developed to identify new metabolic targets in CHO cell lines (FIG. 5). In silico targets were identified by performing a network-wide deletion analysis to identify the essential reactions in the model when the media components were systematically removed from the simulated conditions (computationally, each deletion analysis was performed by removing one reaction from the network, removing one metabolite from the media, and maximizing the flux for cell biomass and monoclonal antibody production).

Each simulated deletion was performed in two in silico media conditions: (i) the complete CHO cell culture media (as described in the literature and verified analytically), and (ii) media lacking one (or two) media components that can be used for selection of the CHO cell line lacking specific gene product activities. In this analysis, a total of 31 substrates were considered for media removal, including media nutrients such as carbohydrates and amino acids. Out of 31 metabolites, 12 were identified to restore growth and productivity when one of 32 gene functions in the CHO model was removed (Table 1). The model was then used to determine: (i) the flux of the target reaction required for cell growth (with higher flux reactions given preference as they could lead to higher expression of a coupled gene product), and (ii) the growth rate after the reaction is removed and a supplemental metabolite was added to the medium (with a high value being desirable and indicating a more essential metabolic flux for cell growth). Computational prioritization was performed using a computational robustness analysis, as described elsewhere (Edwards and Palsson, *Biotechnol. Prog.* 16:927-939 (2000)). The algorithm developed in this study was designed to be easily scalable and appropriate for application to any genome-scale model, including a model of an NS0 cell line (36 gene functions, 6 different metabolites) (see WO 2010/098865, filed Feb. 26, 2010), or other suitable in silico cell models.

TABLE 1

Computationally-identified selectable markers.*

| Targets | Media Complementation | Accession No. |
|---|---|---|
| Category I: | | |
| 1. ARGSL—argininosuccinate lyase | Arg—Arginine | hsa: 435; mmu: 109900; rno: 59085; NM_000048.3 (GI: 68303544); NM_001024943.1 (GI: 68303541); NM_001024944.1 (GI: 68303546); NM_001024946.1 (GI: 68303548); NM_133768.4 (GI: 153792560); NM_021577.3 (GI: 148747348) |
| 2. CYSTGL—cystathionine G-lyase | Cys—Cysteine | hsa: 1491; mmu: 107869; rno: 24962. NM_001190463.1 (GI: 299473758); NM_001902.5 (GI: 299473757); NM_153742.4 (GI: 299473760); NM_145953.2 (GI: 31981852); NM_017074.1 (GI: 8393214) |
| 3. CYSTS—cystathionine b-synthase | Cys—Cysteine | hsa: 875; mmu: 12411; rno: 24250; NM_000071.2 (GI: 209862802); NM_001178008.1 (GI: 295821199); NM_001178009.1 (GI: 295821201); NM_144855.2 (GI: 118130062); NM_178224.2 (GI: 118130577); NM_012522.2 (GI: 158186658) |
| 4. GMTR—glycine N-methyltransferase | Cys—Cysteine | hsa: 27232; mmu: 14711; rno: 25134; NM_018960.4 (GI: 54792737); NM_010321.1 (GI: 6754025); NM_017084.1 (GI: 8567353) |
| 5. P5CS—pyrroline-5-carboxylate synthetase | Pro—Proline | hsa: 5832; mmu: 56454; rno: 361755; NM_001017423.1 (GI: 62912456); NM_002860.3 (GI: 62912455); NM_019698.2 (GI: 255958291); NM_153554.2 (GI: 255958293); NM_001108524.1 (GI: 157823606) |
| 6. PHE4MO—phenylalanine 4-monooxygenase | Tyr—Tyrosine | hsa: 5053; mmu: 18478; rno: 24616; NM_000277.1 (GI: 4557818); NM_008777.3 (GI: 171543885); NM_012619.2 (GI: 158262032) |
| 7. CBPSAm—carbamoyl-phosphate synthase (ammonia) | Arg—Arginine | hsa: 1373; mmu: 227231; rno: 497840; NM_001122633.1 (GI: 327532712); NM_001122634.1 (GI: 170295796); NM_001875.3 (GI: 169790913); NM_001080809.1 (GI: 124248511); NM_017072.1 (GI: 8393185) |
| 8. OCBTm—ornithine carbamoyltransferase, mitochondrial | Arg—Arginine | hsa: 5009; mmu: 18416; rno: 25611; NM_000531.5 (GI: 197116380); NM_008769.3 (GI: 141803523); NM_013078.1 (GI: 6981311) |
| 9. ORNTAm—ornithine transaminase, mitochondrial | Arg—Arginine | hsa: 4942; mmu: 18242; rno: 64313; NM_000274.3 (GI: 284507296); NM_001171814.1 (GI: 284507297); NM_016978.2 (GI: 134032004); NM_022521.2 (GI: 40254768) |
| 10. METAT—methionine adenosyltransferase | Cys—Cysteine | hsa: 27430; hsa: 4144; hsa: 4143; mmu: 108645; mmu: 11720 mmu: 232087; rno: 683630; rno: 171347; rno: 25331; NM_013283.3 (GI: 33519456); NM_182796.1 (GI: 33519454); NM_005911.4 (GI: 46852159); NM_000429.2 (GI: 67906818); NM_134017.1 (GI: 19527233); NM_133653.2 (GI: 118130982); NM_145569.4 (GI: 146149255); NM_001044282.1 (GI: 112983991); NM_134351.1 (GI: 19705456); NM_012860.2 (GI: 77157804) |
| 11. AHC—adenosylhomocysteinase | Cys—Cysteine | hsa: 10768; hsa: 23382 hsa: 191; mmu: 677344; mmu: 74340; mmu: 229709; mmu: 269378; rno: 362013; rno: 29443; rno: 312192; NM_006621.4 (GI: 111120323); NM_001130720.2 (GI: 298286486); NM_001130722.2 (GI: 298286488); NM_001130723.2 (GI: 298286490); NM_015328.3 (GI: 298286487); NM_000687.2 (GI: 239937553); NM_001161766.1 (GI: 239937450); XM_001002625.2 (GI: 149267882); NM_001171000.1 (GI: 283837829); NM_001171001.1 (GI: 283837831); NM_021414.5 (GI: 283837827); NM_145542.3 (GI: 144922632); NM_016661.3 (GI: 262263371); NM_001108561.1 (GI: 157819078); NM_017201.1 (GI: 8392877); XM_231564.6 (GI: 295852411) |

TABLE 1-continued

Computationally-identified selectable markers.*

| Targets | Media Complementation | Accession No. |
|---|---|---|
| 12. PPCOACrm—propionyl-CoA carboxylase, mitochondrial | Cys—Cysteine | hsa: 5096; hsa: 5095; mmu: 110821; mmu: 66904; rno: 24624; rno: 687008; NM_000532.4 (GI: 295821214); NM_001178014.1 (GI: 295821215); NM_000282.3 (GI: 295821180); NM_001127692.2 (GI: 295821181); NM_001178004.1 (GI: 295821182); NM_144844.2 (GI: 254540161); NM_025835.2 (GI: 142348575); NM_017030.2 (GI: 148747118); NM_019330.1 (GI: 158303307) |
| 13. MMEm—methylmalonyl-CoA epimerase, mitochondrial | Cys—Cysteine | hsa: 84693; mmu: 73724; rno: 293829; NM_032601.3 (GI: 188035927); NM_028626.1 (GI: 58037328); NM_001106341.1 (GI: 157821868) |
| 14. MMMrm—methylmalonyl-CoA mutase | Cys—Cysteine | hsa: 4594; mmu: 17850; NM_000255.3 (GI: 296010795); NM_008650.3 (GI: 295789163) |
| 15. MI1PS—myo-Inositol-1-phosphate synthase | Myo-inositol | hsa: 51477; mmu: 71780; rno: 290651; NM_001170938.1 (GI: 283135175); NM_001170939.1 (GI: 283135177); NM_016368.4 (GI: 283135174); NM_023627.1 (GI: 12963756); NM_001013880.2 (GI: 189163480) |
| 16. TMDSr—thymidylate synthase | Thymidine | hsa: 7298; mmu: 22171; rno: 29261; NM_001071.2 (GI: 186972144); NM_021288.4 (GI: 292494928); NM_019179.1 (GI: 9507216) |
| 17. NDP8—nucleoside-diphosphatase (dUDP) | Thymidine | hsa: 256281; hsa: 55190; hsa: 11163; hsa: 11165; hsa: 83594; mmu: 67993; mmu: 58242; mmu: 71207; mmu: 66174; rno: 294292; rno: 94267; rno: 299346; rno: 367323; NM_177533.3 (GI: 223718030); NM_018159.3 (GI: 134288878); NM_019094.4 (GI: 98985815); NM_199040.2 (GI: 98985816); NM_006703.2 (GI: 37622350); NM_031438.2 (GI: 37574615); NM_026497.2 (GI: 142375040); NM_021431.2 (GI: 72384358); NM_027722.4 (GI: 169808396); NM_025399.3 (GI: 146134990); NM_001024243.1 (GI: 66730446); NM_053598.1 (GI: 16758971); NM_001106760.1 (GI: 157822974); NM_001109010.1 (GI: 157823878) |
| 18. HCO3Em—carbonate anhydrase | Cys—Cysteine | hsa: 11238; hsa: 23632; hsa: 377677; hsa: 759; hsa: 760; hsa: 761; hsa: 762; hsa: 763; hsa: 765; hsa: 766; hsa: 767; hsa: 768; hsa: 771; mmu: 12319; mmu: 12346; mmu: 12349; mmu: 12350; mmu: 12351; mmu: 12352; mmu: 12353; mmu: 12354; mmu: 230099; mmu: 23831; mmu: 56078; mmu: 71934; mmu: 76459; mmu: 80733; rno: 288360; rno: 291819; rno: 29242; rno: 297814; rno: 298657; rno: 302669; rno: 310218; rno: 313495; rno: 363085; rno: 499566; rno: 54231; rno: 54232; rno: 54233; rno: 791259; NM_007220.3 (GI: 95147552); NM_012113.1 (GI: 6912283); NM_198584.2 (GI: 187607285); NM_001128829.2 (GI: 258679486); NM_000067.2 (GI: 157952216); NM_005181.3 (GI: 208609975); NM_000717.3 (GI: 187608493); NM_001739.1 (GI: 4502520); NM_001215.2 (GI: 70167126); NM_001014435.1 (GI: 62240988); NM_004056.4 (GI: 56121820); NM_001216.2 (GI: 169636419); NM_001218.3 (GI: 45935381); NM_007592.3 (GI: 86439975); NM_001083957.1 (GI: 145301560); NM_009801.4 (GI: 157951595); NM_007606.3 (GI: 118131196); NM_007607.2 (GI: 239787095); NM_007608.2 (GI: 112181174); NM_009802.2 (GI: 157951677); NM_053070.3 (GI: 156139072); NM_139305.2 (GI: 145046219); NM_011797.2 (GI: 133892566); NM_181315.4 (GI: 211057395); NM_024495.5 (GI: 240120060); NM_178396.4 (GI: 227496586); NM_030558.2 (GI: 31981403); NM_001105901.1 (GI: 157787055); NM_001106165.1 (GI: 157818126); NM_019174.1 (GI: 9506448); NM_001009662.1 (GI: 57527116); NM_001134841.1 (GI: 198386348); NM_001005551.1 (GI: 53850631); NM_001107660.1 (GI: 157817868); NM_001107956.1 (GI: 157818644); NM_001080756.1 (GI: 124249067); NM_001134993.1 (GI: 201860291); NM_019291.1 (GI: 9506444); NM_019292.4 (GI: 148747280); NM_019293.1 (GI: 9506450); NM_001109655.2 (GI: 157952204) |
| 19. ADNK1—adenosine kinase | Cys—Cysteine | hsa: 132; mmu: 11534; rno: 25368; NM_001123.2 (GI: 32484972); NM_006721.2 (GI: 32484974); NM_134079.3 (GI: 146149178); NM_012895.3 (GI: 52345434) |
| 20. SARCOp—sarcosine oxidase | Cys—Cysteine | hsa: 51268; mmu: 19193; rno: 303272; NM_016518.2 (GI: 60499000); NM_008952.2 (GI: 158854013); NM_001012009.1 (GI: 58865585) |
| 21. AKBDHm—alphaketobutyrate dehydrogenase, mitochondrial | Cys—Cysteine | — |
| 22. PSERD_CHO—phosphatidylserine decarboxylase | Ethanolamine | hsa: 23761; mmu: 320951; NM_014338.3 (GI: 34147578); NM_177298.3 (GI: 126722756) |

TABLE 1-continued

Computationally-identified selectable markers.*

| Targets | Media Complementation | Accession No. |
|---|---|---|
| 23. PGI—glucose-6-phosphate isomerase | Glucose | hsa: 2821; mmu: 14751; rno: 292804; NM_000175.3 (GI: 296080694); NM_001184722.1 (GI: 296080692); NM_008155.3 (GI: 254553457); NM_207592.1 (GI: 46485439) |
| 24. MI1PP—myo-inositol 1-phosphatase | Mio-inositol | hsa: 3612; hsa: 3613; mmu: 114663; mmu: 55980; rno: 282636; rno: 83523; NM_001144878.1 (GI: 221625486); NM_001144879.1 (GI: 221625506); NM_005536.3 (GI: 221625478); NM_014214.1 (GI: 7657235); NM_053261.2 (GI: 118131116); NM_018864.5 (GI: 239985484); NM_172224.1 (GI: 26449165); NM_032057.1 (GI: 14091735) |
| 25. RNDR4—ribonucleoside-diphosphate reductase | Thymidine | hsa: 50484; hsa: 6241; hsa: 6240; mmu: 382985; mmu: 20135; mmu: 20133; rno: 685579; rno: 299976; rno: 362720; NM_001172477.1 (GI: 289177073); NM_001172478.1 (GI: 289177075); NM_015713.4 (GI: 289177072); NM_001034.3 (GI: 260064011); NM_001165931.1 (GI: 260064012); NM_001033.3 (GI: 157266329); NM_199476.1 (GI: 41054951); NM_009104.2 (GI: 237512999); NM_009103.3 (GI: 254750731); NM_001013236.1 (GI: 61557387); NM_001130543.1 (GI: 194474071); NM_001025740.1 (GI: 71043759) |
| 26. DHPRx—dihydropteridine reductase | Tyr—Tyrosine | hsa: 5860; mmu: 110391; rno: 64192; NM_000320.2 (GI: 208973245); NM_024236.2 (GI: 256574769); NM_022390.1 (GI: 11693159) |
| Category II: | | |
| 27. ARGSS—argininosuccinate synthase | Arg—Arginine | hsa: 445; mmu: 11898; rno: 25698; NM_000050.4 (GI: 113204625); NM_054012.3 (GI: 113204624); NM_007494.3 GI: 133893196; NM_013157.3 (GI: 148747445) |
| 28. ASNS1—asparagine synthase (glutamine-hydrolyzing) | Asn—Asparagine | hsa: 440; mmu: 27053; rno: 25612; NM_001178075.1 (GI: 296010847); NM_001178076.1 (GI: 296010849); NM_001178077.1 (GI: 296010851); NM_001673.4 (GI: 296010844); NM_133436.3 (GI: 296010846); NM_183356.3 (GI: 296010845); NM_012055.3 (GI: 146134364); NM_013079.2 (GI: 148747575) |
| 29. FldAct—formaldehyde activation (spontaneous) | Cys—Cysteine | — |
| 30. GLNS—glutamine synthase (GS) | Glu—Glutamine | hsa: 2752; mmu: 14645; rno: 24957; NM_001033044.2 (GI: 260593718); NM_001033056.2 (GI: 260593719); NM_002065.5 (GI: 260593717); NM_008131.3 (GI: 118130944); NM_017073.3 (GI: 142349611) |
| 31. G5SADs—L-glutamate 5-semialdehyde dehydratase (spontaneous) | Pro—Proline | — |
| 32. DHFR—dihydrofolate reductase | Thymidine | hsa: 200895; hsa: 1719; mmu: 13361; NM_176815.3 (GI: 142360382); NM_000791.3 (GI: 68303806); NM_010049.3 (GI: 68299777) |

*Selectable marker names are based on commonly used gene names.
Lower case letters 'm' at the end of the selectable marker names indicates organelle, in which these selectable marker enzymes are active: m—mitochondria, x—peroxisome.
Lower case 'r' indicates that the reaction is defined to be reversible.

Manual Review of Candidate Selection Systems. Candidate selectable markers identified by the model were manually reviewed and assigned a final prioritization score using the following criteria: (1) the number of genes encoding isozymes for the targeted metabolic reaction, based on the CHO, mouse, human, and rat genomic information, (2) presence or absence of the target reaction in CHO cell lines (due to genetic mutation or gene loss) based on published CHO literature, (3) presence of possible transport mechanisms for supplemented metabolites, and (4) computational scoring of the target reactions, as described in the previous section. The candidate selectable markers were ranked as follows (target/complementation): P5CS—pyrroline-5-carboxylate synthetase/proline (Pro); PHE4MO—phenylalanine 4-monooxygenase/tyrosine (Tyr); ARGSL—argininosuccinate lyase/arginine (Arg); CYSTGL—cystathionine G-lyase/cysteine (Cys); CYSTS—cystathionine b-synthase/cysteine; GMTR—glycine N-methyltransferase/cysteine).

Among identified target reactions/gene functions, 26 were identified to belong to Category I (previously unknown as selectable markers), and 6 were identified to belong to Category II (see Table 1). Within Category II there are 6 targets that are (a) being currently used as a validated selection system, or (b) being a non-enzymatic reaction that can occur spontaneously in the cell. Thus, the methods correctly identified previously known selectable markers such as dhfr, glutamine synthetase, arginosuccinate synthase and asparagine synthase (glutamine-hydrolyzing) (see U.S. publication 2004/0148647). A total of 6 targets were selected for experimental validation from Category I. For initial studies, targets were selected for further validation mainly due to computational and literature evidence suggesting that their enzymatic function is naturally absent in the cell (due to genetic mutations or gene loss), eliminating the need for creating gene knock-outs in this study. However, as described above and in Example III, such gene knockouts can be readily prepared using well known methods.

Experimental Target Validation. To experimentally validate targets identified by the model, a comprehensive target validation study was performed to demonstrate the lack of metabolic function in the cell. For this purpose, an auxotrophy screening test was initially performed by removing one media component at a time. Briefly, custom Opti-CHO media (Invitrogen) was ordered without arginine, cysteine, proline and tyrosine ('Cust-AA', used as the negative control, FIG. 6). All metabolites were then added back to serve as a complete media ('Cust-FAX, used as the positive control), and four test media were developed each lacking one of the four metabolites (e.g. 'No Pro', media with no proline). CHO-K1 and CHO-S cells were seeded at $0.5 \times 10^6$ cells/mL in media with and without the test components in duplicate shake flasks. The flasks were sampled for viable cell density and percent viability once every other day, for ten days or until viability dropped below 5%.

Figure 6:
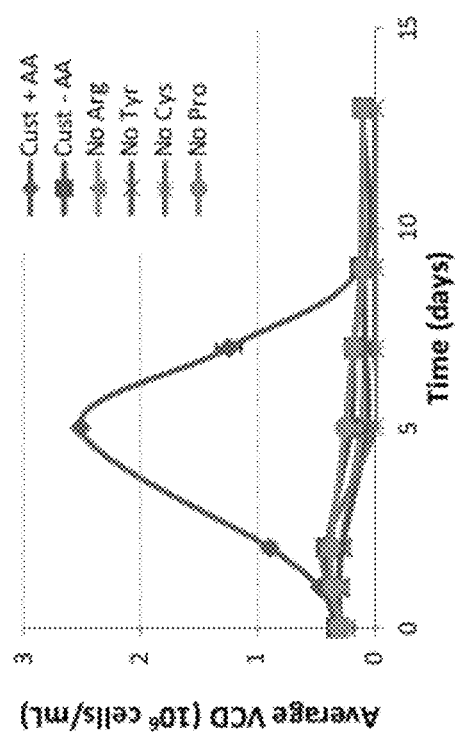
FIG. 6 shows a graphical representation of the average viable cell density (cells/mL) plotted over time (days) for CHO-S cells. VCD, viable cell density; AA, amino acids arginine (Arg), tyrosine (Tyr), cysteine (Cys), and proline (Pro); Cust+AA, complete media (positive control); Cust−AA, media deficient in Arg, Tyr, Cys, and Pro (negative control); No Arg, media without arginine; No Tyr, media without tyrosine; No Cys, media without cysteine; No Pro, media without proline.

The results show that the cells are auxotrophic for arginine, cysteine, proline and tyrosine (data shown only for CHO-S cell line, FIG. 6). Two of the five computationally identified arginine genes (argininosuccinate lyase, ARGSL and argininosuccinate synthase, ARGSS), one of the thirteen identified cysteine genes (cystathionine b-synthase, CYSTS), and one of two proline genes (pyrroline-5-carboxylate synthetase, P5CS) were previously identified to be involved in naturally occurring CHO auxotrophs (5, 65 Kao and Puck, *Proc. Natl. Acad. Sci. U.S.A.* 60:1275-1281 (1968); Naylor et al., *Somatic. Cell Genet.* 5:271-277 (1979); Kao and Puck, *Genetics* 55:513-524 (1968)). Of multiple reaction functions in the proline biosynthesis pathway, the model correctly identified P5CS gene to be a potential selectable marker. Furthermore, there is currently no evidence in the published literature to suggest that CHO cells are auxotrophic for tyrosine, or to implicate the target phenylalanine 4-monooxygenase (PHE4MO) gene in auxotrophy of the CHO cell lines, thus representing a new target selectable marker. For further validation, continuous colorimetric enzymatic assays were performed with and without the substrate to test the function of P5CS, PHE4MO, and ARGSL enzymes, and no activity was detected in either of the cell lines. The proline and tyrosine targets were selected for further characterization.

Selectable Marker Validation. CHO-K1 and CHO-S cell lines were transfected with pCI vector (Promega, Madison Wis.) containing the murine P5CS gene and a monomeric RFP (red fluorescent protein) gene using Free-style Max transfection reagent (Invitrogen). RFP was included in the construct to facilitate screening of transfection events and determination of transfection efficiency on a Guava PCA instrument (Millipore, Billerica Mass.), and as a surrogate for a protein product. Forty eight hours post-transfection, the cell lines were subjected to two weeks of selection in media without proline, and stably transfected CHO cell lines expressing P5CS were generated and characterized. A similar construct containing the murine PHEO4MO gene (tyrosine target) was also transfected into these cell lines and is currently under selection. The PHEO4MO cell line is similarly characterized as described for the P5CS line.

TABLE 2

Sources of Genes for Constructs.

| Pathway | Gene Target | Gene Alias | Gene Description | Accession Number |
|---------|-------------|------------|------------------|------------------|
| Proline | mALDH18a1 | mPC5S | *Mus musculus* aldehyde dehydrogenase 18 family, member A1 (Aldh18a1) | NM_019698.2 (GI: 255958291) |
| Arginine | mASL | | *Mus musculus* argininosuccinate lyase (Asl) | NM_133768.3 (GI: 142353065) |
| Arginine | mASS1 | | *Mus musculus* argininosuccinate synthetase 1 (Ass1) | NM_007494.3 (GI: 133893196) |
| Tyrosine | mPAH | mPHE4MO | *Mus musculus* phenylalanine hydroxylase (Pah) | NM_008777.3 (GI: 171543885) |

Figure 7A:
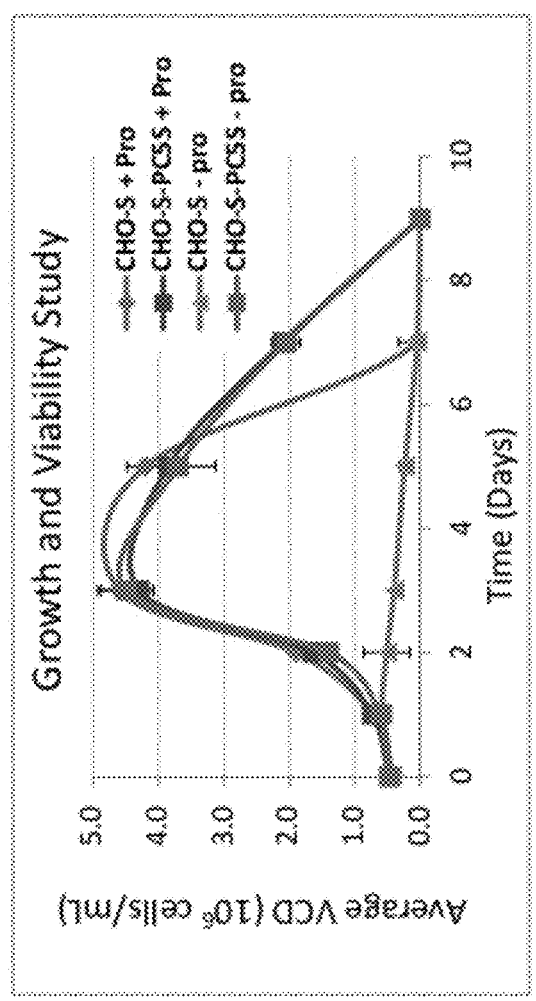
FIGS. 7A-7E show validation results for a pyrroline-5-carboxylate synthetase (P5CS) selection system. Viable cell density was monitored over time in untransfected and transfected CHO-S cells (FIG. 7A). HPLC analysis shows an increase in media concentration of proline over time in transfected CHO-S cells, only (FIG. 7B). HPLC analysis shows lower lactate and ammonium peak concentrations in transfected versus untransfected cells (FIG. 7C). PC5S (2 Kb amplicon) RT-PCR results for CHO-K1 and CHO-S cells, showing expression in transfected cells (FIG. 7D). Enzymatic assay showing a greater rate of PC5S activity (measured as a decrease in absorption over time) seen in crude lysates from transfected CHO-S cells over untransfected cells (crude lysate from *E. coli* cells was used as a positive control) (FIG. 7E).
Figure 7B:
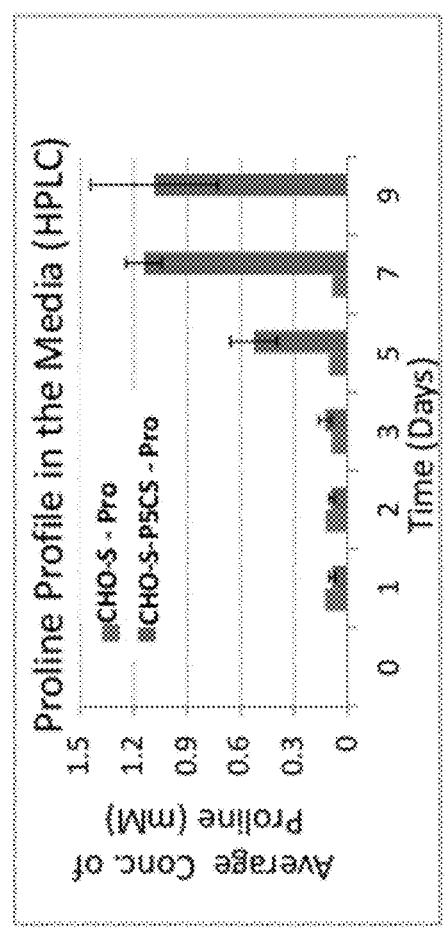
Figure 7C:
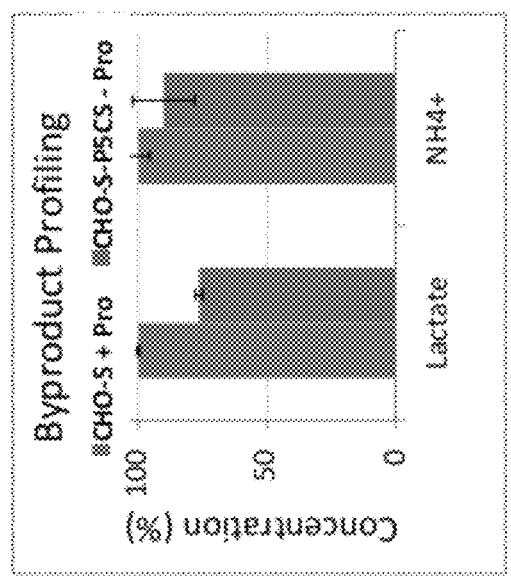
Figure 7D:
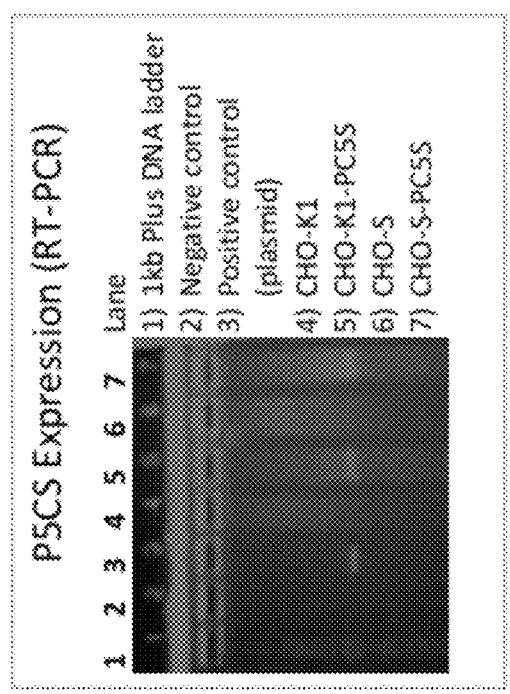

Growth and viability were assessed in parental untransfected cells and cells stably expressing P5CS by seeding at $0.5 \times 10^6$ cells/mL in media with and without proline in duplicate shake flasks. The flasks were sampled for viable cell density and percent viability once every other day, for ten days or until viability dropped below 5%. The results show that only those cells that have proline in the media, or cells that express P5CS in media without proline, can grow (FIG. 7A). The result also shows that growth of the cells expressing P5CS is not affected by proline presence in the media. These cells grown in media without proline were further characterized by metabolic profiling through HPLC analysis and using NOVA Bioprofile 400. It was found that only those cells that express P5CS show a steady production of proline throughout the batch culture (FIG. 7B), especially when cells stop growing in stationary phase (i.e. day 3). Byproducts lactate and ammonium that negatively affect cell growth, productivity and product quality were found in lower peak concentrations in P5CS transfected versus untransfected cell batch cultures (FIG. 7C). Thus, surprisingly cells expressing P5CS demonstrated unexpected properties of extended growth (FIG. 7A) and lower byproduct production (FIG. 7C).

To ensure that the proline target, P5CS, was stably expressed and to validate gene expression, RT-PCR was performed. Briefly, total RNA was extracted from each cell line, including parental untransfected cells, as negative controls. The RNA was converted to cDNA using reverse transcriptase and was used as template in a PCR amplification reaction with primers specific for murine P5CS detection (see Table 3 for PCR primers).

TABLE 3

Primers for PCR Amplification.

| Pathway | Gene Target | 5' PCR Primer | 3' PCR Primer | Cell Line |
|---|---|---|---|---|
| Proline | mALDH18a1 | AGCTGAAGCACGCCA AGAGAATTG (SEQ ID NO: 1) | ATTCCAACTTCAGCT CCCAGTCCA (SEQ ID NO: 2) | C0200, C0300 |
| Proline | mALDH18a1 | ATGCTGAGACACAT GCACCGC (SEQ ID NO: 3) | TCAGCTGAAATTTCTCT GGGGAAC (SEQ ID NO: 4) | C0200, C0101 |

Cell lines: C0200, CHO PROTEIN FREE (ECACC Catalogue No. 00102307), C0300, CHO-S (Invitrogen, Cat. No. 11619-012), and C0101 (an IgG expressing cell line).

Figure 7E:
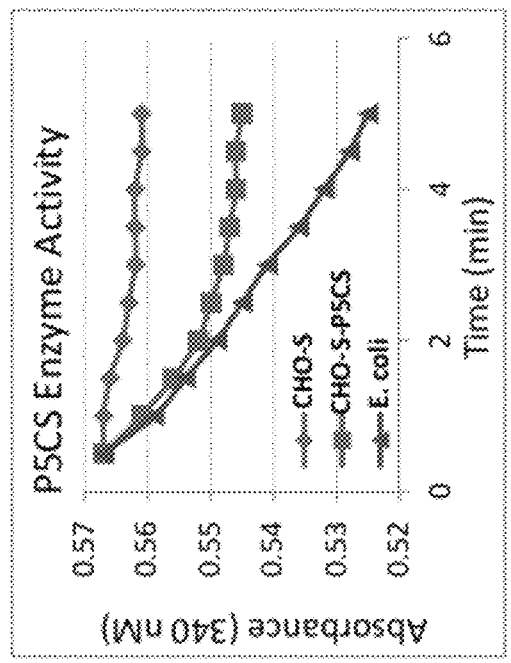

The original plasmid used for the transfections served as the positive control. Amplicons of the appropriate size (1.8 kb) were detected on an agarose gel, purified, and sequence-verified (Genewiz, Inc.) (FIG. 7). Murine P5CS protein function was also tested in untransfected and transfected CHO-S cells using an enzymatic assay. First, the mitochondria from the cells were isolated using a mitochondrial isolation kit (Pierce). The mitochondrial pellets were lysed using lysis buffer and the crude protein was quantified using a Bradford assay. The P5CS assay, which is the ATP- and NADPH-dependent reduction of glumate to glutamate 5-semialdehyde, was performed in a reaction containing the crude protein, Tris-HCl, $MgCl_2$, ATP, and NADPH (Garcia-Rios et al., Proc. Natl. Acad. Sci. U.S.A. 94:8249-8254 (1997)). The substrate sodium glutamate was either added or not added (blank), and the decrease in absorbance at 340 nm was measured over time as the rate of NADPH consumption. Because purified P5CS enzyme was commercially unavailable, a crude lysate from E. coli cells endogenously expressing P5CS was used as a positive control. The results show a greater rate of P5CS enzymatic activity in transfected CHO-S cells over non-transfected cells (FIG. 7E).

Finally, as a preliminary expression stability study, FACS analysis and western blotting were performed to monitor RFP protein expression and stability for 5 weeks. Fluorescent protein expression was analyzed on a BD FACScan analyzer (BD Biosciences) using an argon-ion laser excitation at 488 nm (Cytometry Research, LLC). Data acquisition was carried out by analyzing 10,000 events/sample. A noticeable shift was seen in the transfected CHO-K1 cells, indicating RFP expression. In addition, protein expression was analyzed by SDS-page and western blotting. The results were consistent with the FACS analysis.

These results show that the target selectable markers identified can function in a selectable marker system and can function to express a protein product, exemplified here as RFP.

EXAMPLE III

Developing Biotherapeutic-Producing CHO Cell Lines Using Model-Based Selectable Markers This example describes producing a desired product using a selectable marker identified by the model-based methods.

Figure 8:
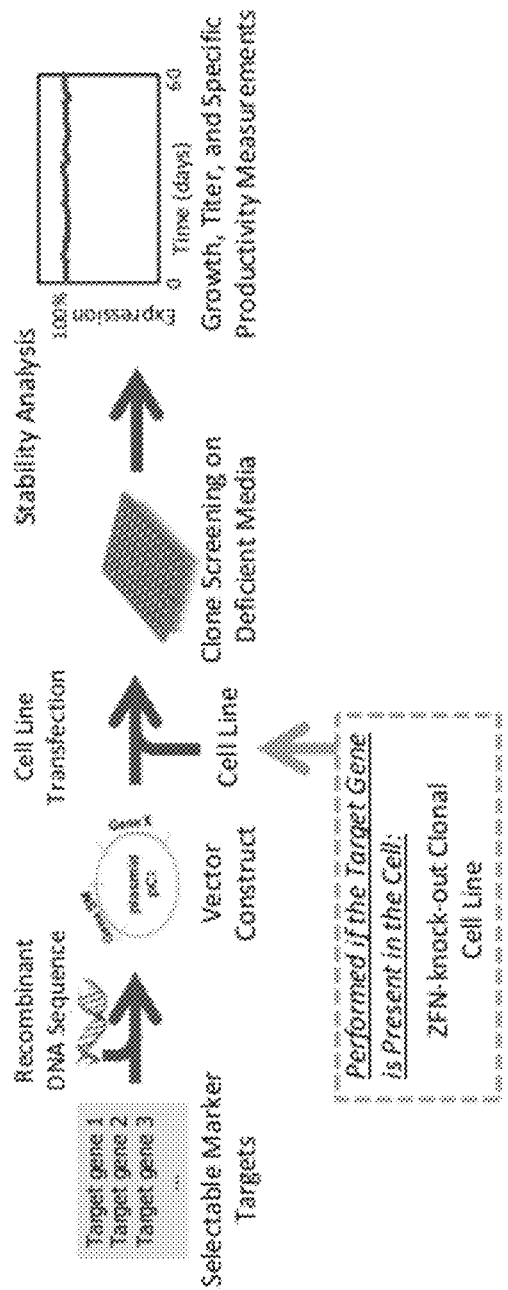
FIG. 8 shows a diagram of using a model-derived selectable marker to express a recombinant protein, select producing cells, and establish expression stability by measuring growth, product titer, and specific productivity over time.

The selectable markers identified by the model, such as P5CS, can be used to select cell lines expressing a recombinant product. If the target gene is present in the genome of a desired cell line, a knock-out cell line is developed first. For this purpose, the presence of the gene in the host cell line is verified using, for example, the genomic sequence, whole transcriptome data, RT-PCR, and/or Western blotting to determine the presence or absence of gene expression or enzymatic function of the gene product in the cell line. If present, the targeted gene is disrupted, either fully or partially knocked out or mutated using various tools, including Zinc Finger Nuclease (ZFN) technology (Santiago et al., Proc. Natl. Acad. Sci. U.S.A. 105:5809-5814 (2008)). Design and synthesis of the Zinc Finger Nucleases, as an example, can be obtained commercially (Sigma-Aldrich, Corp.). Sigma-Aldrich provides the synthesized and validated ZFNs and all the necessary reagents for cell line transfection and knock-out validation. Cell transfection, clone selection, and PCR assays are performed in the host cell line. Clonal ZFN-CHO cell lines can be isolated in this manner, banked, and used for further cell line development (FIG. 8).

The selectable marker genes can be inserted into a vector backbone, such as a pCI vector backbone (Promega), that contains promoter and enhancer elements, such as a CMV promoter and a synthetic intron, to maximize expression of a recombinant product. To introduce the plasmids into the host cells, the vector can be inserted into the cells using, for example, cationic-lipid-based transfections with Free-style Max (Invitrogen) for 48 hours in CHO-S or CHO-K1 cell lines, with a few different transfection conditions performed in parallel. Other well known transfection methods can also be used. Transfected populations can be generated by auxotrophy selection for, e.g., 2 weeks. To rapidly identify the highest producing clones, cell lines are screened using manual or automated approaches, such as limited dilution or Cell Xpress™ technology (Cyntellect, Inc., San Diego Calif.) (Hanania et al., Biotechnol. Bioeng. 91(7), 872-876 (2005).). For example using the Cell Xpress™ technology, the cells are seeded into 384-well tissue culture plates (with 150-200 cells/well), in the presence of a matrix designed to capture secreted product, e.g. IgG molecules. After overnight incubation, captured product can be detected via a secondary reagent containing a conjugated fluorophore, and the viable cells are stained with live cell tracking dye. Following a short incubation, the captured product secretions and associated live cells are visualized and the highest producing cells are retained while the undesired cells are removed from the population by laser-induced apoptosis. The plates are then incubated and the product titers are measured using, for example, Enzyme-linked immunosorbent assay (ELISA) or other suitable assays. The top highest producing wells (e.g. the top 30, 40, or 50) are scaled up, e.g. in 24-well plates. The top 10, 15, or 20 producing wells are then be scaled up, e.g. in 6-well plates, and finally in shake flasks for further stability testing. Expression stability of the recombinant product can be tested in continuously passaged cell cultures for the top producing clones by, e.g. RT-PCR, Western Blot, and/or ELISA, over time, e.g. twice a week for at least 5 weeks.

This example describes generating cells genetically engineered to disrupt expression of a protein suitable as a selection marker, such as those described in Table 1.

EXAMPLE IV

Phenylalanine 4-Monooxygenase as a Selectable Marker

This example describes phenylalanine 4-monooxygenase as a selectable marker.

Figure 9:
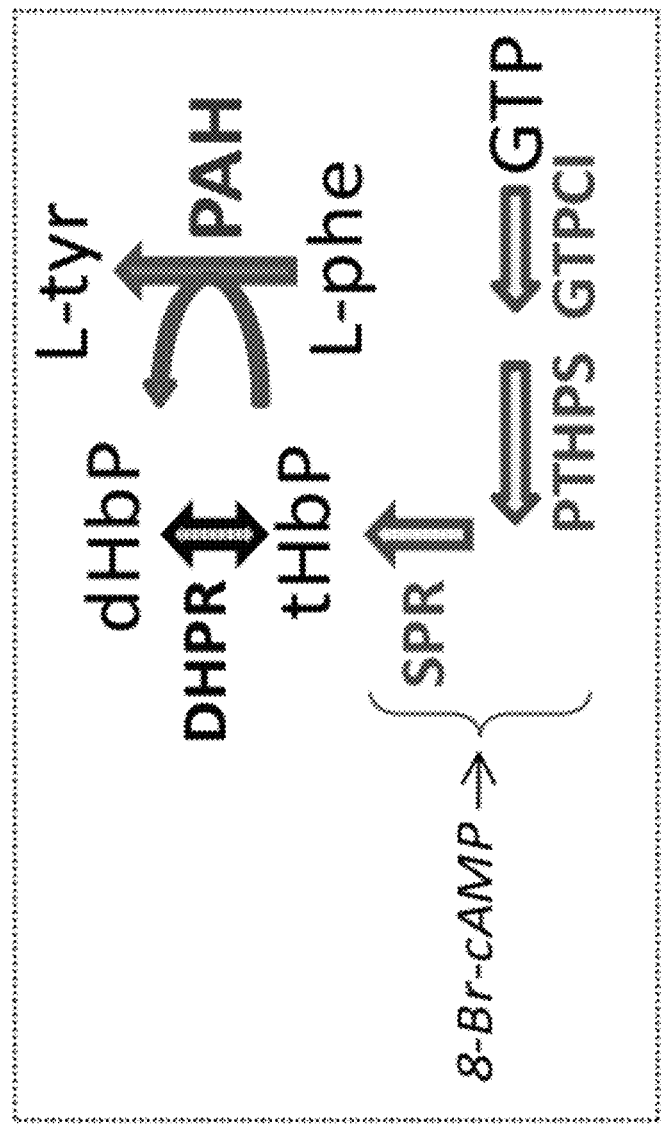
FIG. 9 shows tyrosine biosynthesis in mammalian cells. Tyrosine is synthesized from phenylalanine and tetrahydrobiopterine (tHbP) through the activity of phenylalanine 4-Monooxygenase (PAH). tHbP is synthesized in three steps from GTP. Enzymatic activities of the reactions in tHbP biosynthesis have shown to be induced by 8-Br-cAMP supplementation 1. Abbreviations are 8-Br-cAMP, 8-bromo-cyclic AMP; DHPR, dihydropteridine reductase; SPR, sepiapterin reductase; PTHPS, 6-pyruvoyltetrahydropterin synthase; GTPCI, GTP cyclohydrolase I.

Tyrosine is synthesized from phenylalanine and tetrahydrobiopterine (tHbP) through the activity of phenylalanine 4-monooxygenase (PAH) in mammalian cells. Enzymatic activities of the reactions involved in tHbP synthesis have shown to be induced by 8-Br-cAMP supplementation (Zhu et al., *J. Biol. Chem.* 269:11825-11829 (1994)) (see FIG. 9). In mouse, rat, and human, a single gene has been identified to encode the PAH protein (NCBI GeneID: 18478 (mouse), 24616 (rat), and 5053 (human)). Absence or inactivity of PAH enzyme in CHO cells, however, has not been documented in the past and its potential application as a selectable marker has not been described previously. PAH is therefore particularly useful as a selectable marker.

To experimentally evaluate phenylalanine 4-monooxygenase (PAH) as a selectable marker, Free-style CHO-S cells (Invitrogen; Carlsbad Calif.) were transfected with a pCI vector containing the murine PAH gene and RFP using Freestyle Max transfection reagent. For this experiment, Freestyle CHO-S cells were used since the transfection efficiency in this cell line was determined to be higher compared with the CHO-S cell line. 48 hours post-transfection, the cell lines were subjected to one week of selection in CD OptiCHO™ medium (Invitrogen) lacking tyrosine with and without supplementation of 8-Br-cAMP to generate stably transfected CHO cells. Growth and viability were assessed in parental untransfected cells and cells stably expressing PAH by seeding at $0.2 \times 10^6$ cells/mL in media with and without tyrosine and in the presence and absence of 8-Br-cAMP in duplicate 24-well plates. The plates were sampled for viable cell density and percent viability once every day, for five days. The results show that PAH expressing cells can grow in media without tyrosine, but require supplementation of 8-Br-cAMP, as shown in FIG. 10A. Further optimization of 8-Br-cAMP concentration can be utilized to determine optimum cell growth in the transfected cultures. Alternatively, to avoid supplementation of 8-Br-cAMP, pathway engineering approaches can be implemented to boost the endogenous production of tHbP.

The PAH-transfected cells were further characterized by growing in media without tyrosine by metabolic profiling through HPLC analysis and using enzymatic assays for lactate (Lactate Assay Kit, Biovision Research Products; Mountain View Calif.) and ammonium (Ammonia Assay Kit, Biovision Research Products). It was found that cells expressing PAH showed production of tyrosine in batch culture, confirming PAH gene expression (FIG. 10B). Lactate and ammonium accumulation were found to be significantly lower in PAH transfected versus untransfected cell batch cultures (FIG. 10C). PAH function was also tested in an assay measuring conversion of L-phenylalanine to L-tyrosine in the presence of 6-methyltetrahydropterine (6-MTHP) (Sigma Aldrich). Briefly, crude cell lysates were obtained from untransfected cells, PAH transfected cells, and jurkat cells known to express PAH (positive control) using lysis buffer. A Bradford assay was performed to determine total protein and, following normalization, protein lysates were incubated in a reaction mix containing, Tris, L-phenylalanine, dithiothreitol (DTT), catalase, and (6-MTHP) at 55° C. for 30 min. The assay mix was cooled to 25° C., centrifuged, and the cleared solutions were read for absorbance at 450 nM. Tyrosine production was measured against a serial dilution of tyrosine standard. The results indicate PAH enzyme activity from lysates isolated from the CHO-S cells stably transfected with PAH is comparable to the positive control, and no tyrosine production was seen in lysates from parental cells (FIG. 10D).

In addition to the usefulness of PAH as a selectable marker in mammalian cell culture as described above, tyrosine is known to be highly insoluble in cell culture media and can be toxic at high concentrations. Engineering CHO cells that express an active form of PAH can eliminate the need for supplying tyrosine in the media, reducing the effort and the cost of media design and development in animal cell culture.

Figures 11A, 11B:
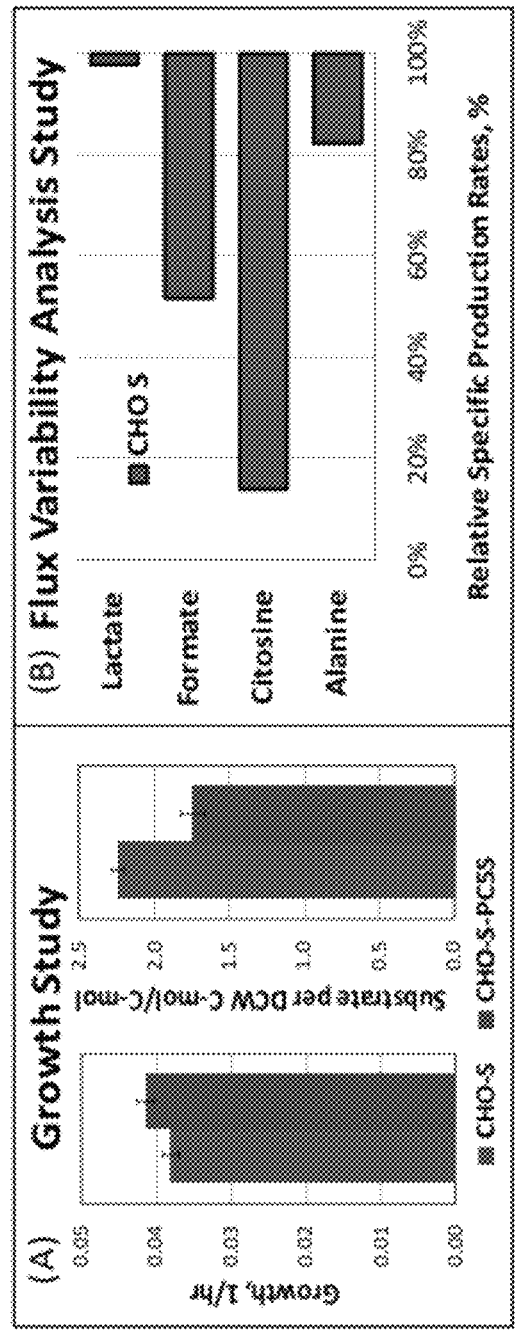
FIGS. 11A-11B shows computational analysis of CHO-S-P5CS cell line.

Additional analysis of the metabolic benefits induced by selection marker PC5S was performed. Amino and organic acid HPLC and growth data analysis for the CHO-S and CHO-S-PC5S strains showed 8% increase in maximum specific growth rate of the transfected cells, indicating that transfected cells benefited from expressing PC5S, instead of consuming proline from the medium (FIG. 11A). Transfected cells required 27% less C-mols to produce one C-mol of biomass compared with the non-transfected CHO-S. The data shows that transfected cells are more metabolically efficient than the parental CHO-S, indicating that more of the carbon flux can be directed towards recombinant protein production (FIG. 11A) (Stephanopoulos et al., *Metabolic Engineering: Principles and Methodologies*, Academic Press, San Diego, Calif. (1998)). Flux variability analysis performed using SimPheny™ (see U.S. publication 2003/0233218 and U.S. Pat. No. 7,856,317) showed that CHO-S-PC5S cells do not have to produce formate, cytosine, lactate and alanine, however to reach a mass balance, the parental CHO-S cells must produce these byproducts (FIG. 11B). These data indicate that, through media optimization or cell engineering approaches, byproduct formation can be reduced in P5CS-transfected CHO cells and flux redirected towards protein production more efficiently.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

TABLE 4

Reactions and Metabolites in CHO Model

| Rxn Abbreviation | Equation | EC Number |
|---|---|---|
| 2OXOADPTm | 2oxoadp[c] + akg[m] <==> 2oxoadp[m] + akg[c] | |
| 3DSPHR | [c]: 3dsphgn + h + nadph --> nadp + sphgn | 1.1.1.102 |
| 3SALAASPm | 3sala[m] + asp-L[c] <==> 3sala[c] + asp-L[m] | |
| 4ABUTtm | 4abut[c] <==> 4abut[m] | |
| 5AOPtm | 5aop[c] <==> 5aop[m] | |
| 6PGCter | 6pgc[c] <==> 6pgc[r] | |
| AASAD3m | [m]: ampsal + h2o + nad --> 2aadp + (2) h + nadh | 1.2.1.31 |
| ABTArm | [m]: 4abut + akg <==> glu-L + sucsal | 2.6.1.19 |
| ABUTD | [c]: 4abutn + h2o + nad --> 4abut + (2) h + nadh | 1.2.1.19 |
| ACACT10rm | [m]: 2maacoa + coa <==> accoa + ppcoa | 2.3.1.16 |
| ACACT1r | [c]: (2) accoa <==> aacoa + coa | 2.3.1.9 |
| ACACT1rm | [m]: (2) accoa <==> aacoa + coa | 2.3.1.9 |
| ACACt2m | acac[c] + h[c] <==> acac[m] + h[m] | |
| ACAT_CHO | [c]: chsterol + (0.001) facoa_avg_CHO --> (0.001) cholse_CHO + coa | 2.3.1.26 |
| ACCOAC | [c]: accoa + atp + hco3 --> adp + h + malcoa + pi | 6.4.1.2 |
| ACGK_CHO | [c]: atp + (0.001) mglyc_CHO --> (0.001) 1ag3p_CHO + adp + h | |
| ACMUCD | [c]: acmucsal + h --> amucsal + co2 | 4.1.1.45 |
| ACOAD1m | [m]: fad + ivcoa <==> 3mb2coa + fadh2 | 1.3.99.3 |
| ACOAD2m | [m]: fad + ibcoa <==> 2mp2coa + fadh2 | 1.3.99.3 |
| ACOAD3m | [m]: 2mbcoa + fad <==> 2mb2coa + fadh2 | 1.3.99.3 |
| ACONT | [c]: cit <==> icit | 4.2.1.3 |
| ACONTm | [m]: cit <==> icit | 4.2.1.3 |
| ADK1 | [c]: amp + atp <==> (2) adp | 2.7.4.3 |
| ADK1m | [m]: amp + atp <==> (2) adp | 2.7.4.3 |
| ADMDCi | [c]: amet + h --> ametam + co2 | 4.1.1.50 |
| ADNK1 | [c]: adn + atp --> adp + amp + h | 2.7.1.20 |
| ADSL1r | [c]: dcamp <==> amp + fum | 4.3.2.2 |
| ADSL2r | [c]: 25aics <==> aicar + fum | 4.3.2.2 |
| ADSS | [c]: asp-L + gtp + imp --> dcamp + gdp + (2) h + pi | 6.3.4.4 |
| AGAT_CHO | [c]: (0.001) 1ag3p_CHO + (0.025) arachdcoa + (0.016) clpndcoa + (0.01) cvncoa + (0.002) ecsacoa + (0.003) ecspecoa + (0.004) estcoa + (0.064) hdcoa + (0.007) lgncoa + (0.003) lnlecoa + (0.008) nrvnccoa + (0.042) ocdycacoa + (0.404) odecoa + (0.253) pmtcoa + (0.13) strcoa + (0.029) tdcoa --> coa + (0.001) pa_CHO | 2.3.1.51 |
| AGMTm | [m]: agm + h2o --> ptrc + urea | 3.5.3.11 |
| AHC | [c]: ahcys + h2o <==> adn + hcys-L | 3.3.1.1 |
| AICART | [c]: 10fthf + aicar <==> fprica + thf | 2.1.2.3 |
| AIRCr | [c]: air + co2 <==> 5aizc + h | 4.1.1.21 |
| AKBDHm | [m]: 2obut + coa + nad --> co2 + nadh + ppcoa | |
| AKBtm | 2obut[m] <==> 2obut[c] | |
| AKGD2m | [m]: 2oxoadp + coa + nad --> co2 + glutcoa + nadh | |
| AKGDm | [m]: akg + coa + nad --> co2 + nadh + succoa | |
| ALA_Lt6 | ala-L[e] + h[e] <==> ala-L[c] + h[c] | |
| ALASm | [m]: gly + h + succoa --> 5aop + co2 + coa | 2.3.1.37 |
| ALATA_L | [c]: akg + ala-L <==> glu-L + pyr | 2.6.1.2 |
| ALDD4xm | [m]: h2o + mmalsa-S + nad --> (2) h + mmal + nadh | 1.2.1.3 |
| ALDOX1 | [c]: h2o + mmalsa-S + o2 --> h + h2o2 + mmal | 1.2.3.1 |
| AMCOXO | [c]: 2amuc + h + h2o + nadph --> 2oxoadp + nadp + nh4 | |
| AMIOX6 | [c]: h2o + o2 + ptrc --> 4abutn + h2o2 + nh4 | 1.4.3.6 |
| AMUCD | [c]: amucsal + h2o + nad --> 2amuc + (2) h + nadh | 1.2.1.32 |
| ARACHDAtr | arachda[e] <==> arachda[c] | |
| ARACHt | ecsa[e] <==> ecsa[c] | |
| ARGDCm | [m]: arg-L + h --> agm + co2 | 4.1.1.19 |
| ARGSL | [c]: argsuc <==> arg-L + fum | 4.3.2.1 |
| ARGSS | [c]: asp-L + atp + citr-L --> amp + argsuc + h + ppi | 6.3.4.5 |
| ARGt3m | arg-L[c] + h[m] <==> arg-L[m] + h[c] | |
| ARGtr | arg-L[e] <==> arg-L[c] | |
| ASNN | [c]: asn-L + h2o --> asp-L + nh4 | 3.5.1.1 |
| ASNS1 | [c]: asp-L + atp + gln-L + h2o --> amp + asn-L + glu-L + h + ppi | 6.3.5.4 |
| ASNt4r | asn-L[e] + na1[e] <==> asn-L[c] + na1[c] | |
| ASPCTr | [c]: asp-L + cbp <==> cbasp + h + pi | 2.1.3.2 |
| ASPt4 | asp-L[c] + na1[c] <==> asp-L[e] + na1[e] | |
| ASPTA1 | [c]: akg + asp-L <==> glu-L + oaa | 2.6.1.1 |
| ASPTA1m | [m]: akg + asp-L <==> glu-L + oaa | 2.6.1.1 |
| ASPTA3 | [c]: 3sala + akg --> glu-L + spyr | 2.6.1.1 |
| ASPTA4 | [c]: akg + cys-L <==> glu-L + mercppyr | 2.6.1.1 |
| ATP/ADPtm | adp[c] + atp[m] <==> adp[m] + atp[c] | |
| ATP/ADPtp | adp[c] + atp[x] <==> adp[x] + atp[c] | |
| ATPM | [c]: atp + h2o --> adp + h + pi | 3.6.1.15 |
| ATPS | atp[c] + h2o[c] --> adp[c] + h[e] + pi[c] | 3.6.3.6 |

TABLE 4-continued

Reactions and Metabolites in CHO Model

| | | |
|---|---|---|
| ATPS4m | adp[m] + (4) h[c] + pi[m] --> atp[m] + (3) h[m] + h2o[m] | 3.6.3.14 |
| C14STRer | [r]: 44mctr + h + nadph --> 44mzym + nadp | 1.3.1.70 |
| C3STDH1xer | [r]: 4mzym_int1 + nad --> 4mzym_int2 + co2 + nadh | 1.1.1.170 |
| C3STDH1yer | [r]: 4mzym_int1 + nadp --> 4mzym_int2 + co2 + nadph | 1.1.1.170 |
| C3STKR2er | [r]: h + nadph + zym_int2 --> nadp + zymst | 1.1.1.270 |
| C4STMO1er | [r]: 44mzym + (2) h + (3) nadph + (3) o2 --> 4mzym_int1 + (4) h2o + (3) nadp | 1.14.13.72 |
| C4STMO2xer | [r]: 4mzym_int2 + nad + o2 --> co2 + h + nadh + zym_int2 | 1.14.13.72 |
| C4STMO2yer | [r]: 4mzym_int2 + nadp + o2 --> co2 + h + nadph + zym_int2 | 1.14.13.72 |
| CAT | [c]: (2) h2o2 --> (2) h2o + o2 | 1.11.1.6 |
| CATm | [m]: (2) h2o2 --> (2) h2o + o2 | 1.11.1.6 |
| CATp | [x]: (2) h2o2 --> (2) h2o + o2 | 1.11.1.6 |
| CBPS | [c]: (2) atp + gln-L + h2o + hco3 --> (2) adp + cbp + glu-L + (2) h + pi | 6.3.5.5 |
| CBPSAm | [m]: (2) atp + co2 + h2o + nh4 --> (2) adp + cbp + (3) h + pi | 6.3.4.16 |
| CDO | [c]: cys-L + o2 --> 3sala | 1.13.11.20 |
| CDPDGPm_CHO | [m]: (0.001) cdpdag_CHO + glyc3p <==> cmp + h + (0.001) pgp_CHO | 2.7.8.8 |
| CERPT2_CHO | [c]: (0.001) cer_CHO + h + (0.001) pc_CHO --> (0.001) 12dgr_CHO + (0.001) sphgmy_CHO | 2.7.8.27 |
| CERS_CHO | [c]: (0.001) facoa_avg_CHO + sphgn --> coa + (0.001) dcer_CHO + h | 2.3.1.24 |
| CHLPCTD | [c]: cholp + ctp + h --> cdpchol + ppi | 2.7.7.15 |
| CHOLK | [c]: atp + chol --> adp + cholp + h | 2.7.1.32 |
| CHOLSE_CHO | [c]: (0.025) arachda + chsterol + (0.01) dcshea + (0.016) dcspea + (0.002) ecsa + (0.003) ecspea + (0.004) ecstea + h + (0.253) hdca + (0.064) hdcea + (0.003) lnlne + (0.008) nrvnc + (0.13) ocdca + (0.404) ocdcea + (0.042) ocdcya + (0.007) ttc + (0.029) ttdca <==> (0.001) cholse_CHO + h2o | 6.2.1.3 |
| CHOLtu | chol[e] <==> chol[c] | |
| CHSTEROLter | chsterol[c] <==> chsterol[r] | |
| CHSTNIer | [r]: zymst <==> cholsd | 5.3.3.5 |
| CITL2 | [c]: atp + cit + coa --> accoa + adp + oaa + pi | 4.1.3.8 |
| CITMALtm | cit[c] + h[c] + mal-L[m] <==> cit[m] + h[m] + mal-L[c] | |
| CLPNtm_CHO | clpn_CHO[m] <==> clpn_CHO[c] | |
| CLSm_CHO | [m]: (0.001) cdpdag_CHO + (0.001) pg_CHO --> (0.001) clpn_CHO + cmp + h | |
| CO2t | co2[e] <==> co2[c] | |
| CO2ter | co2[c] <==> co2[r] | |
| CO2tm | co2[c] <==> co2[m] | |
| CO2tp | co2[c] <==> co2[x] | |
| CPPPGO | [c]: cpppg3 + (2) h + o2 --> (2) co2 + (2) h2o + pppg9 | 1.3.3.3 |
| CRNAR | [c]: arachdcoa + crn <==> arachdcrn + coa | 2.3.1.21 |
| CRNARm | [m]: arachdcoa + crn <==> arachdcrn + coa | 2.3.1.21 |
| CRNARtm | arachdcrn[c] + crn[m] <==> arachdcrn[m] + crn[c] | |
| CRNDSH | [c]: crn + cvncoa <==> coa + cvncrn | 2.3.1.21 |
| CRNDSHm | [m]: crn + cvncoa <==> coa + cvncrn | 2.3.1.21 |
| CRNDSHtm | crn[m] + cvncrn[c] <==> crn[c] + cvncrn[m] | |
| CRNDSP | [c]: clpndcoa + crn <==> clpndcrn + coa | 2.3.1.21 |
| CRNDSPm | [m]: clpndcoa + crn <==> clpndcrn + coa | 2.3.1.21 |
| CRNDSPtm | clpndcrn[c] + crn[m] <==> clpndcrn[m] + crn[c] | |
| CRNESP | [c]: crn + ecspecoa <==> coa + ecspecrn | 2.3.1.21 |
| CRNESPm | [m]: crn + ecspecoa <==> coa + ecspecrn | 2.3.1.21 |
| CRNESPtm | crn[m] + ecspecrn[c] <==> crn[c] + ecspecrn[m] | |
| CRNEST | [c]: crn + estcoa <==> coa + estcrn | 2.3.1.21 |
| CRNESTm | [m]: crn + estcoa <==> coa + estcrn | 2.3.1.21 |
| CRNESTtm | crn[m] + estcrn[c] <==> crn[c] + estcrn[m] | |
| CRNET | [c]: crn + ecsacoa <==> coa + ecsacrn | 2.3.1.21 |
| CRNETm | [m]: coa + ecsacrn <==> crn + ecsacoa | 2.3.1.21 |
| CRNETtm | crn[m] + ecsacrn[c] <==> crn[c] + ecsacrn[m] | |
| CRNHD | [c]: crn + hdcoa <==> coa + hdcecrn | 2.3.1.21 |
| CRNHDm | [m]: crn + hdcoa <==> coa + hdcecrn | 2.3.1.21 |
| CRNHDtm | crn[m] + hdcecrn[c] <==> crn[c] + hdcecrn[m] | |
| CRNLN | [c]: crn + lnlecoa <==> coa + lnlecrn | 2.3.1.21 |
| CRNLNm | [m]: crn + lnlecoa <==> coa + lnlecrn | 2.3.1.21 |
| CRNLNtm | crn[m] + lnlecrn[c] <==> crn[c] + lnlecrn[m] | |
| CRNNR | [c]: crn + nrvnccoa <==> coa + nrvnccrn | 2.3.1.21 |
| CRNNRm | [m]: crn + nrvnccoa <==> coa + nrvnccrn | 2.3.1.21 |
| CRNNRtm | crn[m] + nrvnccrn[c] <==> crn[c] + nrvnccrn[m] | |

TABLE 4-continued

Reactions and Metabolites in CHO Model

| | | |
|---|---|---|
| CRNOC | [c]: crn + ocdycacoa <==> coa + ocdycacrn | 2.3.1.21 |
| CRNOCm | [m]: crn + ocdycacoa <==> coa + ocdycacrn | 2.3.1.21 |
| CRNOCtm | crn[m] + ocdycacrn[c] <==> crn[c] + ocdycacrn[m] | |
| CRNOD | [c]: crn + odecoa <==> coa + odecrn | 2.3.1.21 |
| CRNODm | [m]: crn + odecoa <==> coa + odecrn | 2.3.1.21 |
| CRNODtm | crn[m] + odecrn[c] <==> crn[c] + odecrn[m] | |
| CRNOT | [c]: crn + strcoa <==> coa + strcrn | 2.3.1.21 |
| CRNOTm | [m]: coa + strcrn <==> crn + strcoa | 2.3.1.21 |
| CRNOTtm | crn[m] + strcrn[c] <==> crn[c] + strcrn[m] | |
| CRNPT | [c]: crn + pmtcoa <==> coa + pmtcrn | 2.3.1.21 |
| CRNPTm | [m]: coa + pmtcrn <==> crn + pmtcoa | 2.3.1.21 |
| CRNPTtm | crn[m] + pmtcrn[c] <==> crn[c] + pmtcrn[m] | |
| CRNTC | [c]: crn + lgnccoa <==> coa + lgnccrn | 2.3.1.21 |
| CRNTCm | [m]: crn + lgnccoa <==> coa + lgnccrn | 2.3.1.21 |
| CRNTCtm | crn[m] + lgnccrn[c] <==> crn[c] + lgnccrn[m] | |
| CRNTDm | [m]: coa + tdcrn <==> crn + tdcoa | 2.3.1.21 |
| CRNTDT | [c]: crn + tdcoa <==> coa + tdcrn | 2.3.1.21 |
| CRNTTtm | crn[m] + tdcrn[c] <==> crn[c] + tdcrn[m] | |
| CSm | [m]: accoa + h2o + oaa --> cit + coa + h | 4.1.3.7 |
| CSNATm | [m]: acrn + coa <==> accoa + crn | 2.3.1.7 |
| CSNATr | [c]: accoa + crn <==> acrn + coa | 2.3.1.7 |
| CSNATtm | acrn[c] + crn[c] <==> acrn[m] + crn[m] | |
| CTPS1 | [c]: atp + nh4 + utp --> adp + ctp + (2) h + pi | 6.3.4.2 |
| CTPS2 | [c]: atp + gln-L + h2o + utp --> adp + ctp + glu-L + (2) h + pi | 6.3.4.2 |
| CYOO4m | (4) focytcc[m] + (8) h[m] + o2[m] --> (4) ficytcc[m] + (4) h[c] + (2) h2o[m] | 1.9.3.1 |
| CYOR4m-ubq10 | (2) ficytcc[m] + (2) h[m] + q10h2[m] --> (2) focytcc[m] + (4) h[c] + ubq10[m] | 1.10.2.2 |
| CYSt4r | cys-L[e] + na1[e] <==> cys-L[c] + na1[c] | |
| CYSTGL | [c]: cysth-L + h2o --> 2obut + cys-L + nh4 | 4.4.1.1 |
| CYSTS | [c]: hcys-L + ser-L --> cysth-L + h2o | 4.2.1.22 |
| CYTK1 | [c]: atp + cmp <==> adp + cdp | 2.7.4.14 |
| CYTK1m | [m]: atp + cmp <==> adp + cdp | 2.7.4.14 |
| DAGCPT_CHO | [c]: (0.001) 12dgr_CHO + cdpchol --> cmp + h + (0.001) pc_CHO | 2.7.8.2 |
| DAGH_CHO | [c]: (0.001) 12dgr_CHO + h2o --> (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.001) mglyc_CHO + (0.008) nrvnc + (0.13) ocdca + (0.404) ocdcea + (0.042) ocdcya + (0.007) ttc + (0.029) ttdca | 6.2.1.3 |
| DAGK_CHO | [c]: (0.001) 12dgr_CHO + atp --> adp + h + (0.001) pa_CHO | 2.7.1.107 |
| DAGPYP_CHO | [c]: h2o + (0.001) pa_CHO --> (0.001) 12dgr_CHO + pi | 3.1.3.4 |
| DASYN_CHO | [c]: ctp + h + (0.001) pa_CHO <==> (0.001) cdpdag_CHO + ppi | 2.7.7.41 |
| DASYNm_CHO | [m]: ctp + h + (0.001) pa_CHO <==> (0.001) cdpdag_CHO + ppi | 2.7.7.41 |
| DCERDS_CHO | [c]: (0.001) dcer_CHO + h + nadph + o2 --> (0.001) cer_CHO + (2) h2o + nadp | |
| DCSHEAtr | dcshea[e] <==> dcshea[c] | |
| DCSPEAtr | dcspea[e] <==> dcspea[c] | |
| DESAT161 | [c]: h + nadph + o2 + pmtcoa --> (2) h2o + hdcoa + nadp | 1.14.19.1 |
| DESAT181 | [c]: h + nadph + o2 + strcoa --> (2) h2o + nadp + odecoa | 1.14.19.1 |
| DESAT183 | [c]: h + nadph + o2 + ocdycacoa --> (2) h2o + lnlecoa + nadp | 1.14.19.1 |
| DESAT184 | [c]: h + lnlecoa + nadph + o2 --> (2) h2o + nadp + strdnccoa | 1.14.19.3 |
| DESAT204 | [c]: estcoa + h + nadph + o2 --> arachdcoa + (2) h2o + nadp | 1.14.19.1 |
| DESAT205g | [c]: arachdcoa + h + nadph + o2 --> ecspecoa + (2) h2o + nadp | 1.14.19.1 |
| DESAT226g | [c]: clpndcoa + h + nadph + o2 --> cvncoa + (2) h2o + nadp | 1.14.19.1 |
| DESAT241 | [c]: h + lgnccoa + nadph + o2 --> (2) h2o + nadp + nrvncoa | 1.14.19.1 |
| DHCR71er | [r]: ddsmsterol + h + nadph --> dsmsterol + nadp | 1.3.1.21 |
| DHCR72er | [r]: 7dhchsterol + h + nadph --> chsterol + nadp | 1.3.1.21 |
| DHFOR2 | [c]: dhf + nadp <==> fol + nadph | 1.5.1.3 |
| DHFOR3 | [c]: fol + h + (2) nadph <==> (2) nadp + thf | 1.5.1.3 |
| DHFR | [c]: dhf + h + nadph <==> nadp + thf | 1.5.1.3 |
| DHORD3m-ubq10 | dhor-S[c] + ubq10[m] <==> orot[c] + q10h2[m] | 1.3.99.11 |
| DHORTS | [c]: dhor-S + h2o <==> cbasp + h | 3.5.2.3 |
| DHPRx | [c]: dhbpt + h + nadh <==> nad + thbpt | 1.5.1.34 |

TABLE 4-continued

Reactions and Metabolites in CHO Model

| | | |
|---|---|---|
| DMATT | [c]: dmpp + ipdp --> grdp + ppi | 2.5.1.1 |
| DMPPtp | dmpp[x] <==> dmpp[c] | |
| DPCOAK | [c]: atp + dpcoa --> adp + coa + h | 2.7.1.24 |
| DPMVDp | [x]: 5dpmev + atp --> adp + co2 + ipdp + pi | 4.1.1.33 |
| DTMPK | [c]: atp + dtmp <==> adp + dtdp | 2.7.4.9 |
| EBP2rer | [r]: zymstnl <==> lathost | 5.3.3.5 |
| ECOAH1am | [m]: 3hbycoa <==> b2coa + h2o | 4.2.1.17 |
| ECOAH2m | [m]: 2mp2coa + h2o <==> hibcoa | 4.2.1.17 |
| ECOAH3m | [m]: 2mb2coa + h2o <==> 3hmbcoa | 4.2.1.17 |
| ECSPEAtr | ecspea[e] <==> ecspea[c] | |
| ECSTEAt | ecstea[e] <==> ecstea[c] | |
| ENO | [c]: 2pg <==> h2o + pep | 4.2.1.11 |
| ETAPCTr | [c]: ctp + ethap + h <==> cdpea + ppi | 2.7.7.14 |
| ETHAMK | [c]: atp + etha --> adp + ethap + h | 2.7.1.82 |
| ETHAPT_CHO | [c]: (0.01) 12dgr_CHO + cdpea <==> cmp + h + (0.01) pe_CHO | 2.7.8.1 |
| ETHAt | etha[e] <==> etha[c] | |
| FACOAavg_CHO | [c]: (0.025) arachda + atp + coa + (0.01) dcshea + (0.016) dcspea + (0.002) ecsa + (0.003) ecspea + (0.004) ecstea + (0.253) hdca + (0.064) hdcea + (0.003) lnlne + (0.008) nrvnc + (0.13) ocdca + (0.404) ocdcea + (0.042) ocdcya + (0.007) ttc + (0.029) ttdca <==> amp + (0.001) facoa_avg_CHO + ppi | 6.2.1.3 |
| FACOAL140 | [c]: atp + coa + ttdca <==> amp + ppi + tdcoa | 6.2.1.3 |
| FACOAL160 | [c]: atp + coa + hdca <==> amp + pmtcoa + ppi | 6.2.1.3 |
| FACOAL161 | [c]: atp + coa + hdcea <==> amp + hdcoa + ppi | 6.2.1.3 |
| FACOAL180 | [c]: atp + coa + ocdca <==> amp + ppi + strcoa | 6.2.1.3 |
| FACOAL181 | [c]: atp + coa + ocdcea <==> amp + odecoa + ppi | 6.2.1.3 |
| FACOAL182 | [c]: atp + coa + ocdcya <==> amp + ocdycacoa + ppi | 6.2.1.3 |
| FACOAL183 | [c]: atp + coa + lnlne <==> amp + lnlecoa + ppi | 6.2.1.3 |
| FACOAL200 | [c]: atp + coa + ecsa <==> amp + ecsacoa + ppi | 6.2.1.3 |
| FACOAL203 | [c]: atp + coa + ecstea <==> amp + estcoa + ppi | 6.2.1.3 |
| FACOAL204 | [c]: arachda + atp + coa <==> amp + arachdcoa + ppi | 6.2.1.3 |
| FACOAL205 | [c]: atp + coa + ecspea <==> amp + ecspecoa + ppi | 6.2.1.3 |
| FACOAL225 | [c]: atp + coa + dcspea <==> amp + clpndcoa + ppi | 6.2.1.3 |
| FACOAL226 | [c]: atp + coa + dcshea <==> amp + cvncoa + ppi | 6.2.1.3 |
| FACOAL240 | [c]: atp + coa + ttc <==> amp + lgnccoa + ppi | 6.2.1.3 |
| FACOAL241 | [c]: atp + coa + nrvnc <==> amp + nrvnccoa + ppi | 6.2.1.3 |
| FAEL203 | [c]: (5) h + lnlecoa + malcoa + (4) nadph + o2 --> co2 + coa + estcoa + (3) h2o + (4) nadp | 2.3.1.86 |
| FAEL204g | [c]: (5) h + malcoa + (4) nadph + o2 + strdnccoa --> arachdcoa + co2 + coa + (3) h2o + (4) nadp | 2.3.1.86 |
| FAEL225 | [c]: ecspecoa + (5) h + malcoa + (4) nadph + o2 --> clpndcoa + co2 + coa + (3) h2o + (4) nadp | 2.3.1.86 |
| FALDtp | fald[c] <==> fald[x] | |
| FAOXC100m | [m]: coa + dccoa + fad + h2o + nad --> accoa + fadh2 + h + nadh + occoa | 1.3.99.3 |
| FAOXC120m | [m]: coa + ddcoa + fad + h2o + nad --> accoa + dccoa + fadh2 + h + nadh | 1.3.99.3 |
| FAOXC140m | [m]: coa + fad + h2o + nad + tdcoa --> accoa + ddcoa + fadh2 + h + nadh | 1.3.99.3 |
| FAOXC160m | [m]: coa + fad + h2o + nad + pmtcoa --> accoa + fadh2 + h + nadh + tdcoa | 1.3.99.3 |
| FAOXC161m | [m]: (7) coa + (6) fad + (7) h2o + hdcoa + (7) nad --> (8) accoa + (6) fadh2 + (7) h + (7) nadh | 1.3.99.3 |
| FAOXC180m | [m]: coa + fad + h2o + nad + strcoa --> accoa + fadh2 + h + nadh + pmtcoa | 1.3.99.3 |
| FAOXC181m | [m]: (8) coa + (7) fad + (8) h2o + (8) nad + odecoa --> (9) accoa + (7) fadh2 + (8) h + (8) nadh | 1.3.99.3 |
| FAOXC182 | [m]: (8) coa + (6) fad + (8) h2o + (8) nad + ocdycacoa --> (9) accoa + (6) fadh2 + (8) h + (8) nadh | 1.3.99.3 |
| FAOXC183m | [m]: (8) coa + (5) fad + (8) h2o + lnlecoa + (8) nad --> (9) accoa + (5) fadh2 + (8) h + (8) nadh | 1.3.99.3 |
| FAOXC200m | [m]: coa + ecsacoa + fad + h2o + nad --> accoa + fadh2 + h + nadh + strcoa | 1.3.99.3 |
| FAOXC203m | [m]: (9) coa + estcoa + (6) fad + (9) h2o + (9) nad --> (10) accoa + (6) fadh2 + (9) h + (9) nadh | 1.3.99.3 |
| FAOXC204 | [m]: arachdcoa + (9) coa + (5) fad + (9) h2o + (9) nad --> (10) accoa + (5) fadh2 + (9) h + (9) nadh | 1.3.99.3 |
| FAOXC205m | [m]: (9) coa + ecspecoa + (4) fad + (9) h2o + (9) nad --> (10) accoa + (4) fadh2 + (9) h + (9) nadh | 1.3.99.3 |
| FAOXC225m | [m]: clpndcoa + (10) coa + (5) fad + (10) h2o + (10) nad --> (11) accoa + (5) fadh2 + (10) h + (10) nadh | 1.3.99.3 |

TABLE 4-continued

Reactions and Metabolites in CHO Model

| | | |
|---|---|---|
| FAOXC226 | [m]: (10) coa + cvncoa + (4) fad + (10) h2o + (10) nad --> (11) accoa + (4) fadh2 + (10) h + (10) nadh | 1.3.99.3 |
| FAOXC240m | [m]: (2) coa + (2) fad + (2) h2o + lgnccoa + (2) nad --> (2) accoa + ecsacoa + (2) fadh2 + (2) h + (2) nadh | 1.3.99.3 |
| FAOXC241m | [m]: (11) coa + (10) fad + (11) h2o + (11) nad + nrvnccoa --> (12) accoa + (10) fadh2 + (11) h + (11) nadh | 1.3.99.3 |
| FAOXC40m | [m]: btcoa + coa + fad + h2o + nad --> (2) accoa + fadh2 + h + nadh | 1.3.99.3 |
| FAOXC60m | [m]: coa + fad + h2o + hxcoa + nad --> accoa + btcoa + fadh2 + h + nadh | 1.3.99.3 |
| FAOXC80m | [m]: coa + fad + h2o + nad + occoa --> accoa + fadh2 + h + hxcoa + nadh | 1.3.99.3 |
| FAS100 | [c]: (3) h + malcoa + (2) nadph + octa --> co2 + coa + dca + h2o + (2) nadp | 2.3.1.85 |
| FAS120 | [c]: dca + (3) h + malcoa + (2) nadph --> co2 + coa + ddca + h2o + (2) nadp | 2.3.1.85 |
| FAS140 | [c]: ddca + (3) h + malcoa + (2) nadph --> co2 + coa + h2o + (2) nadp + ttdca | 2.3.1.85 |
| FAS160 | [c]: (3) h + malcoa + (2) nadph + ttdca --> co2 + coa + h2o + hdca + (2) nadp | 2.3.1.85 |
| FAS180 | [c]: (3) h + hdca + malcoa + (2) nadph --> co2 + coa + h2o + (2) nadp + ocdca | 2.3.1.85 |
| FAS200 | [c]: (3) h + malcoa + (2) nadph + ocdca --> co2 + coa + ecsa + h2o + (2) nadp | 2.3.1.85 |
| FAS220 | [c]: ecsa + (3) h + malcoa + (2) nadph --> co2 + coa + dcsa + h2o + (2) nadp | 2.3.1.85 |
| FAS240 | [c]: dcsa + (3) h + malcoa + (2) nadph --> co2 + coa + h2o + (2) nadp + ttc | 2.3.1.85 |
| FAS80_L | [c]: accoa + (8) h + (3) malcoa + (6) nadph --> (3) co2 + (4) coa + (2) h2o + (6) nadp + octa | 2.3.1.85 |
| FBA | [c]: fdp <==> dhap + g3p | 4.1.2.13 |
| FBP | [c]: fdp + h2o --> f6p + pi | 3.1.3.11 |
| FCLTm | [m]: fe2 + ppp9 --> h + pheme | 4.99.1.1 |
| FE2trm | fe2[c] <==> fe2[m] | |
| FKYNH | [c]: Lfmkynr + h2o --> for + h + kynr-L | 3.5.1.9 |
| FldAct | [c]: fald + thf --> h2o + mlthf | |
| FMETDH | [c]: 10fthf + h2o + nadp --> co2 + h + nadph + thf | 1.5.1.6 |
| FOLt | fol[e] + h[e] <==> fol[c] + h[c] | |
| FORter | for[c] <==> for[r] | |
| FORTHFC | [c]: 5fthf + (2) h <==> methf + nh4 | 4.3.1.4 |
| FRDPter | frdp[c] <==> frdp[r] | |
| FTHFLm | [m]: atp + for + thf <==> 10fthf + adp + pi | 6.3.4.3 |
| FTHFLr | [c]: atp + for + thf <==> 10fthf + adp + pi | 6.3.4.3 |
| FUM | [c]: fum + h2o <==> mal-L | 4.2.1.2 |
| FUM2tm | fum[c] + mal-L[m] <==> fum[m] + mal-L[c] | |
| FUMACA | [c]: 4fumacac + h2o --> acac + fum + h | 3.7.1.2 |
| FUMm | [m]: fum + h2o <==> mal-L | 4.2.1.2 |
| G3PD1 | [c]: glyc3p + nad <==> dhap + h + nadh | 1.1.1.94 |
| G3PDcm | fad[m] + glyc3p[c] --> dhap[c] + fadh2[m] | 1.1.99.5 |
| G5SADs | [c]: glu5sa <==> 1pyr5c + h + h2o | |
| G5SADsm | [m]: glu5sa <==> 1pyr5c + h + h2o | |
| G5SDm | [m]: glu5p + h + nadph --> glu5sa + nadp + pi | 1.2.1.41 |
| G6PASEer | [r]: g6p + h2o --> glc-D + pi | 3.1.3.9 |
| G6PDH2er | [r]: g6p + nadp --> 6pgl + h + nadph | 1.1.1.49 |
| G6PDHy | [c]: g6p + nadp <==> 6pgl + h + nadph | 1.1.1.49 |
| G6Pter | g6p[c] <==> g6p[r] | |
| GACm | asp-L[m] + glu-L[c] + h[c] --> asp-L[c] + glu-L[m] + h[m] | |
| GALU | [c]: g1p + h + utp <==> ppi + udpg | 2.7.7.9 |
| GAPD | [c]: g3p + nad + pi <==> 13dpg + h + nadh | 1.2.1.12 |
| GARFTi | [c]: 10fthf + gar --> fgam + h + thf | 2.1.2.2 |
| GAT_CHO | [c]: (0.025) arachdcoa + (0.016) clpndcoa + (0.01) cvncoa + (0.002) ecsacoa + (0.003) ecspecoa + (0.004) estcoa + glyc3p + (0.064) hdcoa + (0.007) lgnccoa + (0.003) lnlecoa + (0.008) nrvnccoa + (0.042) ocdycacoa + (0.404) odecoa + (0.253) pmtcoa + (0.13) strcoa + (0.029) tdcoa --> (0.001) 1ag3p_CHO + coa | 2.3.1.15 |
| GCOADrm | [m]: fad + glutcoa + h <==> b2coa + co2 + fadh2 | 1.3.99.7 |
| GGTA | [c]: gthrd + h2o --> cgly + glu-L | 2.3.2.2 |
| GHMT | [c]: ser-L + thf <==> gly + mlthf | 2.1.2.1 |
| GHMT2m | [m]: ser-L + thf <==> gly + h2o + mlthf | 2.1.2.1 |
| GK1 | [c]: atp + gmp <==> adp + gdp | 2.7.4.8 |
| GL3Ptrm | glyc3p[c] <==> glyc3p[m] | |
| GLCP | [c]: glycogen + pi --> g1p | 2.4.1.1 |
| GLCt1r | glc-D[e] <==> glc-D[c] | |

TABLE 4-continued

Reactions and Metabolites in CHO Model

| | | |
|---|---|---|
| GLCter | glc-D[c] <==> glc-D[r] | |
| GLNS | [c]: atp + glu-L + nh4 --> adp + gln-L + h + pi | 6.3.1.2 |
| GLNt4r | gln-L[e] + na1[e] <==> gln-L[c] + na1[c] | |
| GLNtrm | gln-L[c] + h[c] <==> gln-L[m] + h[m] | |
| GLU5Km | [m]: atp + glu-L --> adp + glu5p | 2.7.2.11 |
| GLUCYSL | [c]: atp + cys-L + glu-L --> adp + glucys + h + pi | 6.3.2.2 |
| GLUDxm | [m]: glu-L + h2o + nad <==> akg + h + nadh + nh4 | 1.4.1.3 |
| GLUDym | [m]: glu-L + h2o + nadp <==> akg + h + nadph + nh4 | 1.4.1.3 |
| GLUFT | [c]: 5fthf + glu-L <==> forglu + thf | 2.1.2.5 |
| GLUNm | [m]: gln-L + h2o --> glu-L + nh4 | 3.5.1.2 |
| GLUPRT | [c]: gln-L + h2o + prpp --> glu-L + ppi + pram | 2.4.2.14 |
| GLUSAtm | glu5sa[c] <==> glu5sa[m] | |
| GLUt2m | glu-L[c] + h[c] <==> glu-L[m] + h[m] | |
| GLUt4 | glu-L[e] + na1[e] <==> glu-L[c] + na1[c] | |
| GLYATm | [m]: accoa + gly <==> 2aobut + coa | 2.3.1.29 |
| GLYCLm | [m]: gly + nad + thf --> co2 + mlthf + nadh + nh4 | 2.1.2.10 |
| GLYGS | [c]: udpg --> glycogen + h + udp | 2.4.1.11 |
| GLYt4r | gly[e] + na1[e] <==> gly[c] + na1[c] | |
| GLYtm | gly[c] <==> gly[m] | |
| GLYtp | gly[c] <==> gly[x] | |
| GMPS2 | [c]: atp + gln-L + h2o + xmp --> amp + glu-L + gmp + (2) h + ppi | 6.3.5.2 |
| GMTR | [c]: amet + gly --> ahcys + h + sarcs | 2.1.1.20 |
| GRTT | [c]: grdp + ipdp --> frdp + ppi | 2.5.1.10 |
| GTHO | [c]: gthox + h + nadph --> (2) gthrd + nadp | 1.8.1.7 |
| GTHP | [c]: (2) gthrd + h2o2 <==> gthox + (2) h2o | 1.11.1.9 |
| GTHSr | [c]: atp + glucys + gly <==> adp + gthrd + h + pi | 6.3.2.3 |
| GTPCI | [c]: gtp + h2o --> andt + for + h | 3.5.4.16 |
| H2O2tm | h2o2[c] <==> h2o2[m] | |
| H2O2tp | h2o2[c] <==> h2o2[x] | |
| H2Ot5 | h2o[e] <==> h2o[c] | |
| H2Oter | h2o[c] <==> h2o[r] | |
| H2Otm | h2o[c] <==> h2o[m] | |
| H2Otp | h2o[c] <==> h2o[x] | |
| HACD1m | [m]: aacoa + h + nadh <==> 3hbycoa + nad | 1.1.1.35 |
| HACD8m | [m]: 3hmbcoa + nad <==> 2maacoa + h + nadh | 1.1.1.178 |
| HANTHDOr | [c]: 3hanthrn + o2 <==> acmucsal | 1.13.11.6 |
| HCO3E | [c]: co2 + h2o <==> h + hco3 | 4.2.1.1 |
| HCO3Em | [m]: co2 + h2o <==> h + hco3 | 4.2.1.1 |
| HDCEAtr | hdcea[e] <==> hdcea[c] | |
| HEX1 | [c]: atp + glc-D --> adp + g6p + h | 2.7.1.2 |
| HGENDO | [c]: hgentis + o2 --> 4mlacac + h | 1.13.11.5 |
| HIBDm | [m]: 3hmp + nad <==> h + mmalsa-S + nadh | 1.1.1.31 |
| HIBHm | [m]: h2o + hibcoa --> 3hmp + coa + h | 3.1.2.4 |
| HISD1r | [c]: his-L <==> nh4 + urcan | 4.3.1.3 |
| HISt4r | his-L[e] + na1[e] <==> his-L[c] + na1[c] | |
| HMBS | [c]: h2o + (4) ppbng --> hmbil + (4) nh4 | 2.5.1.61 |
| HMGCOAR | [c]: coa + mev-R + (2) nadp <==> (2) h + hmgcoa + (2) nadph | 1.1.1.34 |
| HMGCOASi | [c]: aacoa + accoa + h2o --> coa + h + hmgcoa | 4.1.3.5 |
| HMGCOASim | [m]: aacoa + accoa + h2o --> coa + h + hmgcoa | 4.1.3.5 |
| HMGCOAtm | hmgcoa[c] <==> hmgcoa[m] | |
| HMGLm | [m]: hmgcoa --> acac + accoa | 4.1.3.4 |
| HPPDO1 | [c]: 34hpp + o2 --> co2 + hgentis | 1.13.11.27 |
| ICDHxm | [m]: icit + nad --> akg + co2 + nadh | 1.1.1.41 |
| ICDHy | [c]: icit + nadp <==> akg + co2 + nadph | 1.1.1.42 |
| ICDHym | [m]: icit + nadp --> akg + co2 + nadph | 1.1.1.42 |
| ILEt5m | ile-L[c] <==> ile-L[m] | |
| ILETAm | [m]: akg + ile-L <==> 3mop + glu-L | 2.6.1.42 |
| ILEtec | ile-L[e] <==> ile-L[c] | |
| IMPC | [c]: h2o + imp <==> fprica | 3.5.4.10 |
| IMPD | [c]: h2o + imp + nad --> h + nadh + xmp | 1.1.1.205 |
| INSTt2r | h[e] + inost[e] <==> h[c] + inost[c] | |
| IPDDIp | [x]: ipdp <==> dmpp | 5.3.3.2 |
| IPDPtp | ipdp[x] <==> ipdp[c] | |
| IZPN | [c]: 4izp + h2o --> forglu | 3.5.2.7 |
| KYNASE3 | [c]: h2o + hkyn --> 3hanthrn + ala-L + h | 3.7.1.3 |
| KYNMOr | [c]: h + kynr-L + nadph + o2 <==> h2o + hkyn + nadp | 1.14.13.9 |
| L-LACt2 | h[e] + lac-L[e] <==> h[c] + lac-L[c] | |
| LATHSTOxer | [r]: h + lathost + nadh + o2 --> 7dhchsterol + (2) h2o + nad | 1.14.21.6 |
| LATHSTOyer | [r]: h + lathost + nadph + o2 --> 7dhchsterol + (2) h2o + nadp | 1.14.21.6 |
| LDH_L | [c]: lac-L + nad <==> h + nadh + pyr | 1.1.1.27 |
| LEUTAm | [m]: akg + leu-L <==> 4mop + glu-L | 2.6.1.42 |
| LEUtec | leu-L[e] <==> leu-L[c] | |

TABLE 4-continued

Reactions and Metabolites in CHO Model

| | | |
|---|---|---|
| LEUtm | leu-L[c] <==> leu-L[m] | |
| LGNCt | ttc[e] <==> ttc[c] | |
| LNLNEtr | lnlne[e] <==> lnlne[c] | |
| LNS14DMer | [r]: (2) h + lanost + (3) nadph + (3) o2 --> 44mctr + for + (4) h2o + (3) nadp | 1.14.13.70 |
| LNSTLSer | [r]: Ssq23epx --> lanost | 5.4.99.7 |
| LSTO1er | [r]: cholsd + h + nadph + o2 --> ddsmsterol + (2) h2o + nadp | 1.14.21.6 |
| LYSt | lys-L[e] <==> lys-L[c] | |
| LYStm | h[m] + lys-L[c] <==> h[c] + lys-L[m] | |
| MAGH_CHO | [c]: h2o + (0.001) mglyc_CHO --> (0.025) arachda + (0.01) dcshea + (0.016) dcspea + (0.002) ecsa + (0.003) ecspea + (0.004) ecstea + glyc + h + (0.253) hdca + (0.064) hdcea + (0.003) lnlne + (0.008) nrvnc + (0.13) ocdca + (0.404) ocdcea + (0.042) ocdcya + (0.007) ttc + (0.029) ttdca | 6.2.1.3 |
| MALAKGtm | akg[m] + mal-L[c] <==> akg[c] + mal-L[m] | |
| MALOAtm | mal-L[m] + oaa[c] <==> mal-L[c] + oaa[m] | |
| MALtm | mal-L[c] + pi[m] <==> mal-L[m] + pi[c] | |
| MCCCm | [m]: 3mb2coa + atp + hco3 --> 3mgcoa + adp + h + pi | 6.4.1.4 |
| MCPST | [c]: mercppyr + so3 --> pyr + tsul | 2.8.1.2 |
| MDH | [c]: mal-L + nad <==> h + nadh + oaa | 1.1.1.37 |
| MDHm | [m]: mal-L + nad <==> h + nadh + oaa | 1.1.1.37 |
| ME1m | [m]: mal-L + nad --> co2 + nadh + pyr | 1.1.1.38 |
| ME2r | [c]: mal-L + nadp <==> co2 + nadph + pyr | 1.1.1.40 |
| ME2rm | [m]: mal-L + nadp <==> co2 + nadph + pyr | 1.1.1.40 |
| METAT | [c]: atp + h2o + met-L --> amet + pi + ppi | 2.5.1.6 |
| METFR | [c]: 5mthf + nadp <==> (2) h + mlthf + nadph | 1.5.1.20 |
| METS | [c]: 5mthf + hcys-L --> h + met-L + thf | 2.1.1.13 |
| METt4r | met-L[e] + na1[e] <==> met-L[c] + na1[c] | |
| MEVK1p | [x]: atp + mev-R --> 5pmev + adp + h | 2.7.1.36 |
| MEVtp | mev-R[x] <==> mev-R[c] | |
| MGCHm | [m]: 3mgcoa + h2o <==> hmgcoa | 4.2.1.18 |
| MI1PP | [c]: h2o + mi1p-D --> inost + pi | 3.1.3.25 |
| MI1PS | [c]: g6p --> mi1p-D | 5.5.1.4 |
| MLACI | [c]: 4mlacac --> 4fumacac | 5.2.1.2 |
| MLTHFtm | mlthf[c] <==> mlthf[m] | |
| MMALSAtm | mmalsa-S[m] <==> mmalsa-S[c] | |
| MMALtm | mmal[m] <==> mmal[c] | |
| MMCOAHm | [m]: coa + h + mmal --> h2o + mmcoa-S | 3.1.2.17 |
| MMEm | [m]: mmcoa-S <==> mmcoa-R | 5.1.99.1 |
| MMMrm | [m]: mmcoa-R <==> succoa | 5.4.99.2 |
| MMSDHim | [m]: coa + mmalsa-S + nad --> co2 + nadh + ppcoa | 1.2.1.27 |
| MOBD1m | [m]: 4mop + coa + nad --> co2 + ivcoa + nadh | |
| MOBD2m | [m]: 3mob + coa + nad --> co2 + ibcoa + nadh | |
| MOBD3m | [m]: 3mop + coa + nad --> 2mbcoa + co2 + nadh | |
| MTHFC | [c]: h2o + methf <==> 10fthf + h | 3.5.4.9 |
| MTHFCm | [m]: h2o + methf <==> 10fthf + h | 3.5.4.9 |
| MTHFD | [c]: mlthf + nadp <==> methf + nadph | 1.5.1.5 |
| MTHFD2m | [m]: mlthf + nad <==> methf + nadh | 1.5.1.5 |
| MTHFDm | [m]: mlthf + nadp <==> methf + nadph | 1.5.1.5 |
| MYRTt5 | ttdca[c] <==> ttdca[e] | |
| NADH4-u10m | (5) h[m] + nadh[m] + ubq10[m] --> (4) h[c] + nad[m] + q10h2[m] | 1.6.5.3 |
| NAt7 | h[e] + na1[c] <==> h[c] + na1[e] | |
| NDP8 | [c]: dudp + h2o --> dump + h + pi | 3.6.1.23 |
| NDPK1 | [c]: atp + gdp <==> adp + gtp | 2.7.4.6 |
| NDPK1m | [m]: atp + gdp <==> adp + gtp | 2.7.4.6 |
| NDPK2 | [c]: atp + udp <==> adp + utp | 2.7.4.6 |
| NDPK3 | [c]: atp + cdp <==> adp + ctp | 2.7.4.6 |
| NDPK3m | [m]: atp + cdp <==> adp + ctp | 2.7.4.6 |
| NDPK4 | [c]: atp + dtdp <==> adp + dttp | 2.7.4.6 |
| NDPK5 | [c]: atp + dgdp <==> adp + dgtp | 2.7.4.6 |
| NDPK7 | [c]: atp + dcdp <==> adp + dctp | 2.7.4.6 |
| NDPK8 | [c]: atp + dadp <==> adp + datp | 2.7.4.6 |
| NH4t | nh4[e] <==> nh4[c] | |
| NH4tm | nh4[c] <==> nh4[m] | |
| NRVNCt | nrvnc[e] <==> nrvnc[c] | |
| O2t | o2[e] <==> o2[c] | |
| O2ter | o2[c] <==> o2[r] | |
| O2tp | o2[c] <==> o2[x] | |
| O2trm | o2[c] <==> o2[m] | |
| OCBTm | [m]: cbp + orn-L <==> citr-L + h + pi | 2.1.3.3 |
| OCDCEAtr | ocdcea[e] <==> ocdcea[c] | |
| OCDCYAtr | ocdcya[e] <==> ocdcya[c] | |
| OCOAT1rm | [m]: acac + succoa <==> aacoa + succ | 2.8.3.5 |
| OMPDC | [c]: h + orot5p --> co2 + ump | 4.1.1.23 |

TABLE 4-continued

Reactions and Metabolites in CHO Model

| | | |
|---|---|---|
| ORNCITRtm | citr-L[m] + h[m] + orn-L[c] <==> citr-L[c] + h[c] + orn-L[m] | |
| ORNDC | [c]: h + orn-L --> co2 + ptrc | 4.1.1.17 |
| ORNTAm | [m]: akg + orn-L <==> glu-L + glu5sa | 2.6.1.13 |
| ORNtrm | h[m] + orn-L[c] <==> h[c] + orn-L[m] | |
| ORPT | [c]: orot5p + ppi <==> orot + prpp | 2.4.2.10 |
| OXOATm | [m]: 2aadp + akg <==> 2oxoadp + glu-L | 2.6.1.39 |
| P5CRx | [c]: 1pyr5c + (2) h + nadh --> nad + pro-L | 1.5.1.2 |
| P5CRy | [c]: 1pyr5c + (2) h + nadph --> nadp + pro-L | 1.5.1.2 |
| PAtm_CHO | pa_CHO[c] <==> pa_CHO[m] | |
| PCm | [m]: atp + hco3 + pyr --> adp + h + oaa + pi | 6.4.1.1 |
| PDHm | [m]: coa + nad + pyr --> accoa + co2 + nadh | 1.2.1.51 |
| PFK | [c]: atp + f6p --> adp + fdp + h | 2.7.1.11 |
| PGCDr | [c]: 3pg + nad <==> 3php + h + nadh | 1.1.1.95 |
| PGDH | [c]: 6pgc + nadp --> co2 + nadph + ru5p-D | 1.1.1.44 |
| PGI | [c]: g6p <==> f6p | 5.3.1.9 |
| PGK | [c]: 13dpg + adp <==> 3pg + atp | 2.7.2.3 |
| PGL | [c]: 6pgl + h2o --> 6pgc + h | 3.1.1.31 |
| PGLer | [r]: 6pgl + h2o --> 6pgc + h | 3.1.1.31 |
| PGM | [c]: 3pg <==> 2pg | 5.4.2.1 |
| PGMT | [c]: g1p <==> g6p | 5.4.2.2 |
| PGPPAm_CHO | [m]: h2o + (0.001) pgp_CHO --> (0.001) pg_CHO + pi | 3.1.3.27 |
| PHE4MO | [c]: o2 + phe-L + thbpt --> dhbpt + h2o + tyr-L | 1.14.16.1 |
| PHEMEtm | pheme[m] <==> pheme[c] | |
| PHEMEtr | pheme[e] <==> pheme[c] | |
| PHEtec | phe-L[e] <==> phe-L[c] | |
| PINOS_CHO | [c]: (0.001) cdpdag_CHO + inost <==> cmp + h + (0.001) pino_CHO | 2.7.8.11 |
| PIt2p | h[c] + pi[c] <==> h[x] + pi[x] | |
| PIt6 | h[e] + pi[e] <==> h[c] + pi[c] | |
| PIter | h[c] + pi[c] <==> h[r] + pi[r] | |
| PItm | h[c] + pi[c] <==> h[m] + pi[m] | |
| PLIPA1_CHO | [c]: h2o + (0.001) pc_CHO --> (0.001) 1aglycpc_CHO + (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.008) nrvnc + (0.13) ocdca + (0.404) ocdcea + (0.042) ocdcya + (0.007) ttc + (0.029) ttdca | 3.1.1.4 |
| PMEVKrp | [x]: 5pmev + atp <==> 5dpmev + adp | 2.7.4.2 |
| PMTt5 | hdca[c] <==> hdca[e] | |
| PNTK | [c]: atp + pnto-R --> 4ppan + adp + h | 2.7.1.33 |
| PNTOt4 | na1[e] + pnto-R[e] --> na1[c] + pnto-R[c] | |
| PPA | [c]: h2o + ppi --> h + (2) pi | 3.6.1.1 |
| PPA2 | [c]: h2o + pppi --> h + pi + ppi | 3.6.1.25 |
| PPAer | [r]: h2o + ppi --> h + (2) pi | 3.6.1.1 |
| PPAm | [m]: h2o + ppi --> h + (2) pi | 3.6.1.1 |
| PPBNGS | [c]: (2) 5aop --> h + (2) h2o + ppbng | 4.2.1.24 |
| PPCDC | [c]: 4ppcys + h --> co2 + pan4p | 4.1.1.36 |
| PPCKG | [c]: gtp + oaa --> co2 + gdp + pep | 4.1.1.32 |
| PPCKGm | [m]: gtp + oaa --> co2 + gdp + pep | 4.1.1.32 |
| PPCOACrm | [m]: atp + hco3 + ppcoa <==> adp + h + mmcoa-S + pi | 6.4.1.3 |
| PPNCL | [c]: 4ppan + ctp + cys-L --> 4ppcys + cdp + h + pi | 6.3.2.5 |
| PPP9tm | ppp9[m] <==> ppp9[c] | |
| PPPGO | [c]: (1.5) o2 + pppg9 --> (3) h2o + ppp9 | 1.3.3.4 |
| PRAGS | [c]: atp + gly + pram --> adp + gar + h + pi | 6.3.4.13 |
| PRAIS | [c]: atp + fpram --> adp + air + h + pi | 6.3.3.1 |
| PRASCS | [c]: 5aizc + asp-L + atp <==> 25aics + adp + h + pi | 6.3.2.6 |
| PRFGS | [c]: atp + fgam + gln-L + h2o --> adp + fpram + glu-L + (2) h + pi | 6.3.5.3 |
| PRO1xm | [m]: nad + pro-L --> 1pyr5c + (2) h + nadh | 1.5.1.2 |
| PROt5 | na1[e] + pro-L[e] <==> na1[c] + pro-L[c] | |
| PROtm | pro-L[c] <==> pro-L[m] | |
| PRPPS | [c]: atp + r5p <==> amp + h + prpp | 2.7.6.1 |
| PSERD_CHO | [c]: h + (0.001) ps_CHO --> co2 + (0.001) pe_CHO | 4.1.1.65 |
| PSERTr | [c]: 3php + glu-L <==> akg + pser-L | 2.6.1.52 |
| PSP_L | [c]: h2o + pser-L --> pi + ser-L | 3.1.3.3 |
| PTDSS1_CHO | [c]: chol + (0.001) ps_CHO <==> (0.001) pc_CHO + ser-L | |
| PTHPS | [c]: ahdt --> 6pthp + pppi | 4.2.3.12 |
| PTPAT | [c]: atp + h + pan4p <==> dpcoa + ppi | 2.7.7.3 |
| PTRCtm | ptrc[m] <==> ptrc[c] | |
| PYK | [c]: adp + h + pep --> atp + pyr | 2.7.1.40 |
| PYR5CDxm | [m]: glu5sa + h2o + nad --> glu-L + (2) h + nadh | 1.5.1.12 |
| PYRtm | h[c] + pyr[c] <==> h[m] + pyr[m] | |
| RNDR1 | [c]: adp + trdrd --> dadp + h2o + trdox | 1.17.4.1 |

TABLE 4-continued

Reactions and Metabolites in CHO Model

| | | |
|---|---|---|
| RNDR2 | [c]: gdp + trdrd --> dgdp + h2o + trdox | 1.17.4.1 |
| RNDR3 | [c]: cdp + trdrd --> dcdp + h2o + trdox | 1.17.4.1 |
| RNDR4 | [c]: trdrd + udp --> dudp + h2o + trdox | 1.17.4.1 |
| RPE | [c]: ru5p-D <==> xu5p-D | 5.1.3.1 |
| RPI | [c]: r5p <==> ru5p-D | 5.3.1.6 |
| SACCDGm | [m]: Lsacchrp + h2o + nad <==> ampsal + glu-L + h + nadh | 1.5.1.9 |
| SACCDym | [m]: akg + h + lys-L + nadph --> Lsacchrp + h2o + nadp | 1.5.1.8 |
| SARCOp | [x]: h2o + o2 + sarcs --> fald + gly + h2o2 | 1.5.3.1 |
| SARCStrp | sarcs[c] <==> sarcs[x] | |
| SERD_L | [c]: ser-L --> nh4 + pyr | 4.3.1.17 |
| SERPT | [c]: h + pmtcoa + ser-L --> 3dsphgn + co2 + coa | 2.3.1.50 |
| SERt4r | na1[e] + ser-L[e] <==> na1[c] + ser-L[c] | |
| SERtm | ser-L[c] <==> ser-L[m] | |
| SO3t2r | na1[e] + so3[e] <==> na1[c] + so3[c] | |
| SOD | [c]: (2) h + (2) o2- --> h2o2 + o2 | 1.15.1.1 |
| SODm | [m]: (2) h + (2) o2- --> h2o2 + o2 | 1.15.1.1 |
| SODp | [x]: (2) h + (2) o2- --> h2o2 + o2 | 1.15.1.1 |
| SPMS | [c]: ametam + ptrc --> 5mta + h + spmd | 2.5.1.16 |
| SPRr | [c]: 6pthp + (2) h + (2) nadph <==> (2) nadp + thbpt | 1.1.1.153 |
| SPRS | [c]: ametam + spmd --> 5mta + h + sprm | 2.5.1.22 |
| SPYR | [c]: h2o + spyr --> (2) h + pyr + so3 | |
| SQLEer | [r]: h + nadph + o2 + sql --> Ssq23epx + h2o + nadp | 1.14.99.7 |
| SQLSer | [r]: (2) frdp + h + nadph --> nadp + (2) ppi + sql | 2.5.1.21 |
| SSALxm | [m]: h2o + nad + sucsal --> (2) h + nadh + succ | 1.2.1.24 |
| STRR2er | [r]: h + nadph + zymst --> nadp + zymstnl | 1.3.1.72 |
| STRR3er | [r]: dsmsterol + h + nadph --> chsterol + nadp | 1.3.1.72 |
| STRRer | [r]: cholsd + h + nadph --> lathost + nadp | 1.3.1.72 |
| STRt5 | ocdca[c] <==> ocdca[e] | |
| SUCD1m-ubq10 | [m]: succ + ubq10 <==> fum + q10h2 | 1.3.5.1 |
| SUCD3m-ubq10 | [m]: fadh2 + ubq10 <==> fad + q10h2 | |
| SUCOASAm | [m]: atp + coa + succ <==> adp + pi + succoa | 6.2.1.5 |
| SUCOASGm | [m]: coa + gtp + succ <==> gdp + pi + succoa | 6.2.1.4 |
| TAL | [c]: g3p + s7p <==> e4p + f6p | 2.2.1.2 |
| THD1im | h[c] + nadh[m] + nadp[m] --> h[m] + nad[c] + nadph[m] | 1.6.1.1 |
| THFtm | thf[c] <==> thf[m] | |
| THRDm | [m]: nad + thr-L --> 2aobut + h + nadh | 1.1.1.103 |
| THRt2m | h[c] + thr-L[c] <==> h[m] + thr-L[m] | |
| THRt4r | na1[e] + thr-L[e] <==> na1[c] + thr-L[c] | |
| TKT1 | [c]: r5p + xu5p-D <==> g3p + s7p | 2.2.1.1 |
| TKT2 | [c]: e4p + xu5p-D <==> f6p + g3p | 2.2.1.1 |
| TMDSr | [c]: dump + mlthf <==> dhf + dtmp | 2.1.1.45 |
| TPI | [c]: dhap <==> g3p | 5.3.1.1 |
| TRDRr | [c]: h + nadph + trdox <==> nadp + trdrd | 1.8.1.9 |
| TRIGH_CHO | [c]: h2o + (0.001) triglyc_CHO --> (0.001) 12dgr_CHO + (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.008) nrvnc + (0.13) ocdca + (0.404) ocdcea + (0.042) ocdcya + (0.007) ttc + (0.029) ttdca | 6.2.1.3 |
| TRIGS_CHO | [c]: (0.001) 12dgr_CHO + (0.001) facoa_avg_CHO --> coa + (0.001) triglyc_CHO | 2.3.1.20 |
| TRPO2 | [c]: o2 + trp-L --> Lfmkynr | 1.13.11.11 |
| TRPt | trp-L[e] <==> trp-L[c] | |
| TYRt | tyr-L[e] <==> tyr-L[c] | |
| TYRTA | [c]: akg + tyr-L <==> 34hpp + glu-L | 2.6.1.5 |
| UMPK | [c]: atp + ump <==> adp + udp | 2.7.4.14 |
| UPP3S | [c]: hmbil --> h2o + uppg3 | 4.2.1.75 |
| UPPDC1 | [c]: (4) h + uppg3 --> (4) co2 + cpppg3 | 4.1.1.37 |
| URCN | [c]: h2o + urcan --> 4izp | 4.2.1.49 |
| UREAt | urea[e] <==> urea[c] | |
| UREAtm | urea[c] <==> urea[m] | |
| VALTAm | [m]: akg + val-L <==> 3mob + glu-L | 2.6.1.42 |
| VALtec | val-L[e] <==> val-L[c] | |
| VALtm | val-L[c] <==> val-L[m] | |

| Abbreviation | Equation | |
|---|---|---|
| Biomass_CHO2 | [c]: (0.5291) ala-L + (0.3501) arg-L + (0.2172) asn-L + (0.2673) asp-L + (0.0315) atp + (0.000038) cholse_CHO + (0.0599) chsterol + (0.000001) clpn_CHO + (0.0526) ctp + (0.1559) cys-L + (0.0172) datp + (0.0114) dctp + (0.0114) dgtp + (0.0172) dttp + (0.2896) gln-L + (0.3564) glu-L + (0.4344) gly + (0.3885) glycogen + (0.0596) gtp + | |

TABLE 4-continued

Reactions and Metabolites in CHO Model

|   |   |
|---|---|
|   | (0.1225) his-L + (0.2896) ile-L + (0.4901) leu-L + (0.4957) lys-L + (0.1114) met-L + (0.000089) pc_CHO + (0.000036) pe_CHO + (0.117) phe-L + (0.000012) pino_CHO + (0.1559) pro-L + (0.000012) ps_CHO + (0.3174) ser-L + (0.000017) sphgmy_CHO + (0.3397) thr-L + (0.000007) triglyc_CHO + (0.0334) trp-L + (0.1114) tyr-L + (0.0315) utp + (0.3286) val-L --> |
| EX_ala-L(e) | [e]: ala-L <==> |
| EX_arachda(e) | [e]: arachda <==> |
| EX_arg-L(e) | [e]: arg-L <==> |
| EX_asn-L(e) | [e]: asn-L <==> |
| EX_asp-L(e) | [e]: asp-L <==> |
| EX_chol(e) | [e]: chol <==> |
| EX_co2(e) | [e]: co2 <==> |
| EX_cys-L(e) | [e]: cys-L <==> |
| EX_dcshea(e) | [e]: dcshea <==> |
| EX_dcspea(e) | [e]: dcspea <==> |
| EX_ecsa(e) | [e]: ecsa <==> |
| EX_ecspea(e) | [e]: ecspea <==> |
| EX_ecstea(e) | [e]: ecstea <==> |
| EX_etha(e) | [e]: etha <==> |
| EX_fol(e) | [e]: fol <==> |
| EX_glc(e) | [e]: glc-D <==> |
| EX_gln-L(e) | [e]: gln-L <==> |
| EX_glu-L(e) | [e]: glu-L <==> |
| EX_gly(e) | [e]: gly <==> |
| EX_h(e) | [e]: h <==> |
| EX_h2o(e) | [e]: h2o <==> |
| EX_hdca(e) | [e]: hdca <==> |
| EX_hdcea(e) | [e]: hdcea <==> |
| EX_his-L(e) | [e]: his-L <==> |
| EX_ile-L(e) | [e]: ile-L <==> |
| EX_inost(e) | [e]: inost <==> |
| EX_lac-L(e) | [e]: lac-L <==> |
| EX_leu-L(e) | [e]: leu-L <==> |
| EX_lnlne(e) | [e]: lnlne <==> |
| EX_lys-L(e) | [e]: lys-L <==> |
| EX_met-L(e) | [e]: met-L <==> |
| EX_na1(e) | [e]: na1 <==> |
| EX_nh4(e) | [e]: nh4 <==> |
| EX_nrvnc(e) | [e]: nrvnc <==> |
| EX_o2(e) | [e]: o2 <==> |
| EX_ocdca(e) | [e]: ocdca <==> |
| EX_ocdcea(e) | [e]: ocdcea <==> |
| EX_ocdcya(e) | [e]: ocdcya <==> |
| EX_phe-L(e) | [e]: phe-L <==> |
| EX_pheme(e) | [e]: pheme <==> |
| EX_pi(e) | [e]: pi <==> |
| EX_pnto-R(e) | [e]: pnto-R <==> |
| EX_pro-L(e) | [e]: pro-L <==> |
| EX_ser-L(e) | [e]: ser-L <==> |
| EX_so3(e) | [e]: so3 <==> |
| EX_thr-L(e) | [e]: thr-L <==> |
| EX_trp-L(e) | [e]: trp-L <==> |
| EX_ttc(e) | [e]: ttc <==> |
| EX_ttdca(e) | [e]: ttdca <==> |
| EX_tyr-L(e) | [e]: tyr-L <==> |
| EX_urea(e) | [e]: urea <==> |
| EX_val-L(e) | [e]: val-L <==> |

| Metab Abbreviation | Name | Compartment |
|---|---|---|
| 10fthf | 10-Formyltetrahydrofolate | Cytosol |
| 10fthf | 10-Formyltetrahydrofolate | Mitochondria |
| 12dgr_CHO | 1,2-Diacylglycerol, CHO | Cytosol |
| 13dpg | 3-Phospho-D-glyceroyl phosphate | Cytosol |
| 1ag3p_CHO | 1-Acyl-sn-glycerol 3-phosphate, CHO | Cytosol |
| 1aglycpc_CHO | 1-Acyl-sn-glycero-3-phosphocholine, CHO specific | Cytosol |
| 1pyr5c | 1-Pyrroline-5-carboxylate | Cytosol |
| 1pyr5c | 1-Pyrroline-5-carboxylate | Mitochondria |
| 25aics | (S)-2-[5-Amino-1-(5-phospho-D-ribosyl)imidazole-4-carboxamido]succinate | Cytosol |
| 2aadp | L-2-Aminoadipate | Mitochondria |
| 2amuc | 2-Aminomuconate | Cytosol |
| 2aobut | L-2-Amino-3-oxobutanoate | Mitochondria |
| 2maacoa | 2-Methyl-3-acetoacetyl-CoA | Mitochondria |
| 2mb2coa | trans-2-Methylbut-2-enoyl-CoA | Mitochondria |

TABLE 4-continued

Reactions and Metabolites in CHO Model

| | | |
|---|---|---|
| 2mbcoa | 2-Methylbutanoyl-CoA | Mitochondria |
| 2mp2coa | 2-Methylprop-2-enoyl-CoA | Mitochondria |
| 2obut | 2-Oxobutanoate | Cytosol |
| 2obut | 2-Oxobutanoate | Mitochondria |
| 2oxoadp | 2-Oxoadipate | Cytosol |
| 2oxoadp | 2-Oxoadipate | Mitochondria |
| 2pg | D-Glycerate 2-phosphate | Cytosol |
| 34hpp | 3-(4-Hydroxyphenyl)pyruvate | Cytosol |
| 3dsphgn | 3-Dehydrosphinganine | Cytosol |
| 3hanthrn | 3-Hydroxyanthranilate | Cytosol |
| 3hbycoa | (S)-3-Hydroxybutyryl-CoA | Mitochondria |
| 3hmbcoa | (S)-3-Hydroxy-2-methylbutyryl-CoA | Mitochondria |
| 3hmp | (S)-3-hydroxyisobutyrate | Mitochondria |
| 3mb2coa | 3-Methylbut-2-enoyl-CoA | Mitochondria |
| 3mgcoa | 3-Methylglutaconyl-CoA | Mitochondria |
| 3mob | 3-Methyl-2-oxobutanoate | Mitochondria |
| 3mop | (S)-3-Methyl-2-oxopentanoate | Mitochondria |
| 3pg | 3-Phospho-D-glycerate | Cytosol |
| 3php | 3-Phosphohydroxypyruvate | Cytosol |
| 3sala | 3-Sulfino-L-alanine | Cytosol |
| 3sala | 3-Sulfino-L-alanine | Mitochondria |
| 44mctr | 4,4-dimethylcholesta-8,14,24-trienol | Endoplasmic Reticulum |
| 44mzym | 4,4-dimethylzymosterol | Endoplasmic Reticulum |
| 4abut | 4-Aminobutanoate | Cytosol |
| 4abut | 4-Aminobutanoate | Mitochondria |
| 4abutn | 4-Aminobutanal | Cytosol |
| 4fumacac | 4-Fumarylacetoacetate | Cytosol |
| 4izp | 4-Imidazolone-5-propanoate | Cytosol |
| 4mlacac | 4-Maleylacetoacetate | Cytosol |
| 4mop | 4-Methyl-2-oxopentanoate | Mitochondria |
| 4mzym_int1 | 4-Methylzymosterol intermediate 1 | Endoplasmic Reticulum |
| 4mzym_int2 | 4-Methylzymosterol intermediate 2 | Endoplasmic Reticulum |
| 4ppan | D-4'-Phosphopantothenate | Cytosol |
| 4ppcys | N-((R)-4-Phosphopantothenoyl)-L-cysteine | Cytosol |
| 5aizc | 5-amino-1-(5-phospho-D-ribosyl)imidazole-4-carboxylate | Cytosol |
| 5aop | 5-Amino-4-oxopentanoate | Cytosol |
| 5aop | 5-Amino-4-oxopentanoate | Mitochondria |
| 5dpmev | (R)-5-Diphosphomevalonate | Peroxisome |
| 5fthf | 5-Formiminotetrahydrofolate | Cytosol |
| 5mta | 5-Methylthioadenosine | Cytosol |
| 5mthf | 5-Methyltetrahydrofolate | Cytosol |
| 5pmev | (R)-5-Phosphomevalonate | Peroxisome |
| 6pgc | 6-Phospho-D-gluconate | Cytosol |
| 6pgc | 6-Phospho-D-gluconate | Endoplasmic Reticulum |
| 6pgl | 6-phospho-D-glucono-1,5-lactone | Cytosol |
| 6pgl | 6-phospho-D-glucono-1,5-lactone | Endoplasmic Reticulum |
| 6pthp | 6-Pyruvoyl-5,6,7,8-tetrahydropterin | Cytosol |
| 7dhchsterol | 7-Dehydrocholesterol | Endoplasmic Reticulum |
| aacoa | Acetoacetyl-CoA | Cytosol |
| aacoa | Acetoacetyl-CoA | Mitochondria |
| acac | Acetoacetate | Cytosol |
| acac | Acetoacetate | Mitochondria |
| accoa | Acetyl-CoA | Cytosol |
| accoa | Acetyl-CoA | Mitochondria |
| acmucsal | 2-Amino-3-carboxymuconate semialdehyde | Cytosol |
| acrn | O-Acetylcarnitine | Cytosol |
| acrn | O-Acetylcarnitine | Mitochondria |
| adn | Adenosine | Cytosol |
| adp | ADP | Cytosol |
| adp | ADP | Mitochondria |
| adp | ADP | Peroxisome |
| agm | Agmatine | Mitochondria |
| ahcys | S-Adenosyl-L-homocysteine | Cytosol |
| ahdt | 2-Amino-4-hydroxy-6-(erythro-1,2,3-trihydroxypropyl)dihydropteridine triphosphate | Cytosol |
| aicar | 5-Amino-1-(5-Phospho-D-ribosyl)imidazole-4-carboxamide | Cytosol |
| air | 5-amino-1-(5-phospho-D-ribosyl)imidazole | Cytosol |
| akg | 2-Oxoglutarate | Cytosol |
| akg | 2-Oxoglutarate | Mitochondria |

TABLE 4-continued

Reactions and Metabolites in CHO Model

| | | |
|---|---|---|
| ala-L | L-Alanine | Cytosol |
| ala-L | L-Alanine | Extra-organism |
| amet | S-Adenosyl-L-methionine | Cytosol |
| ametam | S-Adenosylmethioninamine | Cytosol |
| amp | AMP | Cytosol |
| amp | AMP | Mitochondria |
| ampsal | L-2-Aminoadipate 6-semialdehyde | Mitochondria |
| amucsal | 2-Aminomuconate semialdehyde | Cytosol |
| arachda | Arachidonic acid (C20:4) | Cytosol |
| arachda | Arachidonic acid (C20:4) | Extra-organism |
| arachdcoa | arachidonoyl-CoA (C20:4CoA, n-6) | Cytosol |
| arachdcoa | arachidonoyl-CoA (C20:4CoA, n-6) | Mitochondria |
| arachdcrn | C20:4 carnitine | Cytosol |
| arachdcrn | C20:4 carnitine | Mitochondria |
| arg-L | L-Arginine | Cytosol |
| arg-L | L-Arginine | Extra-organism |
| arg-L | L-Arginine | Mitochondria |
| argsuc | N(omega)-(L-Arginino)succinate | Cytosol |
| asn-L | L-Asparagine | Cytosol |
| asn-L | L-Asparagine | Extra-organism |
| asp-L | L-Aspartate | Cytosol |
| asp-L | L-Aspartate | Extra-organism |
| asp-L | L-Aspartate | Mitochondria |
| atp | ATP | Cytosol |
| atp | ATP | Mitochondria |
| atp | ATP | Peroxisome |
| b2coa | trans-But-2-enoyl-CoA | Mitochondria |
| btcoa | Butanoyl-CoA (C4:0CoA) | Mitochondria |
| cbasp | N-Carbamoyl-L-aspartate | Cytosol |
| cbp | Carbamoyl phosphate | Cytosol |
| cbp | Carbamoyl phosphate | Mitochondria |
| cdp | CDP | Cytosol |
| cdp | CDP | Mitochondria |
| cdpchol | CDPcholine | Cytosol |
| cdpdag_CHO | CDPdiacylglycerol, CHO specific | Cytosol |
| cdpdag_CHO | CDPdiacylglycerol, CHO specific | Mitochondria |
| cdpea | CDPethanolamine | Cytosol |
| cer_CHO | ceramide, CHO specific | Cytosol |
| cgly | Cys-Gly | Cytosol |
| chol | Choline | Cytosol |
| chol | Choline | Extra-organism |
| cholp | Choline phosphate | Cytosol |
| cholsd | 5alpha-Cholesta-7,24-dien-3beta-ol | Endoplasmic Reticulum |
| cholse_CHO | Cholesterol ester, CHO specific | Cytosol |
| chsterol | Cholesterol | Cytosol |
| chsterol | Cholesterol | Endoplasmic Reticulum |
| cit | Citrate | Cytosol |
| cit | Citrate | Mitochondria |
| citr-L | L-Citrulline | Cytosol |
| citr-L | L-Citrulline | Mitochondria |
| clpn_CHO | cardiolipin, CHO specific | Cytosol |
| clpn_CHO | cardiolipin, CHO specific | Mitochondria |
| clpndcoa | clupanodonyl CoA (C22:5CoA) | Cytosol |
| clpndcoa | clupanodonyl CoA (C22:5CoA) | Mitochondria |
| clpndcrn | docosapentaenoyl carnitine (C22:5) | Cytosol |
| clpndcrn | docosapentaenoyl carnitine (C22:5) | Mitochondria |
| cmp | CMP | Cytosol |
| cmp | CMP | Mitochondria |
| co2 | CO2 | Cytosol |
| co2 | CO2 | Endoplasmic Reticulum |
| co2 | CO2 | Extra-organism |
| co2 | CO2 | Mitochondria |
| co2 | CO2 | Peroxisome |
| coa | Coenzyme A | Cytosol |
| coa | Coenzyme A | Mitochondria |
| cpppg3 | Coproporphyrinogen III | Cytosol |
| crn | L-Carnitine | Cytosol |
| crn | L-Carnitine | Mitochondria |
| ctp | CTP | Cytosol |
| ctp | CTP | Mitochondria |
| cvncoa | cervonyl CoA (C22:6CoA) | Cytosol |
| cvncoa | cervonyl CoA (C22:6CoA) | Mitochondria |
| cvncrn | cervonyl carnitine (C22:6Crn) | Cytosol |
| cvncrn | cervonyl carnitine (C22:6Crn) | Mitochondria |
| cys-L | L-Cysteine | Cytosol |

TABLE 4-continued

Reactions and Metabolites in CHO Model

| | | |
|---|---|---|
| cys-L | L-Cysteine | Extra-organism |
| cysth-L | L-Cystathionine | Cytosol |
| dadp | dADP | Cytosol |
| datp | dATP | Cytosol |
| dca | Decanoate | Cytosol |
| dcamp | N6-(1,2-Dicarboxyethyl)-AMP | Cytosol |
| dccoa | Decanoyl-CoA (C10:0CoA) | Mitochondria |
| dcdp | dCDP | Cytosol |
| dcer_CHO | dihydroceramide, CHO specific | Cytosol |
| dcsa | docosanoate (n-C22:0) | Cytosol |
| dcshea | docosahexaenoate (C22:6) | Cytosol |
| dcshea | docosahexaenoate (C22:6) | Extra-organism |
| dcspea | docosapentaenoic acid (C22:5) | Cytosol |
| dcspea | docosapentaenoic acid (C22:5) | Extra-organism |
| dctp | dCTP | Cytosol |
| ddca | dodecanoate (C12:0) | Cytosol |
| ddcoa | Dodecanoyl-CoA (n-C12:0CoA) | Mitochondria |
| ddsmsterol | 7-Dehydrodesmosterol | Endoplasmic Reticulum |
| dgdp | dGDP | Cytosol |
| dgtp | dGTP | Cytosol |
| dhap | Dihydroxyacetone phosphate | Cytosol |
| dhbpt | 6,7-Dihydrobiopterin | Cytosol |
| dhf | 7,8-Dihydrofolate | Cytosol |
| dhor-S | (S)-Dihydroorotate | Cytosol |
| dmpp | Dimethylallyl diphosphate | Cytosol |
| dmpp | Dimethylallyl diphosphate | Peroxisome |
| dpcoa | Dephospho-CoA | Cytosol |
| dsmsterol | Desmosterol | Endoplasmic Reticulum |
| dtdp | dTDP | Cytosol |
| dtmp | dTMP | Cytosol |
| dttp | dTTP | Cytosol |
| dudp | dUDP | Cytosol |
| dump | dUMP | Cytosol |
| e4p | D-Erythrose 4-phosphate | Cytosol |
| ecsa | Eicosanoate (n-C20:0) | Cytosol |
| ecsa | Eicosanoate (n-C20:0) | Extra-organism |
| ecsacoa | Eicosanoyl-CoA (n-C20:0CoA) | Cytosol |
| ecsacoa | Eicosanoyl-CoA (n-C20:0CoA) | Mitochondria |
| ecsacrn | eicosanoylcarnitine, C20:0crn | Cytosol |
| ecsacrn | eicosanoylcarnitine, C20:0crn | Mitochondria |
| ecspea | Eicosapentaenoic acid (C20:5) | Cytosol |
| ecspea | Eicosapentaenoic acid (C20:5) | Extra-organism |
| ecspecoa | eicosapentaenoyl-CoA (C20:5CoA) | Cytosol |
| ecspecoa | eicosapentaenoyl-CoA (C20:5CoA) | Mitochondria |
| ecspecrn | eicosapentaenoyl carnitine (C20:5Crn) | Cytosol |
| ecspecrn | eicosapentaenoyl carnitine (C20:5Crn) | Mitochondria |
| ecstea | eicosatrienoate (C20:3) | Cytosol |
| ecstea | eicosatrienoate (C20:3) | Extra-organism |
| estcoa | eicosatrienoyl-CoA (C20:3CoA) | Cytosol |
| estcoa | eicosatrienoyl-CoA (C20:3CoA) | Mitochondria |
| estcrn | eicosatrienoyl carnitine (C20:3Crn) | Cytosol |
| estcrn | eicosatrienoyl carnitine (C20:3Crn) | Mitochondria |
| etha | Ethanolamine | Cytosol |
| etha | Ethanolamine | Extra-organism |
| ethap | Ethanolamine phosphate | Cytosol |
| f6p | D-Fructose 6-phosphate | Cytosol |
| facoa_avg_CHO | Averaged fatty acyl CoA, CHO specific | Cytosol |
| fad | FAD | Mitochondria |
| fadh2 | FADH2 | Mitochondria |
| fald | Formaldehyde | Cytosol |
| fald | Formaldehyde | Peroxisome |
| fdp | D-Fructose 1,6-bisphosphate | Cytosol |
| fe2 | Fe2+ | Cytosol |
| fe2 | Fe2+ | Mitochondria |
| fgam | N2-Formyl-N1-(5-phospho-D-ribosyl)glycinamide | Cytosol |
| ficytcc | Ferricytochrome c | Mitochondria |
| focytcc | Ferrocytochrome c | Mitochondria |
| fol | Folate | Cytosol |
| fol | Folate | Extra-organism |
| for | Formate | Cytosol |
| for | Formate | Endoplasmic Reticulum |
| for | Formate | Mitochondria |
| forglu | N-Formimidoyl-L-glutamate | Cytosol |
| fpram | 2-(Formamido)-N1-(5-phospho-D-ribosyl)acetamidine | Cytosol |

TABLE 4-continued

Reactions and Metabolites in CHO Model

| | | |
|---|---|---|
| fprica | 5-Formamido-1-(5-phospho-D-ribosyl)imidazole-4-carboxamide | Cytosol |
| frdp | Farnesyl diphosphate | Cytosol |
| frdp | Farnesyl diphosphate | Endoplasmic Reticulum |
| fum | Fumarate | Cytosol |
| fum | Fumarate | Mitochondria |
| g1p | D-Glucose 1-phosphate | Cytosol |
| g3p | Glyceraldehyde 3-phosphate | Cytosol |
| g6p | D-Glucose 6-phosphate | Cytosol |
| g6p | D-Glucose 6-phosphate | Endoplasmic Reticulum |
| gar | N1-(5-Phospho-D-ribosyl)glycinamide | Cytosol |
| gdp | GDP | Cytosol |
| gdp | GDP | Mitochondria |
| glc-D | D-Glucose | Cytosol |
| glc-D | D-Glucose | Endoplasmic Reticulum |
| glc-D | D-Glucose | Extra-organism |
| gln-L | L-Glutamine | Cytosol |
| gln-L | L-Glutamine | Extra-organism |
| gln-L | L-Glutamine | Mitochondria |
| glu-L | L-Glutamate | Cytosol |
| glu-L | L-Glutamate | Extra-organism |
| glu-L | L-Glutamate | Mitochondria |
| glu5p | L-Glutamate 5-phosphate | Mitochondria |
| glu5sa | L-Glutamate 5-semialdehyde | Cytosol |
| glu5sa | L-Glutamate 5-semialdehyde | Mitochondria |
| glucys | gamma-L-Glutamyl-L-cysteine | Cytosol |
| glutcoa | Glutaryl-CoA | Mitochondria |
| gly | Glycine | Cytosol |
| gly | Glycine | Extra-organism |
| gly | Glycine | Mitochondria |
| gly | Glycine | Peroxisome |
| glyc | Glycerol | Cytosol |
| glyc3p | sn-Glycerol 3-phosphate | Cytosol |
| glyc3p | sn-Glycerol 3-phosphate | Mitochondria |
| glycogen | Glycogen | Cytosol |
| gmp | GMP | Cytosol |
| grdp | Geranyl diphosphate | Cytosol |
| gthox | Oxidized glutathione | Cytosol |
| gthrd | Reduced glutathione | Cytosol |
| gtp | GTP | Cytosol |
| gtp | GTP | Mitochondria |
| h | H+ | Cytosol |
| h | H+ | Endoplasmic Reticulum |
| h | H+ | Extra-organism |
| h | H+ | Mitochondria |
| h | H+ | Peroxisome |
| h2o | H2O | Cytosol |
| h2o | H2O | Endoplasmic Reticulum |
| h2o | H2O | Extra-organism |
| h2o | H2O | Mitochondria |
| h2o | H2O | Peroxisome |
| h2o2 | Hydrogen peroxide | Cytosol |
| h2o2 | Hydrogen peroxide | Mitochondria |
| h2o2 | Hydrogen peroxide | Peroxisome |
| hco3 | Bicarbonate | Cytosol |
| hco3 | Bicarbonate | Mitochondria |
| hcys-L | L-Homocysteine | Cytosol |
| hdca | hexadecanoate (n-C16:0) | Cytosol |
| hdca | hexadecanoate (n-C16:0) | Extra-organism |
| hdcea | hexadecenoate (n-C16:1) | Cytosol |
| hdcea | hexadecenoate (n-C16:1) | Extra-organism |
| hdcecrn | Hexadecenoyl carnitine | Cytosol |
| hdcecrn | Hexadecenoyl carnitine | Mitochondria |
| hdcoa | Hexadecenoyl-CoA (n-C16:1CoA) | Cytosol |
| hdcoa | Hexadecenoyl-CoA (n-C16:1CoA) | Mitochondria |
| hgentis | Homogentisate | Cytosol |
| hibcoa | (S)-3-Hydroxyisobutyryl-CoA | Mitochondria |
| his-L | L-Histidine | Cytosol |
| his-L | L-Histidine | Extra-organism |
| hkyn | 3-Hydroxy-L-kynurenine | Cytosol |
| hmbil | Hydroxymethylbilane | Cytosol |
| hmgcoa | Hydroxymethylglutaryl-CoA | Cytosol |
| hmgcoa | Hydroxymethylglutaryl-CoA | Mitochondria |

TABLE 4-continued

Reactions and Metabolites in CHO Model

| | | |
|---|---|---|
| hxcoa | Hexanoyl-CoA (C6:0CoA) | Mitochondria |
| ibcoa | Isobutyryl-CoA | Mitochondria |
| icit | Isocitrate | Cytosol |
| icit | Isocitrate | Mitochondria |
| ile-L | L-Isoleucine | Cytosol |
| ile-L | L-Isoleucine | Extra-organism |
| ile-L | L-Isoleucine | Mitochondria |
| imp | IMP | Cytosol |
| inost | myo-Inositol | Cytosol |
| inost | myo-Inositol | Extra-organism |
| ipdp | Isopentenyl diphosphate | Cytosol |
| ipdp | Isopentenyl diphosphate | Peroxisome |
| ivcoa | Isovaleryl-CoA | Mitochondria |
| kynr-L | L-Kynurenine | Cytosol |
| lac-L | L-Lactate | Cytosol |
| lac-L | L-Lactate | Extra-organism |
| lanost | Lanosterol | Endoplasmic Reticulum |
| lathost | Lathosterol | Endoplasmic Reticulum |
| leu-L | L-Leucine | Cytosol |
| leu-L | L-Leucine | Extra-organism |
| leu-L | L-Leucine | Mitochondria |
| Lfmkynr | L-Formylkynurenine | Cytosol |
| lgnccoa | lignocericyl coenzyme A | Cytosol |
| lgnccoa | lignocericyl coenzyme A | Mitochondria |
| lgnccrn | lignoceryl carnitine | Cytosol |
| lgnccrn | lignoceryl carnitine | Mitochondria |
| lnlecoa | Linolenoyl-CoA (C18:3CoA) | Cytosol |
| lnlecoa | Linolenoyl-CoA (C18:3CoA) | Mitochondria |
| lnlecrn | linolenoyl carnitine (C18:3Crn) | Cytosol |
| lnlecrn | linolenoyl carnitine (C18:3Crn) | Mitochondria |
| lnlne | Linolenic acid (C18:3) | Cytosol |
| lnlne | Linolenic acid (C18:3) | Extra-organism |
| Lsacchrp | L-Saccharopine | Mitochondria |
| lys-L | L-Lysine | Cytosol |
| lys-L | L-Lysine | Extra-organism |
| lys-L | L-Lysine | Mitochondria |
| mal-L | L-Malate | Cytosol |
| mal-L | L-Malate | Mitochondria |
| malcoa | Malonyl-CoA | Cytosol |
| mercppyr | Mercaptopyruvate | Cytosol |
| met-L | L-Methionine | Cytosol |
| met-L | L-Methionine | Extra-organism |
| methf | 5,10-Methenyltetrahydrofolate | Cytosol |
| methf | 5,10-Methenyltetrahydrofolate | Mitochondria |
| mev-R | (R)-Mevalonate | Cytosol |
| mev-R | (R)-Mevalonate | Peroxisome |
| mglyc_CHO | monoacylglycerol, CHO specific | Cytosol |
| mi1p-D | 1D-myo-Inositol 1-phosphate | Cytosol |
| mlthf | 5,10-Methylenetetrahydrofolate | Cytosol |
| mlthf | 5,10-Methylenetetrahydrofolate | Mitochondria |
| mmal | Methylmalonate | Cytosol |
| mmal | Methylmalonate | Mitochondria |
| mmalsa-S | (S)-Methylmalonate semialdehyde | Cytosol |
| mmalsa-S | (S)-Methylmalonate semialdehyde | Mitochondria |
| mmcoa-R | (R)-Methylmalonyl-CoA | Mitochondria |
| mmcoa-S | (S)-Methylmalonyl-CoA | Mitochondria |
| na1 | Sodium | Cytosol |
| na1 | Sodium | Extra-organism |
| nad | Nicotinamide adenine dinucleotide | Cytosol |
| nad | Nicotinamide adenine dinucleotide | Endoplasmic Reticulum |
| nad | Nicotinamide adenine dinucleotide | Mitochondria |
| nadh | Nicotinamide adenine dinucleotide - reduced | Cytosol |
| nadh | Nicotinamide adenine dinucleotide - reduced | Endoplasmic Reticulum |
| nadh | Nicotinamide adenine dinucleotide - reduced | Mitochondria |
| nadp | Nicotinamide adenine dinucleotide phosphate | Cytosol |
| nadp | Nicotinamide adenine dinucleotide phosphate | Endoplasmic Reticulum |
| nadp | Nicotinamide adenine dinucleotide phosphate | Mitochondria |
| nadph | Nicotinamide adenine dinucleotide phosphate - reduced | Cytosol |
| nadph | Nicotinamide adenine dinucleotide phosphate - reduced | Endoplasmic Reticulum |
| nadph | Nicotinamide adenine dinucleotide phosphate - reduced | Mitochondria |

TABLE 4-continued

Reactions and Metabolites in CHO Model

| | | |
|---|---|---|
| nh4 | Ammonium | Cytosol |
| nh4 | Ammonium | Extra-organism |
| nh4 | Ammonium | Mitochondria |
| nrvnc | nervonic acid | Cytosol |
| nrvnc | nervonic acid | Extra-organism |
| nrvnccoa | nervonyl coenzyme A | Cytosol |
| nrvnccoa | nervonyl coenzyme A | Mitochondria |
| nrvnccrn | Nervonyl carnitine | Cytosol |
| nrvnccrn | Nervonyl carnitine | Mitochondria |
| o2 | O2 | Cytosol |
| o2 | O2 | Endoplasmic Reticulum |
| o2 | O2 | Extra-organism |
| o2 | O2 | Mitochondria |
| o2 | O2 | Peroxisome |
| o2- | Superoxide | Cytosol |
| o2- | Superoxide | Mitochondria |
| o2- | Superoxide | Peroxisome |
| oaa | Oxaloacetate | Cytosol |
| oaa | Oxaloacetate | Mitochondria |
| occoa | Octanoyl-CoA (C8:0CoA) | Mitochondria |
| ocdca | octadecanoate (n-C18:0) | Cytosol |
| ocdca | octadecanoate (n-C18:0) | Extra-organism |
| ocdcea | octadecenoate (n-C18:1) | Cytosol |
| ocdcea | octadecenoate (n-C18:1) | Extra-organism |
| ocdcya | octadecdienoate (n-C18:2) | Cytosol |
| ocdcya | octadecdienoate (n-C18:2) | Extra-organism |
| ocdycacoa | octadecadienoyl-CoA (n-C18:2CoA) | Cytosol |
| ocdycacoa | octadecadienoyl-CoA (n-C18:2CoA) | Mitochondria |
| ocdycacrn | octadecadienoyl carnitine (C18:2Crn) | Cytosol |
| ocdycacrn | octadecadienoyl carnitine (C18:2Crn) | Mitochondria |
| octa | Octanoate | Cytosol |
| odecoa | Octadecenoyl-CoA (n-C18:1CoA) | Cytosol |
| odecoa | Octadecenoyl-CoA (n-C18:1CoA) | Mitochondria |
| odecrn | octadecenoyl carnitine | Cytosol |
| odecrn | octadecenoyl carnitine | Mitochondria |
| orn-L | L-Ornithine | Cytosol |
| orn-L | L-Ornithine | Mitochondria |
| orot | Orotate | Cytosol |
| orot5p | Orotidine 5'-phosphate | Cytosol |
| pa_CHO | Phosphatidate, CHO specific | Cytosol |
| pa_CHO | Phosphatidate, CHO specific | Mitochondria |
| pan4p | Pantetheine 4'-phosphate | Cytosol |
| pc_CHO | phosphatidylcholine, CHO specific | Cytosol |
| pe_CHO | phosphatidylethanolamine, CHO specific | Cytosol |
| pep | Phosphoenolpyruvate | Cytosol |
| pep | Phosphoenolpyruvate | Mitochondria |
| pg_CHO | phosphatidylglycerol, CHO specific | Mitochondria |
| pgp_CHO | Phosphatidylglycerophosphate, CHO specific | Mitochondria |
| phe-L | L-Phenylalanine | Cytosol |
| phe-L | L-Phenylalanine | Extra-organism |
| pheme | Protoheme | Cytosol |
| pheme | Protoheme | Extra-organism |
| pheme | Protoheme | Mitochondria |
| pi | Phosphate | Cytosol |
| pi | Phosphate | Endoplasmic Reticulum |
| pi | Phosphate | Extra-organism |
| pi | Phosphate | Mitochondria |
| pi | Phosphate | Peroxisome |
| pino_CHO | phosphatidyl-1D-myo-inositol, CHO specific | Cytosol |
| pmtcoa | Palmitoyl-CoA (n-C16:0CoA) | Cytosol |
| pmtcoa | Palmitoyl-CoA (n-C16:0CoA) | Mitochondria |
| pmtcrn | L-Palmitoylcarnitine (C16:0Crn) | Cytosol |
| pmtcrn | L-Palmitoylcarnitine (C16:0Crn) | Mitochondria |
| pnto-R | (R)-Pantothenate | Cytosol |
| pnto-R | (R)-Pantothenate | Extra-organism |
| ppbng | Porphobilinogen | Cytosol |
| ppcoa | Propanoyl-CoA (C3:0CoA) | Mitochondria |
| ppi | Diphosphate | Cytosol |
| ppi | Diphosphate | Endoplasmic Reticulum |
| ppi | Diphosphate | Mitochondria |
| ppp9 | Protoporphyrin | Cytosol |
| ppp9 | Protoporphyrin | Mitochondria |
| pppg9 | Protoporphyrinogen IX | Cytosol |
| pppi | Inorganic triphosphate | Cytosol |
| pram | 5-Phospho-beta-D-ribosylamine | Cytosol |

TABLE 4-continued

Reactions and Metabolites in CHO Model

| | | |
|---|---|---|
| pro-L | L-Proline | Cytosol |
| pro-L | L-Proline | Extra-organism |
| pro-L | L-Proline | Mitochondria |
| prpp | 5-Phospho-alpha-D-ribose 1-diphosphate | Cytosol |
| ps_CHO | Phosphatidylserine, CHO specific | Cytosol |
| pser-L | O-Phospho-L-serine | Cytosol |
| ptrc | Putrescine | Cytosol |
| ptrc | Putrescine | Mitochondria |
| pyr | Pyruvate | Cytosol |
| pyr | Pyruvate | Mitochondria |
| q10h2 | Ubiquinol-10 | Mitochondria |
| r5p | alpha-D-Ribose 5-phosphate | Cytosol |
| ru5p-D | D-Ribulose 5-phosphate | Cytosol |
| s7p | Sedoheptulose 7-phosphate | Cytosol |
| sarcs | Sarcosine | Cytosol |
| sarcs | Sarcosine | Peroxisome |
| ser-L | L-Serine | Cytosol |
| ser-L | L-Serine | Extra-organism |
| ser-L | L-Serine | Mitochondria |
| so3 | Sulfite | Cytosol |
| so3 | Sulfite | Extra-organism |
| sphgmy_CHO | Sphingomyeline, CHO specific | Cytosol |
| sphgn | Sphinganine | Cytosol |
| spmd | Spermidine | Cytosol |
| sprm | Spermine | Cytosol |
| spyr | 3-Sulfinylpyruvate | Cytosol |
| sql | Squalene | Endoplasmic Reticulum |
| Ssq23epx | (S)-Squalene-2,3-epoxide | Endoplasmic Reticulum |
| strcoa | Stearyl-CoA (n-C18:0CoA) | Cytosol |
| strcoa | Stearyl-CoA (n-C18:0CoA) | Mitochondria |
| strcrn | Stearoylcarnitine (C18:0Crn) | Cytosol |
| strcrn | Stearoylcarnitine (C18:0Crn) | Mitochondria |
| strdnccoa | stearidonyl coenzyme A (C18:4CoA) | Cytosol |
| succ | Succinate | Mitochondria |
| succoa | Succinyl-CoA | Mitochondria |
| sucsal | Succinic semialdehyde | Mitochondria |
| tdcoa | Tetradecanoyl-CoA (n-C14:0CoA) | Cytosol |
| tdcoa | Tetradecanoyl-CoA (n-C14:0CoA) | Mitochondria |
| tdcrn | tetradecanoylcarnitine (C14:0Crn) | Cytosol |
| tdcrn | tetradecanoylcarnitine (C14:0Crn) | Mitochondria |
| thbpt | Tetrahydrobiopterin | Cytosol |
| thf | 5,6,7,8-Tetrahydrofolate | Cytosol |
| thf | 5,6,7,8-Tetrahydrofolate | Mitochondria |
| thr-L | L-Threonine | Cytosol |
| thr-L | L-Threonine | Extra-organism |
| thr-L | L-Threonine | Mitochondria |
| trdox | Oxidized thioredoxin | Cytosol |
| trdrd | Reduced thioredoxin | Cytosol |
| triglyc_CHO | Triglyceride, CHO specific | Cytosol |
| trp-L | L-Tryptophan | Cytosol |
| trp-L | L-Tryptophan | Extra-organism |
| tsul | Thiosulfate | Cytosol |
| ttc | tetracosanoate (n-C24:0) | Cytosol |
| ttc | tetracosanoate (n-C24:0) | Extra-organism |
| ttdca | tetradecanoate (C14:0) | Cytosol |
| ttdca | tetradecanoate (C14:0) | Extra-organism |
| tyr-L | L-Tyrosine | Cytosol |
| tyr-L | L-Tyrosine | Extra-organism |
| ubq10 | Ubiquinone-10 | Mitochondria |
| udp | UDP | Cytosol |
| udpg | UDPglucose | Cytosol |
| ump | UMP | Cytosol |
| uppg3 | Uroporphyrinogen III | Cytosol |
| urcan | Urocanate | Cytosol |
| urea | Urea | Cytosol |
| urea | Urea | Extra-organism |
| urea | Urea | Mitochondria |
| utp | UTP | Cytosol |
| val-L | L-Valine | Cytosol |
| val-L | L-Valine | Extra-organism |
| val-L | L-Valine | Mitochondria |
| xmp | Xanthosine 5'-phosphate | Cytosol |
| xu5p-D | D-Xylulose 5-phosphate | Cytosol |
| zym_int2 | Zymosterone | Endoplasmic Reticulum |

TABLE 4-continued

Reactions and Metabolites in CHO Model

| zymst | Zymosterol | Endoplasmic Reticulum |
| zymstnl | Zymostenol | Endoplasmic Reticulum |

What is claimed is:

1. An auxotrophic mammalian cell genetically engineered to disrupt expression of a protein, said cell comprising:
    a gene disruption of a gene encoding a glycine N-methyltransferase,
    wherein said glycine N-methyltransferase is inactive or not expressed in said auxotrophic mammalian cell; and
    wherein said auxotrophic mammalian cell is unable to grow or undergoes cell death in the absence of cysteine.

2. The auxotrophic mammalian cell of claim 1,
    wherein said auxotrophic mammalian cell further comprises an exogenous nucleic acid, wherein said exogenous nucleic acid comprises an expressible nucleic acid comprising a nucleic acid encoding a protein corresponding to said inactive or not expressed glycine N-methyltransferase in said auxotrophic mammalian cell.

3. The auxotrophic mammalian cell of claim 2,
    wherein said exogenous nucleic acid further comprises an expressible nucleic acid encoding a product.

4. A composition comprising a cell, wherein said cell comprises a gene disruption of a glycine N-methyltransferase, wherein said glycine N-methyltransferase is inactive or not expressed in said cell, and said cell further comprises an expressible nucleic acid comprising a nucleic acid encoding a protein corresponding to said inactive or not expressed glycine N-methyltransferase in said cell.

5. The composition of claim 4, wherein said exogenous nucleic acid further comprises an expressible nucleic acid encoding a product.

6. A kit comprising the composition of claim 4.

7. The kit of claim 6, wherein the kit further comprises the components of a selection medium for culturing said cell, wherein the components of the selection medium exclude cysteine.

8. The kit of claim 7, wherein the kit further comprises cysteine.

9. A method of selecting for an exogenous nucleic acid in a cell, comprising:
    (a) contacting a plurality of cells of claim 1 with an exogenous nucleic acid encoding a glycine N-methyltransferase, wherein said contacting results in uptake of said exogenous nucleic acid into at least one of said plurality of cells;
    (b) placing said plurality of cells in a selection medium, wherein the components of the selection medium exclude cysteine; and
    (c) culturing said plurality of cells in said selection medium, whereby culturing said plurality cells selects for at least one cell that expresses from said exogenous nucleic acid said glycine N-methyltransferase.

10. The method of claim 9, wherein said exogenous nucleic acid further comprises an expressible nucleic acid encoding a product.

11. The method of claim 9, wherein said product is expressed in said selected cell.

12. The method of claim 11, further comprising isolating the product expressed in the selected cell.

13. A method of expressing a product in a cell, comprising:
    (a) contacting a plurality of cells of claim 1 with an exogenous nucleic acid encoding glycine N-methyltransferase and an expressible nucleic acid encoding said product, wherein said contacting results in uptake of said exogenous nucleic acid into at least one of said plurality of cells;
    (b) placing said plurality of cells in a selection medium, wherein the components of the selection medium exclude cysteine;
    (c) culturing said plurality of cells in said selection medium, whereby culturing said plurality of cells selects for at least one cell that expresses from said exogenous nucleic acid said glycine N-methyltransferase; and
    (d) culturing said selected cell under conditions for expression of said product.

14. The method of claim 13, further comprising isolating the product expressed in the selected cell.

15. An auxotrophic mammalian cell comprising:
    (a) a gene disruption of a glycine N-methyltransferase,
    wherein said glycine N-methyltransferase is inactive or not expressed in said auxotrophic mammalian cell; and
    (b) a mammalian expression vector, said mammalian expression vector comprising an expressible nucleic acid comprising a nucleic acid encoding a protein corresponding to said inactive or not expressed glycine N-methyltransferase.

16. The auxotrophic mammalian cell of claim 15, wherein said auxotrophic mammalian cell is unable to grow or undergoes cell death in the absence of cysteine.

17. The auxotrophic mammalian cell of claim 15, wherein said exogenous nucleic acid further comprises an expressible nucleic acid encoding a product.

* * * * *